(12) United States Patent
Ashley et al.

(10) Patent No.: US 7,947,280 B2
(45) Date of Patent: May 24, 2011

(54) APELIN AND USES THEREOF

(75) Inventors: Euan A. Ashley, Palo Alto, CA (US);
Mary M. Chen, Fremont, CA (US);
Thomas Quertermous, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/985,460

(22) Filed: Nov. 14, 2007

(65) Prior Publication Data

US 2008/0182779 A1    Jul. 31, 2008

Related U.S. Application Data

(63) Continuation-in-part of application No. 10/850,941, filed on May 21, 2004, now abandoned.

(60) Provisional application No. 60/472,619, filed on May 22, 2003.

(51) Int. Cl.
*A61K 39/00* (2006.01)
*C07K 4/00* (2006.01)
*C07K 4/12* (2006.01)

(52) U.S. Cl. .................................... 424/185.1; 530/327

(58) Field of Classification Search .................. None
See application file for complete search history.

(56) References Cited

U.S. PATENT DOCUMENTS 6,492,234 B1 * 12/2002 Moroni et al. ................ 438/305
6,492,324 B1 * 12/2002 Hinuma et al. .................. 514/2
2005/0075275 A1    4/2005 Albrecht et al.

FOREIGN PATENT DOCUMENTS

CA            2456223 A1 *  2/2003
WO    WO2005/106493 A1    11/2005

OTHER PUBLICATIONS

Tatemoto et al, regulatory peptides 99: 87-92, 2001.*
Japp et al, Biochemical Pharmacology 75: 1882-1892, 2008.*
Ashley et al, Cardiovasc Res: 65(1): 73-82, Jan. 1, 2005.*
Berry et al, Circulation 110 (suppl II): 187-193, 2004.*
Tatemoto et al, Biochemical and Biophysical Research Communications 251: 471-476, 1998.*
Chen et al, Circulation 108: 1432-1439, 2003.*
Doevendans, "Unravelling the pathophysiology of heart failure through human genomics," Eur. J Clin. Invest., 2001, 31(5):378-379.
Heerdt et al, "Chronic unloading by left ventricular assist device reverses contractile dysfunction and alters gene expression in end-stage heart failure," Circulation, 2000, 102(22):2713-2719.
Lee, "Use of microarrays to identify targets in cardiovascular disease," Drug News Persepct., 2000, 13(7):403-406.

* cited by examiner

*Primary Examiner* — Phuong Huynh
(74) *Attorney, Agent, or Firm* — Bozicevic, Field & Francis LLP; Pamela J. Sherwood

(57) ABSTRACT

The invention provides a method of treating or preventing heart failure or a disease or condition associated with heart failure comprising administering an effective dose of an apelin peptide or APJ receptor ligand to the subject. According to certain embodiments of the invention the apelin peptide is administered chronically. In certain embodiments of the invention the apelin peptide is administered in an amount effective to improve at least one hemodynamic parameter or prognostic variable for heart failure. Clinical conditions associated with heart failure include, but are not limited to, atherosclerosis, restenosis, ischemic cardiovascular diseases, idiopathic or viral cardiomyopathy, and the like.

12 Claims, 21 Drawing Sheets

FIGURE 12
*a*
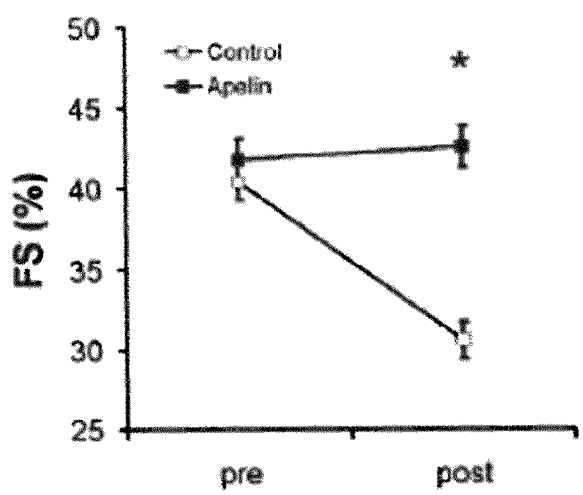
*b*
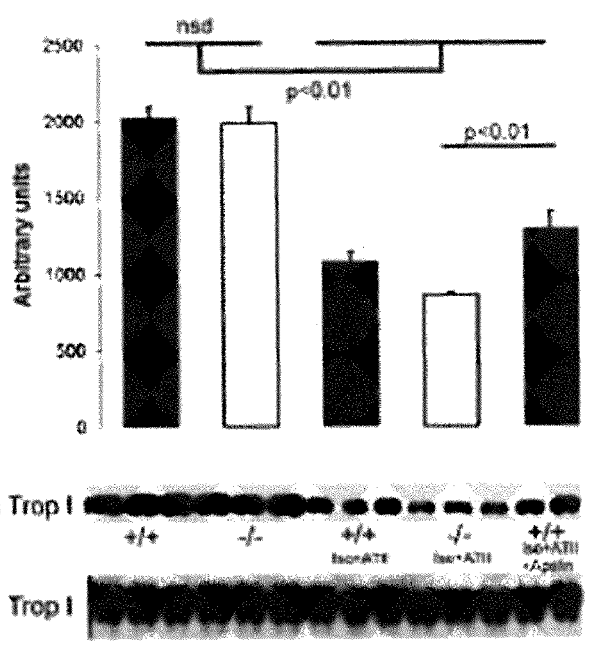

FIGURE 13
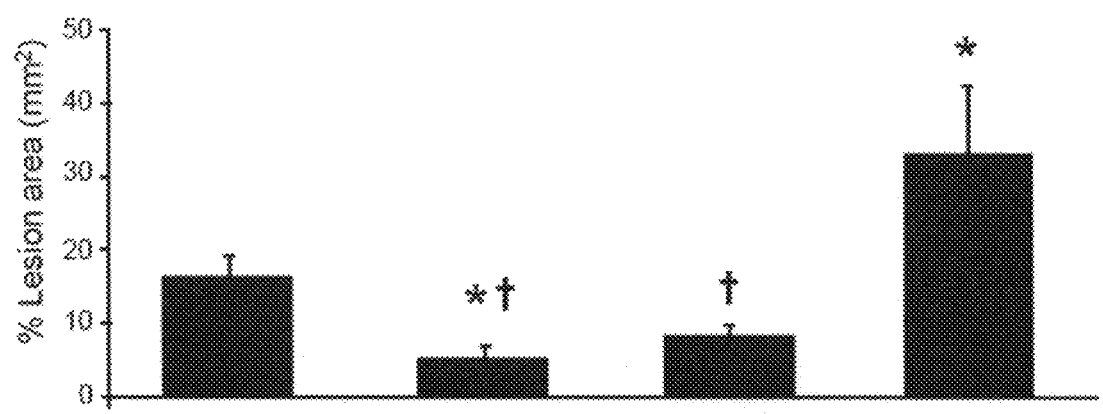
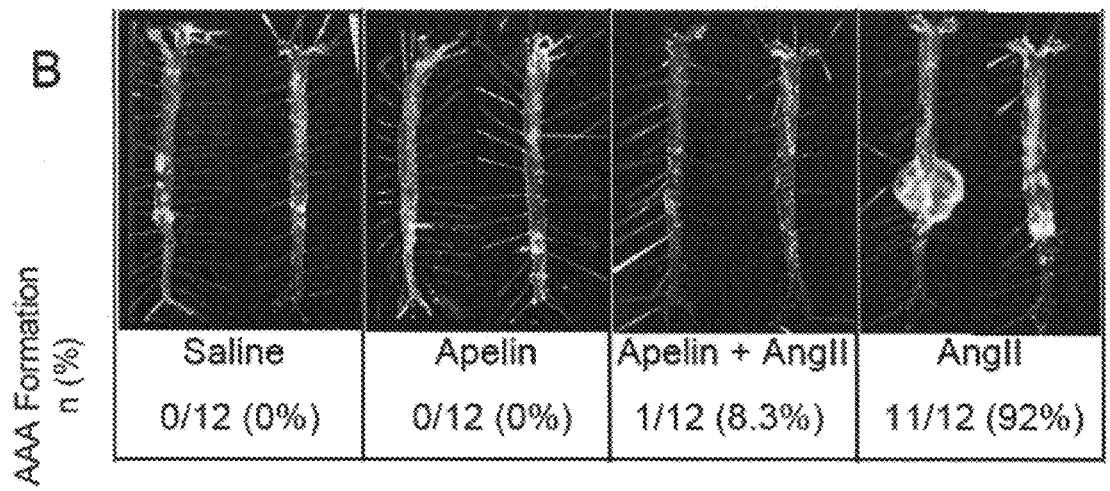

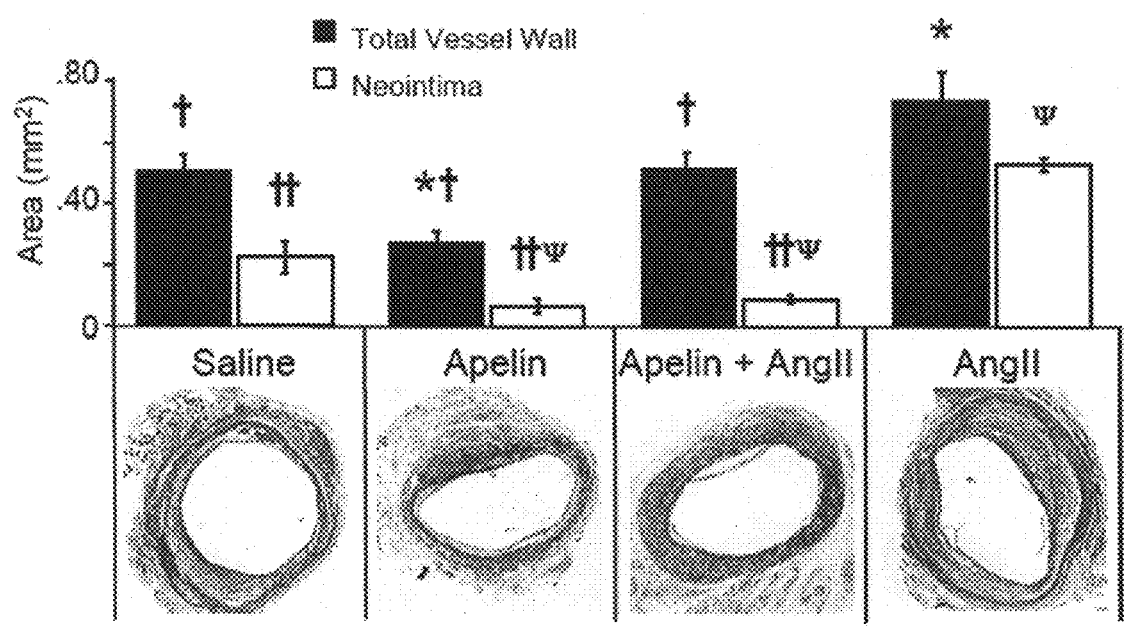

APELIN AND USES THEREOF

CROSS-REFERENCE TO RELATED APPLICATION

This application is a continuation in part of U.S. patent application Ser. No. 10/850,941, filed May 21, 2004, which application claims priority to U.S. Provisional Patent Application 60/472,619, filed May 22, 2003, each of which are incorporated herein by reference.

BACKGROUND OF THE INVENTION

Heart failure is a pathophysiological state in which the heart is unable to pump enough blood to meet the nutrition and oxygen requirement of metabolizing tissues or cells. It is a major complication in many heart diseases. Adults over the age of 40 have an estimated 21% lifetime risk of developing heart failure (Lloyd-Jones, D. M. et al. Lifetime risk for developing congestive heart failure: the Framingham Heart Study. Circulation 106, 3068-72 (2002), a condition responsible for more hospitalizations than all forms of cancer combined (American Heart Association. Heart Disease and Stroke Statistics—2003 Update, (American Heart Association, Dallas, Tex., 2003)).

Heart failure is a general term that describes the final common pathway of many disease processes. The most common cause is coronary artery disease, which can lead to a myocardial infarction (heart attack), often resulting in death of cardiac cells. The heart must then perform the same work with fewer cells. Chronic obstructive coronary artery disease can also cause heart failure in the absence of myocardial infarction. Valve disease or high blood pressure can lead to heart failure by increasing the workload of the heart. Rarer causes of heart failure, which primarily involve cardiac muscle, are classed as cardiomyopathy (although this term is sometimes used more generally to cover any cause of heart failure). The best characterized are a group of single gene disorders of the sarcomere which cause "hypertrophic cardiomyopathy" (in fact, a misnomer as many patients have no hypertrophy). In contrast, all patients with "dilated cardiomyopathy" have dilated thin walled ventricles. The genetics of this condition have yet to be characterized, but in many cases non-genetic causes are responsible (e.g. infections, alcohol, chemotherapeutic agents). Where no readily identifiable cause is found, the diagnosis used is "idiopathic" dilated cardiomyopathy (generally a diagnosis of exclusion).

A variety of pathophysiological changes occur in the heart as heart failure develops. In response to increased work load in vivo, the heart frequently increases in size (cardiac hypertrophy) as cardiac muscle cells develop hypertrophy (i.e., an increase in cell size in the absence of cell division). At the cellular and molecular levels, cardiac hypertrophy is characterized by increased expression of contractile proteins and activation of various signaling pathways whose role in the pathophysiology of heart failure remains incompletely understood.

Current treatments for heart failure include pharmacological methods, devices such as the ventricular assist device (VAD), and heart and heart-lung transplantation. Pharmacological approaches include the use of inotropic agents (i.e., compounds that increase cardiac contractility), neurohumoral blockers (e.g., .beta.-blockers, angiotensin converting enzyme inhibitors), aldosterone antagonists, diuretics, and vasodilators. However, none of these agents is fully effective either alone or in combination. Availability of transplants is limited, and since many individuals suffering from heart failure are in poor health, they are frequently not good surgical candidates. For these reasons heart failure remains a major cause of morbidity and mortality, particularly in the developed world. In addition, as indicated above it can be difficult to determine the etiology of heart failure, thus impeding the development of more specific therapies. In addition, there is a lack of diagnostic techniques at the molecular level. Thus there is a need in the art for the discovery of additional diagnostic markers and pharmacological targets for the development of new therapeutic approaches. In addition, there is a need in the art for improved techniques for evaluating the severity of heart failure and its response to treatment. The present invention addresses the foregoing needs, among others.

SUMMARY OF THE INVENTION

The invention provides a method of treating or preventing heart failure or a disease or condition associated with heart failure comprising steps of: (i) providing a subject at risk of or suffering from heart failure or a disease or condition associated with heart failure; and (ii) administering a composition comprising an apelin peptide to the subject. According to certain embodiments of the invention the apelin peptide is administered chronically. In certain embodiments of the invention the apelin peptide is administered in an amount effective to improve at least one hemodynamic parameter or prognostic variable for heart failure. Clinical conditions associated with heart failure include, but are not limited to, atherosclerosis, restenosis, ischemic cardiovascular diseases, idiopathic or viral cardiomyopathy, and the like.

In another aspect, the invention provides a method of treating or preventing heart failure or a disease or condition associated with heart failure comprising steps of: (i) providing a subject at risk of or suffering from heart failure or a disease or condition associated with heart failure; and (ii) administering a composition that increases the functional activity of the APJ receptor.

The invention also provides a method of providing diagnostic or prognostic information related to heart failure comprising steps of: (i) providing a subject in need of diagnostic or prognostic information related to heart failure; (ii) determining the level of expression or activity of an apelin peptide, in the subject or in a biological sample obtained from the subject; and (iii) utilizing the information to provide diagnostic or prognostic information.

BRIEF DESCRIPTION OF THE DRAWING

FIG. 1A is a bar graph showing left ventricular tissue apelin level as determined by enzyme immunoassay. The level rose significantly (P<0.001) following offloading by implantation of a left ventricular assist device. Units are ng/ml. FIG. 1B is a tissue section showing immunohistochemical distribution of apelin. Apelin, labeled reddish-brown, is highly localized to endothelial and smooth muscle cells in diseased (right panel) and normal heart. Staining of consecutive sections with PECAM (CD31, middle panels) confirms the specificity of this localization. Control panels (left) represent sections where the incubation in primary antibody step was omitted.

FIG. 2A is a bar graph showing that there were significant increases in the plasma level of apelin as determined by enzyme immunoassay in early heart failure through New York Heart Association (NYHA class 2 (P<0.02). In later stage disease, the mean level is lower, although this change is not significant Class 4 patients (n=7) are combined with class 3 (from left to right, n=34, 24, 12, 38). FIG. 2B is a bar graph showing that apelin rises in mild to moderate LV dysfunction but falls in severe disease (P<0.02 for both). Normal is defined as a left ventricular ejection fraction greater than 45%, mild to moderate is 25-45%; and severe is less than 25% (from left to right, n=42, 28, 40).

FIGS. 12A-12B. The apelin ligand rescues the heart failure phenotype in a neurohormonal model of cardiomyopathy in 12 to 14 week old mice. (a) Echocardiographic analyses revealed markedly decreased fractional shortening in both apelin null and wild type mice given catecholamine infusions of isoproterenol (Iso) and angiotensin II (ATII) for seven days via osmotic minipump, consistent with downregulation of apelin-APJ expression seen in severe heart failure. *, P<0.001, n=10 mice per group. As previously shown, a significant decrease was seen in baseline contractility of the apelin null mice (P<0.05). Concomitant apelin infusion via a second osmotic minipump in a group of wild type mice ameliorates the heart failure phenotype completely, with maintenance of normal fractional shortening demonstrated by echocardiography. *, P<0.001, n=10 mice per group. (b) Both the apelin null and wildtype groups of mice with induced heart failure have significantly decreased levels of troponin I phosphorylation at the serine 23/24 residue assessed via immunoblotting compared with basal levels. The rescued group of wildtype mice with normal contractility maintained by apelin administration, however, shows a significantly increased level of troponin I phosphorylation compared with the apelin null mice with heart failure. *, P<0.01 between groups as indicated.

FIGS. 13A-13C. Apelin inhibits AngII mediated progression of atherosclerosis in murine models of vascular disease. a) Delivery of apelin by osmotic minipump decreased lesion burden in the standard apoE knockout model, and also mitigated the increased lesion burden when co-administered with AngII by osmotic minipump. Shown are means and SEM. b) ApoE knockout animals treated with AngII for four weeks showed a significant increase in aneurysm formation, and this effect was mitigated by apelin treatment (11/12 animals compared to 1/12 animals). Two representative aortas are shown for each experimental group. c) In a vein graft model in apoE knockout mice, apelin administered by minipump significantly decreased neointimal area. AngII significantly increased neointimal area, and this effect was completely blocked by apelin. Vascular remodeling in this model was also decreased by apelin, and the AngII mediated increase in remodeling was mitigated by apelin. Representative vein graft sections are shown, staining with Masson/Goldner stain for analysis. Shown are means and SEM.

DEFINITIONS

Figure 1A:
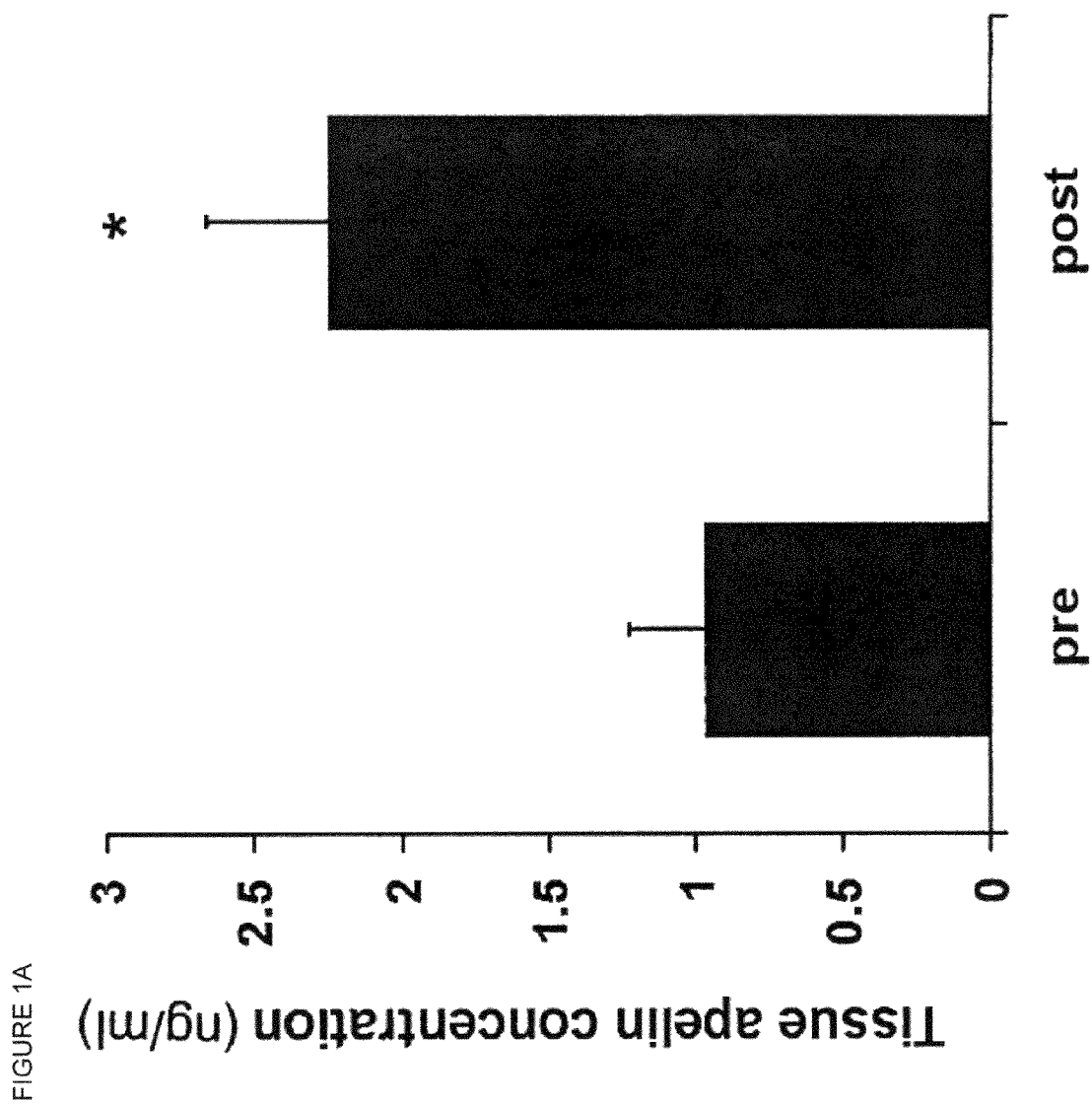
FIGS. 1A and 1B show apelin level and distribution in human left ventricle.

This application refers to various patents, patent applications, journal articles, and other publications, all of which are incorporated herein by reference. In addition, the following standard reference works are incorporated herein by reference: Current Protocols in Molecular Biology, Current Protocols in Immunology, Current Protocols in Protein Science, and Current Protocols in Cell Biology, John Wiley & Sons, N.Y., edition as of July 2002; Sambrook, Russell, and Sambrook, Molecular Cloning: A Laboratory Manual, 3.sup.rd ed., Cold Spring Harbor Laboratory Press, Cold Spring Harbor, 2001; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y., Braunwald, E., Zipes, D. P., and Libby, P. (eds.) Heart Disease: A Textbook of Cardiovascular Medicine. W B Saunders; 6th edition (Feb. 15, 2001); Chien, K. R., Molecular Basis of Cardiovascular Disease: A Companion to Braunwald's Heart Disease, W B Saunders; Revised edition (2003); and Goodman and Gilman's The Pharmacological Basis of Therapeutics, 10.sup.th Ed. McGraw Hill, 2001 (referred to herein as Goodman and Gilman). In case of conflict between the instant specification and any document incorporated by reference, the specification shall control.

To facilitate understanding of the description of the invention, the following definitions are provided. It is to be understood that, in general, terms not otherwise defined are to be given their meaning or meanings as generally accepted in the art.

Antibody: In general, the term "antibody" refers to an immunoglobulin, which may be natural or wholly or partially synthetically produced in various embodiments of the invention. An antibody may be derived from natural sources (e.g., purified from a rodent, rabbit, chicken (or egg) from an animal that has been immunized with an antigen or a construct that encodes the antigen) partly or wholly synthetically produced. An antibody may be a member of any immunoglobulin class, including any of the human classes: IgG, IgM, IgA, IgD, and IgE. The antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., Nature Reviews Cancer, Vol. 2, 750-765, 2002, and references therein. Preferred antibodies, antibody fragments, and/or protein domains comprising an antigen binding site may be generated and/or selected in vitro, e.g., using techniques such as phage display (Winter, G. et al. 1994. Annu. Rev. Immunol. 12:433-455, 1994), ribosome display (Hanes, J., and Pluckthun, A. Proc. Natl. Acad. Sci. USA. 94:4937-4942, 1997), etc. In various embodiments of the invention the antibody is a "humanized" antibody in which for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., Nature Biotechnology, 16: 535-539, 1998. An antibody may be polyclonal or monoclonal, though for purposes of the present invention monoclonal antibodies are generally preferred.

Apelin was originally isolated from bovine stomach extracts by measuring extracellular acidification in a cell line expressing human APJ (Tatemoto K., et al). Apelin appears to exert its effects at least in part by activating $Na^+$—$H^+$ exchanger (NHE) isoform-1 (which exchanges extracellular $Na^+$ for intracellular $H^+$) and also by activating $Na^+$—$Ca^{++}$ exchanger (NCX) working in reverse mode ($Na^+$ out, $Ca^{++}$ in) (Szokodi et al. Circ Res., 91:434-40, 2002). Thus APJ is believed to couple to these proteins and bring about an increase in their functional activity. Thus activation of APJ results in decreased extracellular pH, increased intracellular pH, decreased extracellular $Ca^{++}$ concentration and increased intracellular $Ca^{++}$ concentration.

The role of apelin in cardiovascular physiology has been little investigated. Early studies showed a decrease in mean arterial pressure following an intravenous bolus injection of apelin in rats (Tatemoto et al. Regul Pept, 99:87-92, 2001; Lee et al. J Neurochem., 74:34-41, 2000). In addition, APJ knockout mice show an increased vasopressor response to angiotensin II, suggesting a counter-regulatory role in relation to the renin-angiotensin system. However, another group reported that apelin potently contracts isolated human saphenous vein, suggesting the effect of apelin on vascular reactivity remains unclear (Katugampola et al. Br J Pharmacol., 132:1255-60, 2001). In relation to myocardial function, Szokodi et al, (referenced above) showed an effect of apelin on the contractility of the isolated rat heart that was both potent (EC50 in the low picomolar range) and efficacious (maximum developed tension was 70% that of isoproterenol). However, despite these significant effects, the role of apelin in vivo, both under normal physiological conditions and in pathological states such as heart failure, has remained unknown. For example, the balance of effects on cardiac loading and intrinsic contractility (ventriculo-vascular coupling) has not been heretofore described.

Apelin and APJ are widely expressed in homogenates from rat and mouse organs (Medhurst et al. J Neurochem 84, 1162-1172 (2003)) and share identity with angiotensinogen and the angiotensin receptor AT1 respectively. However, angiotensin II does not bind to APJ. Additional characteristics and studies of apelin are described in the following references: Tatemoto et al. Regul Pept 99, 87-92 (2001); Seyedabadi et al. Auton Neurosci 101, 32-8 (2002); Szokodi et al. Circ Res 91, 434-40 (2002); Katugampola et al. Br J Pharmacol 132, 1255-60 (2001); Lee et al. J Neurochem 74, 34-41 (2000); Shah Cardiovasc Res 31, 847-67 (1996); De Falco et al. In Vivo 16, 333-6 (2002). It is noted that although the genes identified herein are human genes, the corresponding genes in other mammalian species are also of relevance. In particular, the invention encompasses diagnostic and therapeutic methods for use in non-human mammalian species based on the corresponding genes in such species. While the tissue samples contained cardiac cells of all types, the predominance of myocytes and endothelial cells in the samples indicates that expression data is indicative of the expression state of myocytes and/or endothelial cells. Expression patterns in other cell types present within the heart may be similar.

It is noted that both apelin and APJ are highly conserved across multiple species, and apelin-77 is subject to similar processing, resulting in formation of smaller peptides. In particular, Apelin-12 is 100% identical in human, mouse, and rat. A summary of information on apelin and APJ in human, mouse, and rat is presented in Table 2B.

Cardiac cell: The term "cardiac cell" refers to cardiac myocytes and/or cardiac endothelial cells. According to certain embodiments of the invention the term includes cardiac fibroblasts and/or other cell types present in the heart such as smooth muscle cells (e.g., in the walls of cardiac blood vessels), neurons and glial cells in cardiac nerves, etc.

Diagnostic information: As used herein, "diagnostic information" or information for use in diagnosis is any information that is useful in determining whether a subject has or is susceptible to developing a disease or condition, and/or in classifying the disease or condition into a phenotypic category or any category having significance with regards to the prognosis of or likely response to treatment of the disease or condition. The term includes prenatal diagnosis, i.e., diagnosis performed prior to the birth of the subject, including performing genetic testing on germ cells (ova and/or sperm). The term also includes determining the genotype of a subject with respect to an apelin or APJ receptor gene for any purpose.

Diagnostic target: A gene is considered to be a "diagnostic target" if detection and/or measurement of its expression level is useful in providing diagnostic or prognostic information related to a disease or clinical condition, or for monitoring the physiological state of a cell, tissue, or organism (including monitoring the response to therapy or the progression of disease). Expression products of such genes (RNA or polypeptide) may also be referred to as diagnostic targets.

Differential expression: A gene or cDNA clone exhibits "differential expression" at the RNA level if its RNA transcript varies in abundance between different cell types, tissues, samples, etc., at different times, or under different conditions. A gene exhibits differential expression at the protein level if a polypeptide encoded by the gene or cDNA clone varies in abundance between different cell types, tissues, samples, etc., or at different times. In the context of a microarray experiment, differential expression generally refers to differential expression at the RNA level. Differential expression, as used herein, may refer to both quantitative as well as qualitative differences in the temporal and/or tissue expression patterns. In general, differentially expressed genes may be used to identify or detect particular cell types, tissues, physiological states, etc., to distinguish between different cell types, tissues, or physiological states. Differentially expressed genes and their expression products may be diagnostic and/or therapeutic targets or may interact with such targets.

Effective amount: In general, an "effective amount" of an active agent refers to an amount necessary to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, in the case of an agent for the treatment of heart failure, an effective amount may be an amount sufficient to result in clinical improvement of the patient, e.g., increased exercise tolerance/capacity, increased blood pressure, decreased fluid retention, decreased dyspnea, subjective improvement of other symptoms, etc., and/or improved results on a quantitative test of cardiac functioning, e.g., ejection fraction, exercise capacity (e.g., time to exhaustion), etc.

According to certain embodiments of the invention an effective amount results in an improvement in a quantitative measure or index that reflects cardiovascular system functioning or heart failure severity of at least 5%, or preferably at least 10%, at least 20%, or more. For example, an effective amount may increase a measure of exercise capacity by at least 5%, at least 10%, etc., relative to the value in the absence of treatment or when an alternate therapy is administered. An effective amount may increase ejection fraction by at least 5%, at least 10%, at least 20% or more. According to certain embodiments of the invention, where the value for a quantitative measure or index in a subject suffering from heart failure or a condition or disease associated with heart failure differs from the average value for similar normal subjects (e.g., subjects matched for variables such as age, weight, sex, etc., but not suffering from heart failure or a disease or condition associated with heart failure) or differs from a previous value measured in the same subject when not suffering from heart failure, an effective amount restores the measure or index at least 10%, at least 20%, or at least 50% of the way towards its value as measured in normal, matched subjects or in the same subject when not suffering from heart failure.

Gene: For the purposes of the present invention, the term "gene" has its meaning as understood in the art. In general, a gene is taken to include gene regulatory sequences (e.g., promoters, enhancers, etc.) and/or intron sequences, in addition to coding sequences (open reading frames). It will further be appreciated that definitions of "gene" include references to nucleic acids that do not encode proteins but rather encode functional RNA molecules such as tRNAs. For the purpose of clarity it is noted that, as used in the present application, the term "gene" generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid.

Gene product or expression product: A "gene product" or "expression product" is, in general, an RNA transcribed from the gene (e.g., either pre- or post-processing) or a polypeptide encoded by an RNA transcribed from the gene (e.g., either pre- or post-modification). A compound or agent is said to increase gene expression if application of the compound or agent to a cell or subject results in an increase in either an RNA or polypeptide expression product or both. A compound or agent is said to decrease gene expression if application of the compound or agent to a cell or subject results in a decrease in either an RNA or polypeptide expression product or both.

Hybridize: The term "hybridize", as used herein, refers to the interaction between two complementary nucleic acid sequences. The phrase "hybridizes under high stringency conditions" describes an interaction that is sufficiently stable that it is maintained under art-recognized high stringency conditions. Guidance for performing hybridization reactions can be found, for example, in Current Protocols in Molecular Biology, John Wiley & Sons, N.Y., 6.3.1-6.3.6, 1989, and more recent updated editions, all of which are incorporated by reference. See also Sambrook, Russell, and Sambrook, Molecular Cloning: A Laboratory Manual, 3rd ed., Cold Spring Harbor Laboratory Press, Cold Spring Harbor, 2001. Aqueous and nonaqueous methods are described in that reference and either can be used. Typically, for nucleic acid sequences over approximately 50-100 nucleotides in length, various levels of stringency are defined, such as low stringency (e.g., 6× sodium chloride/sodium citrate (SSC) at about 45° C., followed by two washes in 0.2×SSC, 0.1% SDS at least at 50° C. (the temperature of the washes can be increased to 55° C. for medium-low stringency conditions)); medium stringency (e.g., 6×SSC at about 45° C., followed by one or more washes in 0.2×SSC, 0.1% SDS at 60° C.); high stringency (e.g., 6×SSC at about 45° C., followed by one or more washes in 0.2×SSC, 0.1% SDS at 65° C.); and very high stringency (e.g., 0.5M sodium phosphate, 0.1% SDS at 65° C., followed by one or more washes at 0.2×SSC, 1% SDS at 65° C.) Hybridization under high stringency conditions only occurs between sequences with a very high degree of complementarity. One of ordinary skill in the art will recognize that the parameters for different degrees of stringency will generally differ based various factors such as the length of the hybridizing sequences, whether they contain RNA or DNA, etc. For example, appropriate temperatures for high, medium, or low stringency hybridization will generally be lower for shorter sequences such as oligonucleotides than for longer sequences.

Isolated: As used herein, "isolated" means 1) separated from at least some of the components with which it is usually associated in nature; 2) prepared or purified by a process that involves the hand of man; and/or 3) not occurring in nature.

Ligand: As used herein, "ligand" means a molecule that specifically binds to a target such as a polypeptide through a mechanism other than an antigen-antibody interaction. The term encompasses, for example, polypeptides, peptides, and small molecules, either naturally occurring or synthesized, including molecules whose structure has been invented by man. Although the term is frequently used in the context of receptors and molecules with which they interact and that typically modulate their activity, the term as used herein applies more generally.

Marker: A "marker" may be any gene or gene product (e.g., protein, peptide, mRNA) that indicates or identifies a particular-diseased or physiological state (e.g., carcinoma, normal, dysplasia) or indicates or identifies a particular cell type, tissue type, or origin. The expression or lack of expression of a marker gene may indicate a particular physiological or diseased state of a patient, organ, tissue, or cell. Preferably, the expression or lack of expression may be determined using standard techniques such as Northern blotting, in situ hybridization, RT-PCR, real-time RT-PCR, sequencing, immunochemistry, immunoblotting, oligonucleotide or cDNA microarray or membrane array, protein microarray analysis, mass spectrometry, etc. In certain embodiments of the invention, the level of expression of a marker gene is quantifiable.

Operably linked: As used herein, "operably linked" refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective three-dimensional association is acceptable.

Peptide, polypeptide, or protein: According to the present invention, a "peptide", "polypeptide", or "protein" comprises. a string of at least three amino acids linked together by peptide bonds. The terms may be used interchangeably although a peptide generally represents a string of between approximately 8 and 30 amino acids. Peptide may refer to an individual peptide or a collection of peptides. Peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide, but such modifications may confer desirable properties, e.g., enhanced biological activity, on the peptide.

One of ordinary skill in the art will appreciate that various amino acid substitutions, e.g, conservative amino acid substitutions, may be made in the sequence of any of the apelin peptides described herein, without necessarily decreasing its activity. Conservative substitutions (i.e., substitutions with amino acids of comparable chemical characteristics) are particularly preferred. For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

A compound or agent is said to increase expression of a polypeptide if application of the compound or agent to a cell or subject results in an increase in the amount of the polypeptide. A compound or agent is said to decrease expression of a polypeptide if application of the compound or agent to a cell or subject results in a decrease in the amount of the polypeptide.

Polynucleotide or oligonucleotide: "Polynucleotide" or "oligonucleotide" refers to a polymer of nucleotides. Typically, a polynucleotide comprises at least three nucleotides. The polymer may include natural nucleosides (e.g., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A compound or agent is said to increase expression of a polynucleotide if application of the compound or agent to a cell or subject results in an increase in the amount of the polynucleotide or of a translation product of the polynucleotide or both. A compound or agent is said to decrease expression of a polynucleotide if application of the compound or agent to a cell or subject results in a decrease in the amount of the polynucleotide or of a translation product of the polynucleotide or both.

Prognostic information and predictive information: As used herein the terms "prognostic information" and "predictive information" are used interchangeably to refer to any information that may be used to foretell any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Purified: As used herein, "purified" means separated from one or more compounds or entities, e.g., one or more compounds or entities with which it is naturally found. A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure. In the context of a preparation of a single nucleic acid molecule, a preparation may be considered substantially pure if the nucleic acid represents a majority of all nucleic acid molecules in the preparation, preferably at least 75%, yet more preferably at least 90%, or greater, as listed above.

Regulatory sequence: The term "regulatory sequence" is used herein to describe a region of nucleic acid sequence that directs, enhances, or inhibits the expression (particularly transcription, but in some cases other events such as splicing or other processing) of sequence(s) with which it is operatively linked. The term includes promoters, enhancers and other transcriptional control elements. In some embodiments of the invention, regulatory sequences may direct constitutive expression of a nucleotide sequence; in other embodiments, regulatory sequences may direct tissue-specific and/or inducible expression. For instance, non-limiting examples of tissue-specific promoters appropriate for use in mammalian cells include lymphoid-specific promoters (see, for example, Calame et al., Adv. Immunol. 43:235, 1988) such as promoters of T cell receptors (see, e.g., Winoto et al., EMBO J. 8:729, 1989) and immunoglobulins (see, for example, Banerji et al., Cell 33:729, 1983; Queen et al., Cell 33:741, 1983), and neuron-specific promoters (e.g., the neurofilament promoter; Byrne et al., Proc. Natl. Acad. Sci. USA 86:5473, 1989). Developmentally-regulated promoters are also encompassed, including, for example, the murine hox promoters (Kessel et al., Science 249:374, 1990) and the .alpha.-fetoprotein promoter (Campes et al., Genes Dev. 3:537, 1989). In some embodiments of the invention regulatory sequences may direct expression of a nucleotide sequence only in cells that have been infected with an infectious agent. For example, the regulatory sequence may comprise a promoter and/or enhancer such as a virus-specific promoter or enhancer that is recognized by a viral protein, e.g., a viral polymerase, transcription factor, etc.

Sample: As used herein, a "sample" obtained from a subject may include, but is not limited to, any or all of the following: a cell or cells, a portion of tissue, blood, serum, ascites, urine, saliva, amniotic fluid, cerebrospinal fluid, and other body fluids, secretions, or excretions. The sample may be a tissue sample obtained, for example, from skin, muscle, buccal or conjunctival mucosa, placenta, gastrointestinal tract or other organs. A sample of DNA from fetal or embryonic cells or tissue can be obtained by appropriate methods, such as by amniocentesis or chorionic villus sampling. The term "sample" may also refer to any material derived by isolating, purifying, and/or processing a sample obtained directly from a subject. Derived samples may include nucleic acids or proteins extracted from the sample or obtained by subjecting the sample to techniques such as amplification or reverse transcription of mRNA, etc. A derived sample may be, for example, a homogenate, lysate, or extract prepared from a tissue, cells, or other constituent of an organism (e.g., a body fluid).

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Specific binding: As used herein, the term "specific binding" refers to an interaction between a target molecule (typically a target polypeptide) and a binding molecule such as an antibody or ligand. The interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute but generally refers to the context in which the binding is performed. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target polypeptide versus the affinity of the binding molecule for other targets, e.g., competitors. If a binding molecule exhibits a high affinity for a target molecule that it is desired to detect and low affinity for nontarget molecules, the antibody will likely be an acceptable reagent for immunodiagnostic purposes. Once the specificity of a binding molecule is established in one or more contexts, it may be employed in other, preferably similar, contexts without necessarily re-evaluating its specificity. In the context of an interaction between an antibody or ligand and a polypeptide, according to certain embodiments of the invention a molecule exhibits specific binding if it binds to the polypeptide at least 5 times as strongly as to other polypeptides present in a cell lysate, e.g., a myocardial cell lysate. According to certain embodiments of the invention a molecule exhibits specific binding if it binds to the polypeptide at least 10 times as strongly as to other polypeptides present in a cell lysate. According to certain embodiments of the invention a molecule exhibits specific binding if it binds to the polypeptide at least 50 times as strongly as to other polypeptides present in a cell lysate. According to certain embodiments of the invention a molecule exhibits specific binding if it binds to the polypeptide at least 100 times as strongly as to other polypeptides present in a cell lysate.

Subject: The term "subject", as used herein, refers to an individual to whom an agent is to be delivered, e.g., for experimental, diagnostic, and/or therapeutic purposes. Preferred subjects are mammals, including humans. Other preferred mammalian subjects include rats, mice, other rodents, non-human primates, rabbits, sheep, cows, dogs, cats, and other domesticated animals and/or animals of agricultural interest.

Therapeutic target: Certain genes that are differentially expressed in cells, tissues, etc., represent "therapeutic targets", in that modulating expression of such a gene (e.g., increasing expression, decreasing expression, or altering temporal properties of expression) and/or modulating the activity or level of an expression product of the gene may alter the biochemical or physiological properties of the cell or tissue so as to treat or prevent a disease or clinical condition. For example, in the context of the present invention, modulation of the expression of certain of the differentially expressed genes described herein may treat or prevent heart failure. Modulating the activity of an expression product, e.g., by administering a compound such as a small molecule (e.g., an agonist or antagonist) or antibody that affects the activity, by altering phosphorylation or glycosylation state, may treat or prevent heart failure. Expression products (RNA or polypeptide) of the therapeutic target genes may also be referred to as therapeutic targets.

Certain preferred therapeutic targets include, but are not limited to, genes whose encoded polypeptide comprises an extracellular portion. The prediction of protein orientation with respect to the cell membrane and the existence of transmembrane domains can be performed, for example, using the program TMpred (K. Hofmann & W. Stoffel (1993) TMbase—A database of membrane spanning proteins segments. Biol. Chem. Hoppe-Seyler 347,166) and/or the methods described in Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed. J. Glasgow, T. Littlejohn, F. Major, R. Lathrop, D. Sankoff, and C. Sensen. Menlo Park, Calif.: AAAI Press, 1998.

Treating: As used herein, "treating" includes reversing, alleviating, inhibiting the progress of, preventing, or reducing the likelihood of the disease, disorder, or condition to which such term applies, or one or more symptoms or manifestations of such disease, disorder or condition.

Vector: The term "vector" is used herein to refer to a nucleic acid molecule capable of mediating entry of, e.g., transferring, transporting, etc., another nucleic acid molecule into a cell. The transferred nucleic acid is generally linked to, e.g., inserted into, the vector nucleic acid molecule. A vector may include sequences that direct autonomous replication, or may include sequences sufficient to allow integration into host cell DNA. Useful vectors include, for example, plasmids (which may comprise sequences derived from viruses), cosmids, and virus vectors. Virus vectors include, e.g., replication defective retroviruses, adenoviruses, adeno-associated viruses, and lentiviruses. As will be evident to one of ordinary skill in the art, virus vectors may include various viral components in addition to nucleic acid(s) that mediate entry of the transferred nucleic acid.

DETAILED DESCRIPTION OF THE EMBODIMENTS

Heart failure may be understood as a syndrome involving chronic neuro-endocrine activation precipitated by an inability of the heart to maintain perfusion of body tissues. The inventors have identified genes that are upregulated in cardiac tissue e.g., cardiac myocytes and/or cardiac endothelial cells, in subjects with heart failure following implantation of an LVAD. In other words, these genes were upregulated following mechanical offloading. The invention provides a variety of different reagents and methods relating to the treatment and diagnosis of heart failure.

AGTRL1, also known as APJ or the APJ receptor, was identified as the gene most significantly and consistently upregulated following mechanical offloading in heart failure among genes represented on a 12,814 feature microarray. The inventors have shown that apelin circulates in plasma and that its plasma levels can be correlated with disease severity in patients with heart failure. This finding provides a basis for diagnostic and prognostic methods based on measuring circulating apelin levels. The inventors have also shown that apelin is highly specifically localized to the vasculature in cardiac tissue in the human heart. The localization of apelin in normal human cardiac left ventricle was similar to that in end stage, failing left ventricle. Cardiac vessels stained densely for apelin with negligible staining in myocardial cells. High powered views suggested apelin staining extended to smooth muscle cells also.

The natural ligand for the APJ receptor, apelin, has been isolated from bovine stomach (Tatemoto et al. Biochem Biophys Res Commun., 251:471-6, 1998). Spanning 1726 base pairs of genomic DNA with 3 exons, the apelin locus is highly conserved between species. Apelin is synthesized as a 77 amino acid preprotein that is cleaved to short peptides of different sizes in different tissues (Kawamata et al. Biochim Biophys Acta, 1538:162-71, 2001). Such peptides are collectively referred to as apelin and are named according to their length and/or modification state. In particular, apelin-12 (SEQ ID NO:1) (H-Arg-Pro-Arg-Leu-Ser-His-Lys-Gly-Pro-Met-Pro-Phe-OH), apelin-13 (SEQ ID NO:2) (H-Gln-Arg-Pro-Arg-Leu-Ser-His-Lys-Gly-Pro-Met-Pro-Phe-OH), apelin-17, and apelin-36 (SEQ ID NO:3) (H-Leu-Val-Gln-Pro-Arg-Gly-Ser-Arg-Asn-Gly-Pro-Gly-Pro-Trp-Gln-Gly-Gly-Arg Arg-Lys-Phe-Arg-Arg-Gln-Arg-Pro-Arg-Leu-Ser-His-Lys-Gly-Pro-Met-Pro-Phe-OH) are known to activate APJ. Apelin circulates as pyroglutamylated apelin-13 (SEQ ID NO:4) (Pyr-Arg-Pro-Arg Leu-Ser-His-Lys-Gly-Pro-Met-Pro-Phe-OH), which is believed to be more stable than the other forms. According to various embodiments of the invention any peptide obtained by cleavage of the 77 amino acid preproprotein, or the complete preproprotein, may be used in the methods described herein. Preferably the peptide comprises or consists of apelin-12, apelin-13, or pyroglutamylated apelin-13 (PYR-apelin-13). In certain embodiments of the invention a fragment shorter than 12 amino acids is used, e.g., a subfragment of apelin-12, e.g., a fragment consisting of 6, 7, 8, 9, 10, or 11 continuous amino acids of apelin-12.

APJ is a 377 amino acid, 7 transmembrane domain, $G_i$ coupled receptor whose gene is localized on the long arm of chromosome 11 in humans. It was first cloned in 1993 from genomic human DNA using degenerate oligonucleotide primers (O'Dowd et al. Gene,136:355-60, 1993) and shares significant homology with angiotensin II receptor type 1. Despite this homology however, angiotensin II does not bind APJ. Although "orphan" for many years, the endogenous ligand has been isolated and named apelin (Tatemoto et al. Biochem Biophys Res Commun 251, 471-6 (1998)).

The inventors have studied the effects of both acute and chronic apelin administration. Based on these findings, it is shown that administration of apelin is useful in the treatment of heart failure and related conditions and diseases (including, but are not limited to atherosclerosis, hypertension, restenosis, ischemic cardiovascular diseases, idiopathic or viral cardiomyopathy, diabetes, peripheral arterial disease, etc.). To confirm the ability of apelin to improve cardiovascular function in the setting of heart failure, apelin was administered to animals with experimentally induced heart failure, and their exercise capacity was compared with that of controls that did not receive apelin. Diminished exercise capacity is one of the major symptoms of heart failure, and functional recovery from cardiovascular disease and damage can be assessed by measuring exercise capacity (e.g., using treadmill exercise tests to induce controlled cardiovascular stress). Exercise capacity is a major prognostic indicator in patients with cardiovascular disease, including heart failure, and also in individuals with no history of cardiovascular disease.

The invention provides a method for treating heart failure or a disease or clinical condition associated with heart failure comprising: (i) providing a subject at risk of or suffering from a disease or clinical condition associated with heart failure; and (ii) administering an effective dose of apelin or an APJ receptor ligand to the subject. The invention further provides a method for treating heart failure or a disease or clinical condition associated with heart failure comprising: (i) providing a subject at risk of or suffering from a disease or clinical condition associated with heart failure; and (ii) administering a compound that modulates an endogenous APJ ligand. By "modulate" is meant to enhance or reduce the level or activity of a molecule or to alter the temporal or spatial pattern of its expression or activity, in various embodiments of the invention. For example an agent that acts as an agonist or antagonist at a particular receptor is considered to modulate the receptor. Any of the agents identified by the screening methods of the invention may be used to modulate expression or activity of apelin or the APJ receptor gene expression products and/or ligands for therapeutic or other purposes.

In particular, the invention provides a method of treating heart failure or a disease or condition associated with heart failure comprising the step of administering a compound that increases functional activity of the APJ receptor. One such compound is the apelin-12 peptide. Other suitable compounds include peptides whose sequence comprises the sequence of apelin-12. As mentioned above, a variety of peptides that are cleaved from the apelin precursor in vivo are known and can be used. Such compounds may include modifications, either modifications that take place in vivo or modifications that are introduced by the hand of man. Various modifications that can be made in polypeptides are described above. One preferred compound is Pyr-apelin-13, which is pyroglutamylated apelin and is the predominant form circulating in the body and may be more stable.

Apelin may be administered in any of a variety of ways including subcutaneously, intramuscularly, intravenously, intraperitoneally, inhalationally, etc. Apelin may be administered as a bolus or as a continuous infusion over a period of time. An implantable pump may be used. In certain embodiments of the invention, intermittent or continuous apelin administration is continued for one to several days (e.g., 2-3 or more days), or for longer periods of time, e.g., weeks, months, or years. In some embodiments, intermittent or continuous apelin administration is provided for at least about 3 days. In other embodiments, intermittent or continuous apelin administration is provided for at least about one week. In other embodiments, intermittent or continuous apelin administration is provided for at least about two weeks.

It may be desirable to maintain an average plasma apelin concentration above a particular threshold value either during administration or between administration of multiple doses. A desirable concentration may be determined, for example, based on the subject's physiological condition, disease severity, etc. Such desirable value(s) can be identified by performing standard clinical trials. In certain embodiments of the invention a desirable plasma apelin level is greater than the average normal level (e.g., the average level in normal subjects matched for variables such as age, sex, weight, etc., but not suffering from heart failure) by a factor of at least 2, at least 5, at least 10, at least 20, at least 30, at least 40, at least 50, or more.

It is demonstrated herein that acute administration of apelin in vivo causes a reduction in left ventricular end diastolic area and an increase in left ventricular elastance, whereas chronic apelin infusion increased load independent contractility without increasing left ventricular (LV) mass. These findings demonstrate an important role for the apelin-APJ system in cardiovascular control. Without wishing to be bound by any theory, the inventors hypothesized that apelin would reduce both left ventricular preload and afterload through venous and arterial dilation. The finding that end diastolic area is significantly decreased after intraperitoneal injection of apelin-12 provides the first demonstration that the vascular reactivity of apelin couples to the left ventricle. Decreases in maximum and end systolic pressure were detected in invasive studies, in line with previously observed changes in mean arterial pressure. While not wishing to be bound by any theory, the inventors propose that the significant increase in heart rate is explained by a baroreceptor mediated response to decreased mean arterial pressure. The findings presented herein, i.e., that apelin increases the slope of the end systolic pressure-volume relationship (ventricular elastance), the slope of the end diastolic volume to stroke work relationship and, in the chronic infusion model, the velocity of circumferential shortening, provide the first demonstration of an in vivo effect of apelin on myocardial contractility.

Effecting a reduction in cardiac loading while increasing contractile reserve makes the apelin-APJ system useful for therapy in heart failure. As described herein, increases in the myocardial expression of both apelin and its receptor APJ were observed following LVAD offloading in human heart failure. Further, increases in circulating apelin occur in patients with moderate LV dysfunction. Together, these observations demonstrate that apelin may act as a good peptide in heart failure, serving to ameliorate rather than antagonize the abnormal hemodynamic state of that disease.

Apelin increases contractile reserve through an increase in elastance and concomitantly decreases loading, so does not overdrive the heart. The inventors further demonstrated that no increase in heart or ventricular weight occurs after two weeks of apelin infusion compared to saline control. This is despite increases in cardiac output and in the velocity of circumferential shortening. Apelin is a potent arterial and venous dilator.

The results presented herein describe protein expression of APJ by myocardial cells of the atrium and ventricle for the first time and also identify apelin expression in the coronary endothelium. Without wishing to be bound by any theory, the inventors propose that these data establish a paracrine signaling pathway that links the endothelial cells and myocardial cells for the purpose of regulating cardiac contractility. In addition, the data showing protein and mRNA level expression of apelin and APJ by myocardial cells in the embryonic heart suggest an autocrine pathway that is important for heart development, and which is functional before establishment of the coronary circulation. Since apelin expression by adult myocardial cells was not observed, there appears to be a shift of apelin expression from myocardial to endothelial cells after establishment of the coronary circulation in late gestation. Quantitative evaluation of mRNA levels through late gestation and adulthood indicated that apelin expression is relatively constant, and is consistent with a need to maintain apelin levels for cardiac homeostasis. In decompensated failing human heart tissues apelin immunoreactivity was noted in association with myocardial cells, suggesting that this embryonic pathway is reactivated in the setting of congestive heart failure, in parallel with other embryonic programs.

The experiments described herein establish that administration of apelin results in favorable changes in hemodynamic parameters in normal subjects. Chronic apelin administration resulted in reduced left ventricular preload and afterload, increased contractile reserve, and a significant increase in cardiac output. In addition, the experiments show that chronic apelin administration did not result in hypertrophy, a significant consideration in selecting an appropriate therapy for subjects with heart failure, since cardiac hypertrophy is generally undesirable.

Apelin was also administered by chronic infusion to animals with experimentally induced heart failure. Results showed a marked, statistically significant increase in exercise capacity, the most significant prognostic indicator in human heart failure and a variable that is widely used to assess the severity of cardiovascular disease.

According to certain embodiments of the invention apelin is administered chronically in an amount effective to cause an improvement in at least one clinical symptom, laboratory sign, or diagnostic criterion, of heart failure. By "chronic administration" is meant that the level of apelin (either peak or average plasma level) is maintained above a preselected value for at least 24 hours. In various embodiments of the invention chronic administration refers to a period of at least 36 hours, at least 2 days (48 hours), at least 3 days, at least 4 days, at least 1 week, at least 2 weeks, at least 3 weeks, at least 4 weeks, or longer, e.g., 1 to several months (2, 3, 4, 6 months), years, etc. In various embodiments of the invention the period of chronic administration may be interrupted by one or more periods during which apelin is not administered or is administered at a dose insufficient to reach the predetermined desirable level. However, generally such level would be reached at least 25%, at least 50%, at least 75%, at least 90%, or more of the time over which apelin is administered. In preferred embodiments of the invention apelin is administered chronically in an amount sufficient to cause an improvement in at least one hemodynamic parameter. The improvement can be, for example, a reduction in ventricular preload (e.g., a reduction in left and/or right ventricular preload), a reduction in ventricular afterload (e.g., a reduction in left and/or right ventricular afterload), a decrease in pulmonary artery pressure, an increase in contractile reserve, an increase in cardiac output, an increase in exercise capacity, etc.

Apelin can be administered alone or in combination with any of a variety of other agents used in the treatment of heart failure. A number of such agents are mentioned above and these and other such agents are described in more detail in the scientific literature and in standard texts, for example, in Goodman & Gilman (referenced above) and in Braunwald, et al. (referenced above). By "in combination" is meant that the compounds are administered within a window of time such that they achieve effective concentrations in the body at the same time. The compounds need not be administered at the same time or as components of a single therapeutic composition. In certain embodiments of the invention apelin is administered in combination with BNP. It is noted that an intravenous formulation of BNP (nesiritide) has been approved for treatment of decompensated heart failure in hospital and emergency room settings, and its use in other contexts is being explored (Bhatia, et al; Hobbs, et al.)

The invention provides a variety of pharmaceutical compositions. For example, the invention provides pharmaceutical compositions containing an effective dose of apelin, and a pharmaceutically acceptable carrier. In particular, the invention provides pharmaceutical compositions comprising apelin, e.g., apelin-12, apelin-13, Pyr-apelin-13, and other apelin peptides for the treatment and/or prevention of heart failure or a condition or disease associated with heart failure. The invention further provides pharmaceutical compositions containing nucleic acids or vectors for endogenous expression of such nucleic acids. The invention further provides a pharmaceutical composition comprising an effective amount of an antibody that specifically binds to an apelin or APJ receptor polypeptide and a pharmaceutically acceptable carrier. The invention further provides a pharmaceutical composition comprising an effective amount of a ligand that specifically binds to an apelin or APJ receptor polypeptide, and a pharmaceutically acceptable carrier. The antibodies and ligands may be conjugated with any of the therapeutic moieties discussed above.

Compositions containing antibodies, ligands, conjugates, nucleic acids, vectors for endogenous expression of nucleic acids, peptides, and/or small molecules or other therapeutic agents as described herein may be formulated for delivery by any available route including, but not limited to parenteral (e.g., intravenous), intradermal, subcutaneous, oral (e.g., inhalation), transdermal (topical), transmucosal, rectal, and vaginal. Preferred routes of delivery include parenteral, transmucosal, rectal, and vaginal. Inventive pharmaceutical compositions typically include one or more therapeutic agents, in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. Compositions can also be delivered directly to a site of tissue injury or surgery. They may be administered by catheter or using diagnostic/therapeutic equipment such as bronchoscopes, colonoscopes, etc.

Inventive compositions may also be delivered as implants or components of implantable devices. For example, inventive compositions may be used to coat stents and/or vascular grafts.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive therapeutic agents are preferably delivered in the form of an aerosol spray from pressured container or dispenser which contains a suitable propellant, e.g., a gas such as carbon dioxide, or a nebulizer. It is noted that the lungs provide a large surface area for systemic delivery of therapeutic agents. The agents may be encapsulated, e.g., in polymeric microparticles such as those described in U.S. publication 20040096403, or in association with any of a wide variety of other drug delivery vehicles that are known in the art. In other embodiments of the invention the agents are delivered in association with a charged lipid as described, for example, in U.S. publication 20040062718. It is noted that the latter system has been used for administration of a therapeutic polypeptide, insulin, demonstrating the utility of this system for administration of peptide agents.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fisidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically-effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography, mass spectrometry, etc.

A therapeutically effective amount of a pharmaceutical composition typically ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., one time per week for between about 1 to 10 weeks, between 2 to 8 weeks, between about 3 to 7 weeks, about 4, 5, or 6 weeks, etc. For certain conditions it may be necessary to administer the therapeutic composition on an indefinite basis to keep the disease under control. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with a therapeutic agent as described herein, can include a single treatment or, in many cases, can include a series of treatments.

Exemplary doses include milligram or microgram amounts of the inventive therapeutic agent per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) It is furthermore understood that appropriate doses of a therapeutic agent depend upon the potency of the agent, and may optionally be tailored to the particular recipient, for example, through administration of increasing doses until a preselected desired response is achieved. It is understood that the specific dose level for any particular animal subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

Inventive pharmaceutical compositions can be included in a container, pack, or dispenser together with instructions for administration.

The discovery that apelin or APJ receptor genes are regulated upon mechanical offloading in heart failure provides motivation for the production of antibodies that bind to the encoded polypeptides. Such antibodies are useful for a variety of purposes including diagnostic, therapeutic, as targeted delivery vehicles or components of such vehicles, for research purposes, etc. The invention provides an antibody that specifically binds to an apelin or APJ receptor polypeptide.

According to certain embodiments of the invention the antibodies are polyclonal antibodies, however in preferred embodiments of the invention they are monoclonal antibodies. Generally applicable methods for producing antibodies are well known in the art and are described extensively in references cited above. It is noted that antibodies can be generated by immunizing animals (or humans) either with a full length polypeptide, a partial polypeptide, fusion protein, or peptide (which may be conjugated with another moiety to enhance immunogenicity). The specificity of the antibody will vary depending upon the particular preparation used to immunize the animal and on whether the antibody is polyclonal or monoclonal. For example, if a peptide is used the resulting antibody will bind only to the antigenic determinant represented by that peptide. It may be desirable to develop and/or select antibodies that specifically bind to particular regions of the polypeptide, e.g., the extracellular domain. Such specificity may be achieved by immunizing the animal with peptides or polypeptide fragments that correspond to that region. Alternately, a panel of monoclonal antibodies can be screened to identify those that specifically bind to the desired region. The invention therefore provides a panel of antibodies for polypeptides encoded by each upregulated or downregulated gene, wherein each member of the panel specifically recognizes a different antigenic determinant present in the polypeptide.

In general, certain preferred antibodies will possess high affinity, e.g., a $K_d$ of <200 mM, and preferably, of <100 mM for their target. According to certain embodiments of the invention preferred antibodies do not show significant reactivity with normal tissues other than the heart, e.g., tissues of key importance such as kidney, brain, liver, bone marrow, colon, breast, prostate, thyroid, gall bladder, lung, adrenals, muscle, nerve fibers, pancreas, skin, etc. In the context of reactivity with tissues, the term "significant reactivity", as used herein, refers to an antibody or antibody fragment, which, when applied to a tissue of interest under conditions suitable for immunohistochemistry, will elicit either no staining or negligible staining, e.g., only a few positive cells scattered among a field of mostly negative cells.

The invention provides various methods of using the antibodies described above. For example, the antibodies may be used to perform immunohistochemical analysis, immunoblotting, ELISA assays, etc., in order to detect the polypeptide to which the antibody specifically binds. In the case of polypeptides that are released into the bloodstream, detection of the polypeptide in a blood sample can provide a diagnostic test for heart failure, as described further below. The antibodies may be used as components of antibody arrays. The antibodies may also be used for imaging studies, as described further below. In addition, the antibodies are useful for delivering attached moieties to target cells in the heart, as a component in a targeted delivery vehicle, and as therapeutic agents.

In another aspect, the invention provides ligands that specifically bind to an apelin or APJ receptor polypeptide. The term "ligand" is intended to encompass any type of molecule other than antibodies as described above. Ligands may be, for example, peptides, non-immunoglobulin polypeptides, nucleic acids, protein nucleic acids (PMAs), aptamers, small molecules, etc. Ligands that specifically bind to an apelin or APJ receptor polypeptide described herein may be identified using any of a variety of approaches. For example, ligands may be identified by screening libraries, e.g., small molecule libraries. Naturally occurring or artificial (non-naturally occurring) ligands, particularly peptides or polypeptides, may be identified using a variety of approaches including, but not limited to, those known generically as two- or three-hybrid screens, the first version of which was described in Fields S, and Song O., Nature Jul. 20 1989; 340(6230):245-6. Nucleic acid or modified nucleic acid ligands may be identified using, e.g., systematic evolution of ligands by exponential enrichment (SELEX) (Tuerk et al. Science 249(4968): 505-10, 1990), or any of a variety of directed evolution techniques that are known in the art. See also Jellinek et al., Biochemistry, 34(36): 11363-72, 1995, describing identification of high-affinity 2'-aminopyrimidine RNA ligands to basic fibroblast growth factor (bFGF). Screens using nucleic acids, peptides, or polypeptides as candidate ligands may utilize nucleic acids, peptides, or polypeptides that incorporate any of a variety of nucleotide analogs, amino acid analogs, etc. Various nucleotide analogs are known in the art, and other modifications of a nucleic acid chain, e.g., in the backbone, can also be used, as described elsewhere herein.

Peptides or polypeptides may incorporate one or more unnatural amino acids (e.g., amino acids that are not naturally found in mammals, or amino acids that are not naturally found in any organism). Such amino acids include, but are not limited to, cyclic amino acids, diamino acids, .beta.-amino acids, homo amino acids, alanine derivatives, phenylalanine boronic acids, proline and pyroglutamine derivatives, etc. Alterations and modifications may include the replacement of an L-amino acid with a D-amino acid, or various modifications including, but not limited to, phosphorylation, carboxylation, alkylation, methylation, etc.

Polypeptides incorporating unnatural amino acids may be produced either entirely artificially or through biological processes, e.g., in living organisms. Use of unnatural amino acids may have a number of advantages. For example, unnatural amino acids may be utilized as building blocks, conformational constraints, molecular scaffolds, or pharmacologically active products. They represent a broad array of diverse structural elements that may be utilized, e.g., for the development of new leads in peptidic and non-peptidic compounds. They may confer desirable features such as enhanced biological activity, proteolytic resistance, etc. See, e.g., Bunin, B. A. et al., Annu. Rep. Med. Chem. 1999, 34, 267; Floyd, C. D. et al., Prog. Med. Chem. 1999, 36, 91; Borman, S. Chem. Eng. News 1999, 77, 33; Brown, R. K. Modern Drug Discovery 1999, 2, 63; and Borman, S. Chem. Eng. News 2000, 78, 53, describing various applications of unnatural amino acids. Once a ligand is identified, modifications such as those described above may be made.

In general, a screen for a ligand that specifically binds to an apelin or APJ receptor polypeptide may comprise steps of contacting an apelin or APJ receptor polypeptide with a candidate ligand under conditions in which binding can take place; and determining whether binding has occurred. Any appropriate method for detecting binding, many of which are well known in the art, may be used. One of ordinary skill in the art will be able to select an appropriate method taking into consideration, for example, whether the candidate ligand is a small molecule, peptide, nucleic acid, etc. For example, the candidate ligand may be tagged, e.g., with a radioactive molecule. The apelin or APJ receptor polypeptide can then be isolated, e.g., immunoprecipitated from the vessel in which the contacting has taken place, and assayed to determine whether radiolabel has been bound. This approach may be particularly appropriate for small molecules. Binding can be confirmed by any of a number of methods, e.g., plasmon resonance assays. Phage display represents another method for the identification of ligands that specifically bind to apelin or APJ receptor polypeptides. In addition, determination of the three-dimensional structure of an apelin or APJ receptor polypeptide (e.g., using nuclear magnetic resonance, X-ray crystallography, etc.) may facilitate the design of appropriate ligands.

Functional assays may also be used to identify ligands, particularly ligands that behave as agonists or antagonists, activators, or inhibitors of particular polypeptides. For such assays it is necessary that the polypeptide of interest possesses a measurable or detectable functional activity and that such functional activity is increased or decreased upon binding of the ligand. Examples of functional activities of a polypeptide include, e.g., ability to catalyze a chemical reaction either in vitro or in a cell, ability to induce a change of any sort in a biological system, e.g., a change in cellular phenotype, a change in gene transcription, a change in membrane current, a change in intracellular or extracellular pH, a change in the intracellular or extracellular concentration of an ion, etc. when present within a cell or when applied to a cell.

Ligands that bind to apelin or APJ receptor polypeptides have a variety of uses, which are described below. For example, they may serve as components of targeted delivery vehicles and can be used for imaging of the heart. Ligands that modulate the expression and/or activity of an apelin or APJ receptor polypeptide can also be used for therapeutic purposes.

Certain of the methods for identifying ligands may be performed in vitro, e.g., using an apelin or APJ receptor polypeptide or a significantly similar polypeptide or fragment thereof produced using recombinant DNA technology. Certain of the methods may be performed by applying the test compound to a cell that expresses the polypeptide and measuring the expression or activity of the polypeptide, which may involve isolating the polypeptide from the cell and subsequently measuring its amount and/or activity. In certain of the methods the polypeptide may be a variant that includes a tag (e.g., an HA tag, 6×His tag, Flag tag, etc.) which may be used, for example, to facilitate isolation or the variant may be a fusion protein.

In general, an appropriate method for measuring activity of a polypeptide will vary depending on the polypeptide. For example, if the polypeptide has a known biological or enzymatic activity, or is homologous to a polypeptide with a known biological or enzymatic activity, that activity will be measured using any appropriate method known in the art. Thus if the polypeptide is a kinase a kinase assay will be performed. If the molecule is a cytokine, biological assays such as the ability to activate and/or trigger migration of other cell types can be assessed. If the molecule is a growth factor or growth factor receptor, the ability of the polypeptide to cause cell proliferation can be assessed.

Compounds suitable for screening according to the above methods include small molecules, natural products, peptides, nucleic acids, etc. Sources for compounds include natural product extracts, collections of synthetic compounds, and compound libraries generated by combinatorial chemistry. Libraries of compounds are well known in the art. One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening. For descriptions of additional libraries, see, for example, Tan, et al., Am. Chem. Soc. 120, 8565-8566, 1998; Floyd C D, Leblanc C, Whittaker M, Prog Med Chem 36:91-168, 1999. Numerous libraries are commercially available, e.g., from AnalytiCon-USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. In certain embodiments of the invention the methods are performed in a high-throughput format using techniques that are well known in the art, e.g., in multiwell plates, using robotics for sample preparation and dispensing, etc. Representative examples of various screening methods may be found, for example, in U.S. Pat. Nos. 5,985,829, 5,726,025, 5,972,621, and 6,015,692. The skilled practitioner will readily be able to modify and adapt these methods as appropriate.

Molecular modeling can be used to identify a pharmacophore for a particular target, i.e., the minimum functionality that a molecule must have to possess activity at that target. Such modeling can be based, for example, on a predicted structure for the target (e.g., a two-dimensional or three-dimensional structure). Software programs for identifying such potential lead compounds are known in the art, and once a compound exhibiting activity is identified, standard methods may be employed to refine the structure and thereby identify more effective compounds.

Thus the invention provides a method for screening for a ligand for an apelin or APJ receptor polypeptide comprising steps of: (i) providing a sample comprising an apelin or APJ receptor polypeptide; (ii) contacting the sample with a candidate compound; (iii) determining whether the level of activity of the polypeptide in the presence of the compound is increased or decreased relative to the level of activity of the polypeptide in the absence of the compound; and (iv) identifying the compound as a ligand of the apelin or APJ receptor polypeptide if the level of activity of the apelin or APJ receptor polypeptide is higher or lower in the presence of the compound relative to its level of activity in the absence of the compound. In certain embodiments of the method the sample comprises cells that express the apelin or APJ receptor polypeptide. Identified compounds can be further tested in vitro or in vivo. For example, it may be desirable to include an additional step of (v) administering the compound to an animal suffering from heart failure and evaluating the response. Response can be evaluated in any of a variety of ways, e.g., by assessing clinical features, laboratory data, images, etc.

According to certain of the inventive screening methods for identifying activators or inhibitors of APJ, the APJ polypeptide is expressed in cells. In general, a wide variety of cells can be used, e.g., Xenopus oocytes, yeast cells, mammalian cells, etc. Numerous different types of mammalian cell lines are suitable, e.g., CHO cells, HEK293 cells, L cells, BHK cells, etc. Primary cells, e.g., cardiac myocytes, can also be used. Candidate compounds are applied to the cells and the intracellular or extracellular pH is detected. An increase in the intracellular pH or a decrease in the extracellular pH (e.g., acidification of the fluid in which the cells are contained) indicates that the candidate compound activates the APJ receptor, leading to an activation of the $Na^+/H^+$ exchanger, which causes an increase in proton flux across the cell membrane, leading to an increase in intracellular pH and a decrease in extracellular pH. pH can be detected using any available means. One convenient method of detecting a change in extracellular pH is to include a pH-sensitive indicator molecule in the fluid containing the cells, e.g., phenol red, bromocresol purple, etc. A property of the molecule such as color, fluorescence, etc., of the dye serves as an indication of the pH. The intracellular pH can be deleted in an analogous manner by loading cells with an appropriate pH-sensitive molecule. Such assays are well known in the art. Use of an imaging system to detect changes in fluorescence, color, etc., facilitates adaptation of the assay to high throughput screening techniques. Devices such as the Cytosensor (Molecular Devices, Sunnyvale, Calif.) may also be used to measure extracellular pH and/or extracellular acidification rate as described in Tatemoto, et al, referenced above.

As mentioned above, activation of the APJ receptor also results in activation of the $Na^+/Ca^{++}$ exchanger operating in reverse mode, leading to increased intracellular $Ca^{++}$ concentration and a corresponding decrease in extracellular $Ca^{++}$ concentration. Methods for identifying agents that cause increased intracellular $Ca^{++}$ and/or decreased extracellular $Ca^{++}$ are well known in the art and can be used to identify compounds that activate the APJ receptor. For example, membrane $Ca^{++}$ current can be measured. Alternately, flux of $Ca^{++}$ isotopes can be detected. Perhaps the most widely used method of monitoring $Ca^{++}$ is by the use of fluorescent $Ca^{++}$ indicators (Tsien, R. in Methods in Cell Biology, Vol. 30, Taylor, D. L. and Wang, Y-L, Eds., Academic Press (1989) pp. 127-156). These indicators are used to detect $Ca^{++}$ concentration via their fluorescent spectral changes upon $Ca^{++}$ binding. Any of a variety of $Ca^{++}$ indicators, including Fura-2, Indo-1, Fluo-3 and Rhod-2, and related molecules, can be used to monitor changes in $Ca^{++}$ concentration, which serves to identify agents that activate APJ. An example of the use of Fura 2-AM to measure intracellular $Ca^{++}$ concentration and of the use of $^{45}Ca^{++}$ to measure $Ca^{++}$ in cardiac myocytes is found in Pei, 30 J-M., et al., Am. J. Physiol. Cell Physiol., 285: C1420-1428, 2003.

Compounds that inhibit rather than activate the APJ receptor may be identified using modifications of the assays described above. According to one method, in the absence of an inhibitor, contacting cells that express the APJ receptor with a known activating ligand such as apelin causes an increase in intracellular pH, acidification of the extracellular fluid, and an increase in intracellular $Ca^{++}$. However, in the presence of a compound that inhibits the activity of the APJ receptor (which includes inhibition by blocking access by a ligand) or decreases its expression, the extent to which a given amount of apelin will cause increased acidification of extracellular fluid, increased intracellular pH, increased proton flux, increased intracellular $Ca^{++}$, or decreased extracellular $Ca^{++}$, or increased $Ca^{++}$ flux, will be diminished compared with the effect that would result in the absence of the inhibitory compound. Compounds that exert such an inhibitory, or blocking effect, i.e., compounds that antagonize the effects of known APJ activators, are identified as APJ inhibitors. Analogous methods may be employed to identify inhibitors of other proteins with measurable biochemical activities and known ligands.

Another method that can be of particular use to identify non-peptidic modulators of peptides or their receptors involves a two-tier screening strategy (e.g., of a small molecule library) in which the first screening entails disruption of the interaction between the peptide and a neutralizing monoclonal antibody. Selected compounds are then further characterized by their ability to modulate second messengers in cells containing specific receptors. Binding of the identified small molecules to immobilized peptide (or receptor) may be demonstrated by surface plasmon resonance assays, etc. This strategy has been successfully employed to identify modulators of adrenomedullin and gastrin-releasing peptide (Martinez, A., et al., Identification of Vasoactive Non-Peptidic Positive and Negative Modulators of Adrenomedullin Using a Neutralizing Antibody-Based Screening Strategy, Endocrinology, April 2003).

In general, a wide variety of different compounds can be screened. Numerous libraries of natural products, synthetic molecules, combinatorial libraries, etc., are known in the art, and any of these can be used, as mentioned above. In addition, the assays can be used to test variants of known ligands such as apelin peptides in the case of the APJ receptor. Apelin may be used as a starting material to design ligands with improved affinity, bioavailability, etc. Molecular modeling can be used to identify a pharmacophore for APJ, as described above.

The invention further provides a variety of delivery vehicles targeted to cardiac cells using antibodies and/or ligands that specifically bind to apelin or APJ receptor polypeptides. In general, delivery vehicles are employed to improve the ability of an active molecule to achieve its desired effect on a cell, tissue, organ, subject, etc., e.g., by increasing the likelihood that the active agent will reach its site of activity. By "delivery vehicle" is meant a natural or artificial substance that is physically associated with an active molecule and provides one or more of the following functions among others: (1) conveys an active molecule within the body; (2) facilitates the uptake of an active molecule by cells, tissues, organs, etc.; (3) increases stability of an active molecule, e.g., increases half-life of the molecule; (4) changes other pharmacokinetic properties of the active molecule from what they would have been in the absence of the delivery vehicle. The active molecule may be associated with the delivery vehicle in any of a number of ways. For example, the active molecule may be bonded to the delivery vehicle (e.g., via covalent or hydrogen bonds). In certain preferred embodiments of the invention the active molecule is dispersed within or encapsulated within the delivery vehicle. By "dispersed within" is meant that individual molecules of the active molecule are intermingled with molecules comprising the material from which the delivery vehicle is made as opposed, for example, to being present as a discrete cluster of molecules.

Preferred targeting agents for use in targeting bind to an apelin or APJ receptor polypeptide or portion thereof that is expressed on the surface of a cardiac cell, e.g., a cardiac myocyte or cardiac endothelial cell. According to the invention antibodies or ligands are incorporated in and/or linked to the delivery vehicle for targeting to cardiac cells. Typically at least the portion of the antibody or ligand that binds to the apelin or APJ receptor polypeptide is present on the surface of the delivery vehicle, while the molecule to be delivered is typically inside. Viral vectors can be engineered to express such binding portions, peptide or polypeptide ligands, etc. Immunoliposomes (antibody-directed liposomes) can also be used. See, e.g., Bendas, G., "Immunoliposomes: a promising approach to targeting cancer therapy", BioDrugs, 15(4), 215-24, 2001. It is noted that such targeted delivery vehicles may be used for the delivery of a wide variety of agents to cardiac cells. Typically the agent is contained within the liposome's aqueous cavity or is one of the components in its lipid membrane.

The invention further provides a targeting agent, e.g., an antibody or ligand that specifically binds to an apelin or APJ receptor polypeptide, wherein the targeting agent is conjugated to a support. The support can be, for example, a nanosphere, microsphere, or bead. The support can be made out of any of a variety of materials including, but not limited to, agarose, polyacrylamide, nylon, dextran, polyethylene glycol, polysaccharides such as PLA, PLGA or chitosan, other polymers, etc. Such conjugates are useful, for example, for detecting, isolating, or purifying apelin or APJ receptor polypeptides. These conjugates may also serve as delivery vehicles for an apelin or APJ receptor antibody or ligand. According to one approach, the antibodies or ligands of the invention can be conjugated to nanoparticles, which may incorporate moieties such as therapeutic agents or agents useful for imaging, as described, for example, in as described in Li, et al., J. Cell. Biochem. Suppl., 39:65-71, 2002. In addition, the invention provides targeting agents that specifically bind to apelin or APJ receptor polypeptides, wherein the targeting agents are conjugated to a support, and wherein an additional moiety is conjugated to the support. The additional moiety may be, for example, a therapeutic agent, an imaging agent, a readily detectable marker, an enzyme, etc.

In another aspect, the invention provides compositions comprising a targeting agent linked with a functional moiety, wherein the targeting agent specifically binds to an apelin or APJ receptor polypeptide. Targeting agents may be any agent that specifically binds to an apelin or APJ receptor polypeptide. In particular, targeting agents can be antibodies or ligands that specifically bind to an apelin or APJ receptor polypeptide, as described above.

In general, these compositions possess at least two functions, one of which is specifically binding to an apelin or APJ receptor polypeptide. The antibody may be any of the antibodies described above that bind to apelin or APJ receptor polypeptides. By "functional moiety" is meant any compound, agent, molecule, etc., that possesses an activity or property that alters, enhances, or otherwise changes the ability of the targeting agent to fulfill any particular purpose or that enables the targeting agent to fulfill a new purpose. Such purposes include, but are not limited to, providing diagnostic and/or prognostic information and/or treatment of diseases or conditions associated with heart failure, or imaging the heart.

By "linked" is generally meant covalently bound or, if noncovalently bound, physically associated via intermolecular forces approximately equal in strength to that of covalent bonds. Thus a noncovalent interaction between two molecules that has very slow dissociation kinetics can function as a link. For example, an antibody associated with its cognate antigen is generally considered linked. As another example, reactive derivatives of phospholipids can be used to link the liposomes or cell membranes in which they are incorporated to antibodies or enzymes. Targeting agents, e.g., antibodies or ligands linked with a functional moiety will be referred to herein as conjugates or heteroconjugates. According to certain embodiments of the invention the functional moiety is a compound (e.g., polyethylene glycol) that stabilizes the targeting agent and/or increases its resistance to degradation.

According to certain embodiments of the invention the targeting agent is synthesized using precursors, e.g., amino acids, that contain the functional moiety. For example, an antibody or a polypeptide ligand can be synthesized using amino acid precursors that contain flourine-19 instead of hydrogen at one or more positions, or that contain nitrogen-15 or oxygen-17 instead of the more abundant isotope at one or more positions. As a second example, where the functional moiety is a polypeptide, the composition may be produced as a fusion protein, as described above, wherein one portion of the fusion protein (the antibody or ligand) specifically binds to an apelin or APJ receptor polypeptide and a second portion of the fusion protein consists of or comprises a functional moiety. Alternately, polypeptides may be modified to incorporate a functional moiety. For example, the methods described in Haruta, Y., and Seon, B. K., Proc. Nat. Acad. Sci., 83, 7898-7902 (1986) may be used to iodinate antibodies and other polypeptides. See also Tabata, M., et al., Int. J Cancer, Vol. 82, Issue 5: 737-742, 1999. Functional moieties incorporated into a targeting agent of the invention during synthesis or added to the antibody or ligand subsequently are considered "linked" to the targeting agent.

Functional moieties may be linked to targeting agents such as antibodies by any of a number of methods that are well known in the art. Examples include, but are not limited to, the glutaraldehyde method which couples primarily through the .alpha.-amino group and &-amino group, maleimide-sulfhydryl coupling chemistries (e.g., the maleimidobenzoyl-N-hydroxysuccinimide ester (MBS) method), and periodate oxidation methods, which specifically direct the coupling location to the Fc portion of the antibody molecule. In addition, numerous cross-linking agents are known, which may be used to link the targeting agent to the functional moiety.

A wide variety of methods (selected as appropriate taking into consideration the properties and structure of the ligand and functional moiety) may likewise be used to produce the ligand-functional moiety conjugates of the invention. Suitable cross-linking agents include, e.g., carboiimides, N-Hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), etc. According to certain embodiments of the invention the functional moiety is a compound (e.g., polyethylene glycol) that stabilizes the ligand and/or increases its resistance to degradation.

For additional information on conjugation methods and crosslinkers see generally the journal Bioconjugate Chemistry, published by the American Chemical Society, Columbus Ohio, PO Box 3337, Columbus, Ohio, 43210. This journal reports on advances concerning the covalent attachment of active molecules to biopolymers, surfaces, and other materials. Coverage spans conjugation of antibodies and their fragments, nucleic acids and their analogs, liposomal components, and other biologically active molecules with each other or with any molecular groups that add useful properties. Such molecular groups include small molecules, radioactive elements or compounds, polypeptides, etc. See also "Cross-Linking", Pierce Chemical Technical Library, available at the Web site having URL www.piercenet.com and originally published in the 1994-95 Pierce Catalog and references cited therein and Wong S S, Chemistry of Protein Conjugation and Crosslinking, CRC Press Publishers, Boca Raton, 1991. The following section presents a number of examples of specific conjugation approaches and cross-linking reagents. However, it is to be understood that the invention is not limited to these methods, and that selection of an appropriate method may require attention to the properties of the particular functional moiety, substrate, or other entity to be linked to the targeting agent.

According to certain embodiments of the invention a bifunctional crosslinking reagent is used to couple a functional moiety with a targeting agent of the invention. In general, bifunctional crosslinking reagents contain two reactive groups, thereby providing a means of covalently linking two target groups. The reactive groups in a chemical crosslinking reagent typically belong to the classes of functional groups—including succinimidyl esters, maleimides, and iodoacetamides. Bifunctional chelating agents may also be used. For example, a targeting agent of the invention may be coupled with a chelating agent, which may be used to chelate a functional moiety such as a metal. Bifunctional chelating agents may be used to couple more than one functional moiety to a targeting agent of the invention. For example, according to certain embodiments of the invention one or more of the functional moieties is useful for imaging and/or one or more of the functional moieties is useful for therapy. Appropriate chelating agents for use with the antibodies or ligands of the invention include polyaminocarboxylates, e.g.; DTPA, macrocyclic polyaminocarboxylates such as 1,4,7,10-tetraazacyclododecane N,N',N'',N'''-tetraacetic acid (DOTA), etc. See Lever, S., J. Cell. Biochem. Suppl., 39:60-64, 2002, and references therein.

The most common schemes for forming a heteroconjugate involve the indirect coupling of an amine group on one biomolecule to a thiol group on a second biomolecule, usually by a two- or three-step reaction sequence. The high reactivity of thiols and their relative rarity in most biomolecules make thiol groups good targets for controlled chemical crosslinking. If neither molecule contains a thiol group, then one or more can be introduced using one of several thiolation methods. The thiol-containing biomolecule may then be reacted with an amine-containing biomolecule using a heterobifunctional crosslinking reagent, e.g., a reagent containing both a succinimidyl ester and either a maleimide or an iodoacetamide. Amine-carboxylic acid and thiol-carboxylic acid crosslinking may also be used. For example, 1-Ethyl-3-(3-dimethylaminopro-pyl)carbodiimide (EDAC) can react with biomolecules to form "zero-length" crosslinks, usually within a molecule or between subunits of a protein complex. In this chemistry, the crosslinking reagent is not incorporated into the final product. The water-soluble carbodiimide EDAC crosslinks a specific amine and carboxylic acid between subunits of allophycocyanin, thereby stabilizing its assembly. See, e.g., Yeh S-W, et al., "Fluorescence properties of allophycocyanin and a crosslinked allophycocyanin trimer.", Cytometry 8, 91-95 (1987).

Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Tryptophan residues in thiol-free proteins can be oxidized to mercaptotryptophan residues, which can then be modified by iodoacetamides or maleimides Reagents used to crosslink liposomes, cell membranes and potentially other lipid assemblies to biomolecules typically comprise a phospholipid derivative to anchor one end of the crosslink in the lipid layer and a reactive group at the other end to attach the membrane assembly to the target biomolecule.

For purpose of covalently linking active molecules (e.g., therapeutic agents) to targeting agents, it may be preferred to select methods that result in a conjugate wherein the targeting agent is separable from the toxin to allow the toxin to enter the cell. Thiol-cleavable, disulfide-containing conjugates may be employed for this purpose. Cells are able to break the disulfide bond in the cross-linker, which permits release of the toxin within the target cell. Examples of suitable cross-linkers include 2-Iminothiolane (Traut's reagent), N-succinimidyl 3-(2-pyridyldithio)propionate (SPDP), etc. In addition, it is generally preferable to select methods that do not significantly impair the ability of the targeting agent to specifically bind to its target and do not significantly impair the ability of the functional moiety to perform its intended function. One of ordinary skill in the art will be able to test the conjugate to determine whether the targeting agent retains binding ability and/or whether the functional moiety retains its function. According to certain embodiments of the invention the functional moiety is released from the targeting agent upon uptake into the cell. For example, the functional moiety may be attached to the targeting agent via a linker or spacer that is cleaved by an intracellular enzyme.

According to certain embodiments of the invention the functional moiety is one that causes, either directly or indirectly, a change in the physiological (i.e., functional) and/or biochemical state of a cell with which it comes into contact. In general, a change in the physiological state of a cell will involve multiple biochemical changes. By "directly causing" is meant that the functional moiety either causes the change itself or by interacting with one or more cellular or extracellular constituents (e.g., nucleic acid, protein, lipid, carbohydrate, etc.) not introduced or induced by the hand of man. The category of direct causation includes instances in which the functional moiety initiates a "pathway", e.g., in which the functional moiety interacts with one or more constituents, which causes a change in the interaction(s) of this constituent with other constituents, ultimately leading to the alteration in physiological or biochemical state of the cell. By "indirectly causing" is meant either (i) that the functional moiety itself does not cause the change but must be converted into an active form (e.g., by a cellular enzyme) in order to cause the change; or (ii) that the functional moiety itself does not cause the change but instead acts on a second agent that causes the change, which second agent is also introduced to or induced in the cell, its surface, or vicinity by the hand of man.

Various examples of changes in physiological or biological state include, but are not limited to, increases or decreases in gene expression (e.g., increases or decreases in transcription, translation, and/or mRNA or protein turnover), alterations in subcellular localization or secretion of a cellular constituent, alteration in cell viability or growth rate, alteration in differentiation state, etc. According to certain embodiments of the invention the functional moiety is a growth stimulatory or inhibitory agent. For example, the functional moiety may comprise or encode a growth factor, a growth factor receptor, or an agonist or antagonist of a growth factor receptor, wherein the growth factor, growth factor receptor, growth factor receptor agonist, or growth factor receptor antagonist stimulates or inhibits growth or division of cardiac cells, and wherein presence of the growth factor receptor in or on the surface of cardiac cells, e.g., cardiac myocytes or cardiac endothelial cells may either stimulate or inhibit its growth or division depending at least in part on the presence of agonists or antagonists.

Whether any particular functional moiety stimulates or inhibits growth and/or division of cardiac cells may readily be tested either using in vitro tissue culture systems in which cardiac cells are contacted with the functional moiety is and their growth and/or division is then measured, or in vivo, in either animals or humans. In the latter case, the ability of the moiety to stimulate or inhibit growth and/or division of cardiac cells may be assessed using, for example, various imaging techniques (see below), or by taking samples of cardiac tissue and assessing its proliferative state (e.g., by determining the mitotic index, measuring expression or activity of proteins associated with cell division, etc.).

According to certain embodiments of the invention the functional moiety is a nucleic acid, which may serve as a template for a transcript to be expressed in the cell. The transcript may encode a polypeptide to be expressed within the cell.

As described above, the invention provides a composition comprising a targeting agent linked to a functional moiety, wherein the targeting agent specifically binds to an apelin or APJ receptor polypeptide. According to certain embodiments of the invention the functional moiety is a readily detectable moiety. In general, a readily detectable moiety has a property such as fluorescence, chemiluminescence, radioactivity, color, magnetic or paramagnetic properties, etc., which property renders it detectable by instruments that detect fluorescence, chemiluminescence, radioactivity, color, or magnetic resonance, etc. Alternately, a readily detectable moiety may comprise or encode an enzyme that acts on a substrate to produce a readily detectable compound. According to certain embodiments of the invention the readily detectable moiety is one that, when present at a target site subsequent to administration of the inventive composition to a subject, can be detected from outside the body. In certain preferred embodiments of the invention the readily detectable moiety can be detected non-invasively.

A variety of different moieties suitable for imaging (e.g., moieties suitable for detection by X-ray, fluoroscopy, computed tomography, magnetic resonance imaging, positron emission tomography, gamma tomography, electron spin resonance imaging, optical or fluorescence microscopy, etc.) can be used. Such agents are referred to herein as "imaging agents". Imaging agents include, but are not limited to, radioactive, paramagnetic, or supraparamagnetic atoms (or molecules containing them). Suitable radioactive atoms include technetium-99m, thallium-211, iodine-133; atoms with magnetic moments such as iodine-123, iodine-131, indium-111, fluorine-19, carbon-13, nitrogen-15, oxygen-17, gadolinium, manganese, or iron. Other suitable atoms include rhenium-186 and rhenium-188. Useful paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), europium, and erbium (III), with gadolinium being particularly preferred. Gd-chelates, e.g., DTPA chelates, may be used. For example, the water soluble Gd(DTPA).sup.2-chelate, is one of the most widely used contrast enhancement agents in experimental and clinical imaging research. The DTPA chelating ligand may be modified, e.g., by appending one or more functional groups preferably to the ethylene diamine backbone. Ions useful in other contexts, such as X-ray imaging, include but are not limited to lanthanum (III), gold (III), lead (II), and bismuth (III). Additional moieties useful for imaging include gallium-67, copper-67, yttrium-90, and astatine-211. Moieties useful for optical or fluorescent detection include fluorescein and rhodamine and their derivatives. Agents that induce both optical contrast and photosensitivity include derivatives of the phorphyrins, anthraquinones, anthrapyrazoles, perylenequinones, xanthenes, cyanines, acridines, phenoxazines and phenothiazines (Diwu, Z. J. and Lown, J. W., Pharmacology and Theraeutics 63: 1-35, 1994; Grossweiner, L. I., American Chemical Society Symposium. Series 559: 255-265, 1994). Further information regarding methods and applications of molecular imaging in contexts including basic research, diagnosis, therapeutic monitoring, drug development, etc., may be found in articles appearing in the Journal of Cellular Biochemistry, Volume 87, Issue S39 (Supplement), 2002.

The readily detectable moiety may be linked to the targeting agent using various methods as described above. It is noted that many of these moieties may also be useful for therapeutic applications. See, e.g., U.S. Pat. Nos. 5,021,236 and 4,472,509, for various diagnostic agents known in the art to be useful for imaging purposes and methods for their attachment to antibodies. See also discussion above describing coupling of antibodies and ligands of the invention with functional moieties.

According to certain embodiments of the invention the functional moiety is able to bind to an additional moiety, which may impart additional functions. For example, the functional moiety may be a bispecific antibody, one portion of which binds to an apelin or APJ receptor polypeptide and another portion of which binds to a second molecule, e.g., another functional moiety. Alternately, a second molecule may be linked covalently to the functional moiety.

Accordingly, the invention provides a method of imaging cardiovascular tissue in a sample or subject, comprising steps of: (i) administering to the sample or subject an effective amount of a targeting agent that specifically binds to an apelin or APJ receptor polypeptide, wherein the targeting agent is linked to a functional moiety that enhances detectability of cardiac cells by an imaging procedure; and (ii) subjecting the sample or subject to the imaging procedure. The targeting agent may be, for example, an antibody or ligand that specifically binds to the polypeptide. The methods are useful for imaging the heart for any of a wide variety of purposes. In general, the level of expression of the apelin or APJ receptor polypeptide will be reflected in a characteristic of the image such as intensity. The level of expression can be useful in diagnosing disease (e.g., heart failure and related conditions), assessing disease severity, and/or monitoring the course of the disease or response to treatment. Appropriate imaging procedures include, but are not limited to, X-ray, fluoroscopy, computed tomography, magnetic resonance imaging, positron emission tomography and variants thereof such as SPECT or CT-PET, gamma tomography, electron spin resonance imaging, optical or fluorescence microscopy, etc.

In the case of certain of the apelin or APJ receptor genes identified herein, this work provides the first evidence that these genes are expressed in cardiac tissue. Imaging the expression of these genes will be useful for purposes unrelated to assessing risk or severity of heart failure, response to treatment for heart failure, etc. For example, the fact that these genes are expressed in cardiac tissue indicates that detecting their expression, e.g., by means of imaging, will allow visualization of cardiac tissues for purposes such assessing cardiac structure, assessing the functional capacity of the heart, etc.

Since the apelin or APJ receptor R genes are therapeutic targets for heart failure, it is desirable to be able to modulate their expression and/or activity, both for therapeutic and other purposes. The invention therefore provides a variety of methods for altering expression and/or functional activity. The invention encompasses methods for screening compounds for preventing or treating heart failure or a disease or clinical condition associated with heart failure by assaying the ability of the compounds to modulate the expression of the apelin or APJ receptor genes, or activity of the protein products of these genes. Appropriate screening methods include, but are not limited to, assays for identifying compounds and other substances that interact with (e.g., bind to) the target gene protein products.

The various nucleic acids described above may be delivered to a subject using any of a variety of approaches, including those applicable to non-nucleic acid agents such as IV, intranasal, oral, etc. However, according to certain embodiments of the invention the nucleic acids are delivered via a gene therapy approach, in which a construct capable of directing expression of one or more of the inventive nucleic acids is delivered to cells or to the subject (ultimately to enter cells, where transcription may occur). Thus according to certain embodiments of the invention the vectors described above include gene therapy vectors appropriate for the delivery of a construct that directs expression of a polypeptide, variant, fragment, etc. to mammalian cells, more preferably cells of a domesticated mammal, and most preferably human cells. A variety of gene therapy vectors are known in the art. Suitable gene therapy vectors include viral vectors such as adenoviral or adeno-associated viral vectors, retroviral vectors and lentiviral vectors. In certain instances lentiviruses may be preferred due, e.g., to their ability to infect nondividing cells. See, e.g., Mautino and Morgan, AIDS Patient Care STDS 2002 January; 16(1):11-26. See also Lois, C., et al., Science, 295: 868-872, Feb. 1, 2002, describing the FUGW lentiviral vector; Somia, N., et al. J. Virol. 74(9): 4420-4424, 2000; Miyoshi, H., et al., Science 283: 682-686, 1999; and U.S. Pat. No. 6,013,516.

A number of nonviral vectors and gene delivery systems exist, any of which may be used in the practice of the invention. For example, extrachromosomal DNA (e.g., plasmids) may be used as a gene therapy vector. See, e.g., Stoll, S, and Calor, M, "Extrachromosomal plasmid vectors for gene therapy", Curr Opin Mol Ther, 4(4):299-305, 2002. According to one approach, the inclusion of appropriate genetic elements from various papovaviruses allows plasmids to be maintained as episomes within mammalian cells. Such plasmids are faithfully distributed to daughter cells. In particular, viral elements of various polyomaviruses and papillomaviruses such as BK virus (BKV), bovine papilloma virus 1 (BPV-1) and Epstein-Barr virus (EBV), among others, are useful in this regard. The invention therefore provides plasmids that direct expression of a polypeptide, variant, fragment, etc. to mammalian cells, preferably domesticated mammal cells, and most preferably human cells. According to certain embodiments of the invention the plasmids comprise a viral element sufficient for stable maintenance of the transfer plasmid as an episome within mammalian cells. Appropriate genetic elements and their use are described, for example, in Van Craenenbroeck, et al., Eur. J Biochem. 267, 5665-5678 (2000) and references therein, all of which are incorporated herein by reference. Plasmids can be delivered as "naked DNA" or in conjunction with a variety of delivery vehicles.

Protein/DNA polyplexes represent an approach useful for delivery of nucleic acids to cells and subjects. These vectors may be used to deliver constructs directing transcription of the inventive nucleic acids (constructs that direct transcription of polypeptides, fragments, or variants) or may be used to deliver the nucleic acids themselves. Thus their use is not limited to gene therapy. See, e.g., Cristiano, R., Surg. Oncol. Clin. N. Am., 11(3), 697-715, 2002. Cationic polymers and liposomes may also be used for these purposes. See, e.g., Merdan, T., et al., "Prospects for cationic polymers in gene and oligonucleotide therapy against cancer", Adv Drug Deliv Res, 54(5), 715-58, 2002; Liu, F. and Huang, L., "Development of non-viral vectors for systemic gene delivery", J. Control. Release, 78(1-3):259-66, 2002; Maurer, N., et al., "Developments in liposomal drug delivery systems", Expert Opin Biol Ther, 1(2), 201-26, 2001; and Li, S, and Ma, Z., "Nonviral gene therapy", Curr Gene Ther, 1(2), 201-26, 2001. See Rasmussen, H., Curr Opin Mol. Ther, 4(5), 476-81, 2002 for a review of angiogenic gene therapy strategies for the treatment of cardiovascular disease. Numerous reagents and methods for gene therapy are described in Philips, I., (ed.), Methods in Enzymology, Vol. 346: Gene Therapy Methods, Academic Press, 2002.

Any of the nucleic acid delivery vehicles (or nucleic acids themselves) can be targeted for delivery to specific cells, tissues, etc. In particular, they can be targeted to cardiac cells using antibodies or ligands that specifically bind to an apelin polypeptide as discussed further below. Nucleic acids can be directly conjugated to such antibodies or ligands, which then deliver the nucleic acids to cardiac cells.

Gene therapy protocols may involve administering an effective amount of a gene therapy vector comprising a nucleic acid capable of directing expression of an apelin or APJ receptor polynucleotide, variant, or fragment to a subject. Another approach that may be used alternatively or in combination with the foregoing is to isolate a population of cells, e.g., stem cells or immune system cells from a subject, optionally expand the cells in tissue culture, and administer a gene therapy vector to the cells in vitro. The cells may then be returned to the subject. Optionally, cells expressing the desired polynucleotide, siRNA, etc., can be selected in vitro prior to introducing them into the subject. In some embodiments of the invention a population of cells, which may be cells from a cell line or from an individual who is not the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

In yet another approach, oral gene therapy may be used. For example, U.S. Pat. No. 6,248,720 describes methods and compositions whereby genes under the control of promoters are protectively contained in microparticles and delivered to cells in operative form, thereby achieving noninvasive gene delivery. Following oral administration of the microparticles, the genes are taken up into the epithelial cells, including absorptive intestinal epithelial cells, taken up into gut associated lymphoid tissue, and even transported to cells remote from the mucosal epithelium. As described therein, the microparticles can deliver the genes to sites remote from the mucosal epithelium, i.e. can cross the epithelial barrier and enter into general circulation, thereby transfecting cells at other locations.

Methods for identifying compounds capable of modulating gene expression are described, for example, in U.S. Pat. No. 5,976,793. These methods may be either to identify compounds that increase gene expression or to identify compounds that decrease gene expression. The screening methods described therein are particularly appropriate for identifying compounds that do not naturally occur within cells and that modulate the expression of genes of interest whose expression is associated with a defined physiological or pathological effect within a multicellular organism. Additional methods for identifying agents that increase expression of genes are found in Ho, S., et al., Nature, 382, pp. 822-826, 1996, which describes homodimeric and heterodimeric synthetic ligands that allow ligand-dependent association and disassociation of a transcriptional activation domain with a target promoter to increase expression of an operatively linked gene.

Expression can also be increased by introducing additional copies of a coding sequence into a cell of interest, i.e., by introducing a nucleic acid comprising the coding sequence into the cell. Preferably the coding sequence is operably linked to regulatory signals such as promoters, enhancers, etc., that direct expression of the coding sequence in the cell. The nucleic acid may comprise a complete gene, or a portion thereof, preferably containing the coding region of the gene. The nucleic acid may be introduced into cells grown in culture or cells in a subject using any suitable method, e.g., any of those described above.

Agents can be tested to determine whether they modulate the expression of a gene. The invention provides a method for identifying an agent that modulates expression of a polynucleotide or polypeptide comprising steps of: (i) providing a sample comprising cells that express apelin or an APJ receptor polynucleotide or polypeptide; (ii) contacting the cells with a candidate agent; (iii) determining whether the level of expression of the polynucleotide or polypeptide in the presence of the compound is increased or decreased relative to the level of expression or activity of the polynucleotide or polypeptide in the absence of the compound; and (iv) identifying the compound as a modulator of the apelin or APJ receptor polynucleotide or polypeptide if the level of expression or activity of the apelin or APJ receptor polynucleotide or polypeptide is higher or lower in the presence of the compound relative to its level of expression or activity in the absence of the compound.

Expression of an apelin or APJ receptor polynucleotide or polypeptide can be measured using a variety of methods well known in the art in order to determine whether any candidate agent increases or decreases expression (or for other purposes). In general, any measurement technique capable of determining RNA or protein presence or abundance may be used for these purposes. For RNA such techniques include, but are not limited to, microarray analysis (For information relating to microarrays and also RNA amplification and labeling techniques, which may also be used in conjunction with other methods for RNA detection, see, e.g., Lipshutz, R., et al., Nat Genet., 21(1 Suppl):20-4, 1999; Kricka L., Ann. Clin. Biochem., 39(2), pp. 114-129; Schweitzer, B. and Kingsmore, S., Curr Opin Biotechnol 2001 February; 12(1): 21-7; Vineet, G., et al., Nucleic Acids Research, 2003, Vol. 31, No. 4; Cheung, V., et al., Nature Genetics Supplement; 21:15-19, 1999; Methods Enzymol, 303:179-205, 1999; Methods Enzymol, 306: 3-18, 1999; M. Schena (ed.), DNA Microarrays: A Practical Approach, Oxford University Press, Oxford, UK, 1999. See also U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; 6,235,483; WO 93/17126; WO 95/11995; WO 95/35505; EP 742 287; EP 799 897; U.S. Pat. Nos. 5,514,545; 5,545,522; 5,716,785; 5,932,451; 6,132,997; 6,235,483; US Patent Application Publication 20020110827).

Other methods for detecting expression include Northern blots, RNAse protection assays, reverse transcription (RT)-PCR assays, real time RT-PCR (e.g., Taqman™ assay, Applied Biosystems), SAGE (Velculescu et al. Science, vol: 270, pp. 484-487, October 1995), Invader® technology (Third Wave Technologies), etc. See, e.g., E is, P. S. et al., Nat. Biotechnol. 19:673 (2001); Berggren, W. T. et al., Anal. Chem. 74:1745 (2002), etc. Methods for detecting UIR or DIR polypeptides include, but are not limited to, immunoblots (Western blots), immunofluorescence, flow cytometry (e.g., using appropriate antibodies), mass spectrometry, and protein microarrays (Elia, G., Trends Biotechnol, 20(12 Suppl):S19-22, 2002, and reference therein).

As discussed above, the invention provides methods for identifying ligands that modulate (e.g., increase or decrease) activity of an apelin or APJ receptor polypeptide and methods for identifying agents that modulate expression of an apelin or APJ receptor polynucleotide or polypeptide. More generally, the invention also provides a method for identifying an agent that modulates expression or activity of an apelin or APJ receptor polynucleotide or polypeptide comprising steps of: (i) providing a sample comprising apelin or APJ receptor polynucleotide or polypeptide; (ii) contacting the sample with a candidate compound; (iii) determining whether the level of expression or activity of the polynucleotide or polypeptide in the presence of the compound is increased or decreased relative to the level of expression or activity of the polynucleotide or polypeptide in the absence of the compound; and (iv) identifying the compound as a modulator of the expression or activity of the apelin or APJ receptor polynucleotide or polypeptide if the level of expression or activity of the apelin or APJ receptor polynucleotide or polypeptide is higher or lower in the presence of the compound relative to its level of expression or activity in the absence of the compound. In certain embodiments of the method the sample comprises cells that express the apelin or APJ receptor polypeptide. The agents to be screened include any of those discussed above. Agents identified according to the above methods may be further tested in subjects, e.g., humans or other animals. The subject may be normal or may be suffering from or at risk of heart failure of a condition or disease associated with heart failure. The test may involve determining whether administration of the agent reduces or alleviates one or more symptoms or signs of heart failure or improves a prognostic variable such as exercise capacity.

Apelin or APJ receptor also serve as diagnostic targets. The invention therefore provides a method for providing diagnostic or prognostic information related to heart failure or to a disease or condition associated with heart failure comprising steps of: (i) providing a subject in need of diagnostic or prognostic information related to heart failure or to a disease or condition associated with heart failure; and (ii) determining the level of expression or activity of apelin or APJ receptor polynucleotide or polypeptide in the subject or in a biological sample obtained from the subject. The method may further comprise the step of (iii) comparing the determined level of expression or activity with known level(s) determined previously in the subject or in normal subjects or in subjects with heart failure, or in a biological sample obtained from the subject or from normal subjects or from subjects with heart failure. The determined level of expression or activity can be correlated with values that have been associated with particular diagnostic categories (e.g., New York Heart Association classification of heart failure), disease outcomes, likelihood of responding positively to particular treatments, time to progression to a more severe state, etc. The information can be provided to the subject and/or used to guide therapeutic decisions, e.g., the advisability of initiating or terminating various therapies, etc. By "normal subject" is meant a subject not suffering from heart failure or from a disease or clinical condition associated with heart failure as determined using a classification method accepted in the art, e.g., the New York Heart Association classification scheme, which divides subjects into normal or class 1, 2, 3, or 4, with increasing number indicating increasing severity of disease. The classification method may be based on clinical criteria, laboratory criteria, qualitative and/or quantitative tests including imaging tests, etc. For example, ejection fraction can be used to classify subjects, wherein normal is defined as a left ventricular ejection fraction greater than 45%, mild to moderate is 25% to 45%, and severe is less than 25%.

According to certain embodiments of the invention, a level of expression or activity of an apelin or APJ receptor polynucleotide or polypeptide that is higher than would be expected in a normal subject or in a biological sample obtained from a normal subject, indicates an increased likelihood that the subject is at risk of or suffering from heart failure or a disease or condition associated with heart failure. A level of expression or activity of an apelin or APJ receptor polynucleotide or polypeptide that is higher in the subject or in a biological sample obtained from the subject than the level determined previously for that subject indicates that the subject's disease has become more severe and/or that the subject has not responded to therapy. According to certain embodiments of the invention the level of expression of an apelin or APJ receptor polynucleotide or polypeptide is an indicator of the severity of heart failure or of a disease or condition associated with heart failure, with a higher level, e.g., relative to normal being indicative of greater severity.

In any of the foregoing methods the level of expression of an expression product (e.g., an RNA transcribed from a gene or a polypeptide encoded by such an RNA) can be determined according to standard methods, some of which are described elsewhere herein. For example, a sample of cardiac tissue (cardiac biopsy) can be obtained. Such biopsies are routinely performed, e.g., to assess rejection following cardiac transplant. Endocardial or myocardial biopsies can be done using a catheter inserted into the heart via the jugular vein. RNA can be detected using in situ hybridization or extracted and measured, optionally being amplified prior to measurement. RT-PCR can be used. Protein expression can be measured using various immunological techniques including immunohistochemistry, immunoblot, immunoassays such as ELISA assays, etc.

Rather than determining the level of expression of a polynucleotide or polypeptide, in certain embodiments of the invention the functional activity of the polypeptide is measured. For example, in the case of a kinase such as MAPK4 or TEC, kinase activity can be measured. Methods for doing so are well known in the art and can utilize either endogenous substrates or synthetic substrates, e.g., substrates containing consensus sequences for phosphorylation for either serine/threonine or tyrosine kinases. Activity of other polypeptides having known biological and/or enzymatic activities can be measured using any of a variety of methods known in the art, as appropriate for the particular activity.

Instead of determining the expression level or activity of a polynucleotide or polypeptide in a sample obtained from a subject, the expression level can be measured using imaging as described above. Activity can also be measured using imaging techniques, e.g., by targeting a substrate for an enzymatic reaction catalyzed by the polypeptide to cardiac cells and monitoring conversion of the substrate into product by performing sequential imaging. Labeled substrates can be used to facilitate such monitoring. Methods for performing functional imaging, either invasively or noninvasively, are known in the art.

In the case of apelin, the polypeptide encoded by the gene is secreted from cells and circulates in the bloodstream. In such cases the level of expression or activity of the gene product can be measured in a blood or serum sample obtained from the subject. Polypeptides that are secreted by cells typically include a signal sequence that directs their secretion. In addition, certain of the gene products encode receptors. The invention also provides diagnostic methods based on the measurement of levels of endogenous ligands for these receptors. According to certain embodiments of the invention the level of an endogenous ligand for an APJ receptor polypeptide is measured instead of or in addition to the level of expression or activity of the corresponding apelin polypeptide. For example, as further described below, measurement of circulating apelin levels correlates with disease severity in heart failure. The level of the ligand can be measured using any suitable method, e.g., radioimmunoassay, ELISA, functional assays, etc.

As a particular example, the invention provides a method of providing diagnostic or prognostic information related to heart failure or to a disease or condition associated with heart failure comprising steps of: (i) providing a subject in need of diagnostic or prognostic information related to heart failure or to a disease or condition associated with heart failure; and (ii) determining the level of apelin in the subject or in a biological sample obtained from the subject. The method may further comprise the step of (iii) comparing the determined apelin level with known level(s) determined previously in the subject or in normal subjects or in subjects with heart failure, or in a biological sample obtained from the subject or from normal subjects or from subjects with heart failure. The sample, can be, e.g., a blood, plasma, or serum sample. Any apelin peptide can be measured, e.g., apelin-12, apelin-13, or PYR-apelin-13. The measurement can be performed, using for example, a radioimmunoassay or ELISA, etc.

The plasma level of apelin is correlated with particular diagnostic categories for heart failure. In particular, there are significant increases in the plasma level of apelin in early heart failure through NYHA class 2, while in later stages (class 3-4), the mean level is lower. Thus apelin levels rise in mild to moderate disease but fall in severe disease. The level of apelin may thus be used to distinguish patients suffering from mild to moderate disease with normal subjects and those suffering from severe disease. It may be particularly useful to monitor apelin levels over time. For example, if the apelin level in a subject initially classified as normal begins to rise, this may be indicative of progression to mild or moderate heart failure. If the apelin level in a subject initially classified as having severe heart failure begins to rise, this may be indicative that the subject's condition is improving to a mild or moderate disease severity. In general, it may be desirable to consider apelin level together with other indicators of disease severity. For example, if an initial measurement of apelin level indicates that the individual has an apelin level that is consistent with either normal or severe disease, clinical and/or other criteria will generally allow the subject to be unambiguously assigned to either the normal or severe category. The apelin level may be used thereafter to more accurately quantify the subject's disease state and/or monitor the response to treatment. The apelin level can be provided to the subject and/or used to guide therapeutic decisions, e.g., the advisability of initiating or terminating various therapies, etc. It is noted that plasma levels of another endogeonous peptide, brain natriuretic peptide (BNP) are used clinically as a diagnostic tool in human heart failure (Hobbs, R. E., "Using BNP to diagnose, manage, and treat heart failure", Cleveland Clinic Journal of Medicine, 70(4): 333-336 (2003); Bhatia, V., Nayyar, P., and Dhinda, S., "Brain natriuretic peptide in diagnosis and treatment of heart failure", J. Postgrad Med, 49(2): 182-5 (2003)).

EXEMPLIFICATION

Example 1

Measurement of Apelin Levels in Cardiac Tissue

Materials and Methods

Apelin assay. Eight mg of tissue was boiled in 0.1 M acetic acid for 10 minutes, homogenized, then centrifuged at 12,000 rpm for 10 minutes and the supernatant used to quantify total protein concentration via the Bradford Assay (Biorad, Hercules, Calif.). Equal amounts of total protein (concentration 300 µg/ml) were used in the Apelin-12 EIA assay kit (Phoenix Pharmaceuticals, Belmont, Calif.) following manufacturer's instructions. 50 µl of plasma was used directly for the assay. Comparisons were made using Student's paired t-test and one way analysis of variance with post hoc tests according to Fisher (SPSS software version 11.0).

Results

Apelin is increased in cardiac tissue following LVAD implantation. Competitive enzyme immunoassay was used to detect levels of apelin in the samples of left ventricle that were used for hybridization. Tissue apelin levels were significantly higher post LVAD (FIG. 1A; pre 0.967±0.26; post 2.246±0.41 in ng/ml; P<0.001; units are concentration of apelin in ng/ml within a normalized total protein concentration of 300 µg/ml). This reflects a change in the upward direction in all but two patients. Since the expression of the receptor and its ligand were moving in concert, we examined the relationship between the two per individual. A weak but significant positive correlation was found (y=−0.42+1.15x; $R2=0.3$; P=0.019; data not shown).

Example 2

Localization of Apelin in Human Cardiac Tissue

Materials and Methods

Immunohistochemistry. Tissue was frozen in OCT (Tissue-Tek, Torrance, Calif.). Four micron thick sections were cut and stored at minus 80° C. Slides were fixed in minus 20° C. acetone, and air dried. Blocking was achieved using 10% goat serum (Zymed, S. San Francisco, Calif.). Sections were stained with apelin polyclonal antibody (Phoenix Pharmaceuticals, Belmont, Calif.) and with CD31 (Cymbus Biotechnology Ltd, England) Secondary incubation used anti-rabbit envision+(Dako, Carpenteria, Calif.) for apelin and anti-mouse envision+(Dako, Carpenteria, Calif.) for CD31. The chromagen substrate 3-amino-9-ethylcarbazole was used. Sections were counterstained using hematoxylin.

Results

Figure 1B:
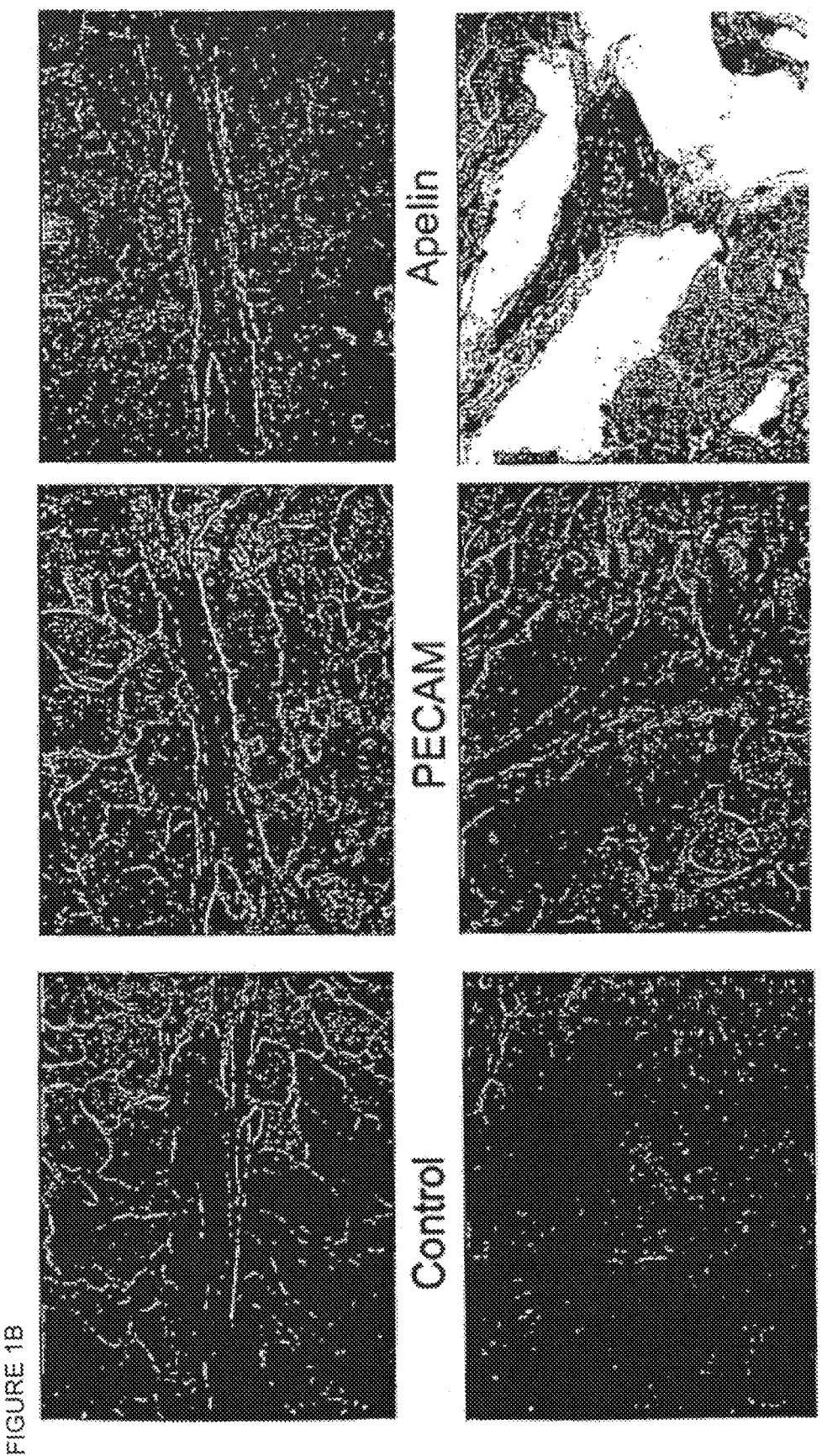

Apelin is highly specifically localized to the vasculature in cardiac tissue. Immunohistochemistry was carried out with the same antibody used for detecting apelin tissue levels by enzyme immunoassay. The localization of apelin in normal human cardiac left ventricle was compared with that from end stage, failing left ventricle. In both tissues, the distribution of staining was similar. We found that cardiac vessels stain densely for apelin with negligible staining in myocardial cells (FIG. 1B). Staining of consecutive sections for PECAM (CD31) confirmed the endothelial localization, although high powered views suggested apelin staining extended to smooth muscle cells also. Despite little staining overall of the myocardium, in the failing heart, apelin was detectable at low levels in the myocardial cells also suggesting extension of the signaling system in late stage disease.

Example 3

Measurement of Plasma Apelin Levels in Humans with Heart Failure

Materials and Methods

Apelin assay. This was performed as described in Example 1, but rather than tissue, 50 µl of plasma was used.

Results

Figure 2:
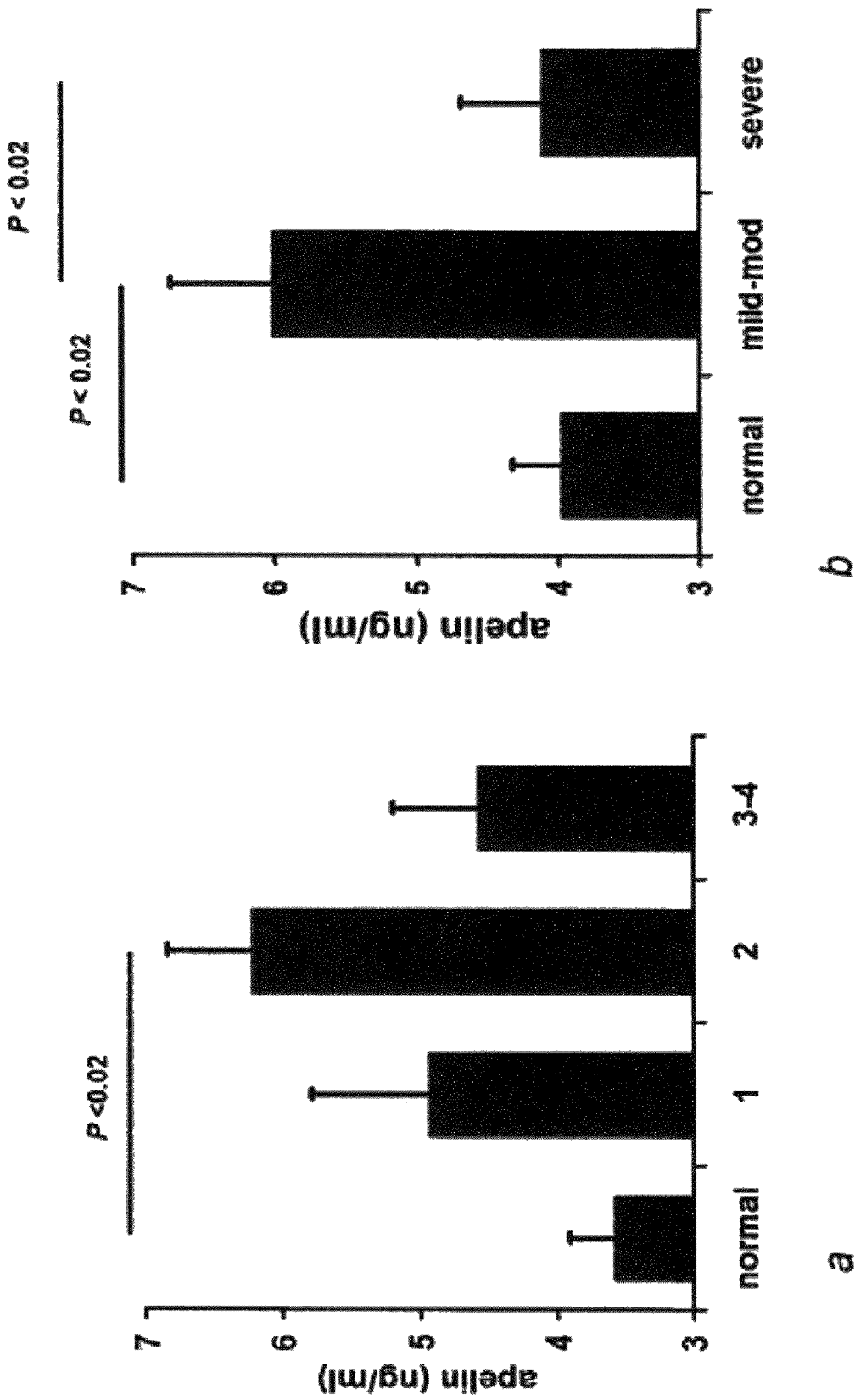
FIGS. 2A and 2B show plasma apelin levels in heart failure.

To determine the role of apelin in earlier stages of heart failure, plasma levels of apelin were measured in blood from 80 heart failure patients with a broad spectrum of disease severity (male n=63, female n=17, mean age 63 years, standard deviation 10 years). Since plasma apelin levels had not previously been reported in humans, 32 normal subjects were also studied to determine the range of normal. Plasma apelin was detectable in plasma from healthy human subjects (3.58±0.33 ng/ml), rose in the early stages of heart failure (New York Heart Association class 1:4.94±0.85 ng/ml) and was maximum in those classified as NYHA Class 2 (6.22±0.63, P<0.02). In those with severe disease, plasma apelin was lower (NYHA Class 3-4: 4.58±0.62 ng/ml) but this change was not significant (FIG. 2A). Mirroring the changes in functional class, dividing the patients by ejection fraction also revealed a rise in apelin from normal to mild-to-moderate LV dysfunction (3.98±0.34 vs 6.02±0.72 ng/ml, P<0.02). Similarly, in later stage disease, apelin level declined (severe LV dysfunction 4.11±0.58 ng/ml, P<0.02, FIG. 2B).

Example 4

Localization of Apelin and APJ in Developing and Adult Mouse Heart

Materials and Methods

Expression of the APJ receptor. Adult mice were perfusion fixed with 4% paraformaldehyde, and adult heart and whole embryos further fixed over night, embedded in paraffin and sectioned. Five micron thick sections were cut and stored at 4° C. Blocking was achieved using 1.5% goat serum (Vector labs, Burlingame, Calif.). Sections were stained with APJ polyclonal antibody (Lifespan Biosciences, Seattle, Wash., LSA64, 1/100 dilution). Secondary antibody was biotinylated anti-rabbit raised in goat (Vector labs, Burlingame, Calif., 1/200 dilution). For embryo sections, the chromagen substrate was BCIP/NBT for alkaline phosphatase (Vector labs, Burlingame, Calif.), and sections were counterstained with nuclear fast red. For the heart sections, the chromagen substrate was vector red for alkaline phosphatase (Vector labs, Burlingame, Calif.), and sections were counterstained with hematoxylin.

Results

Figure 3:
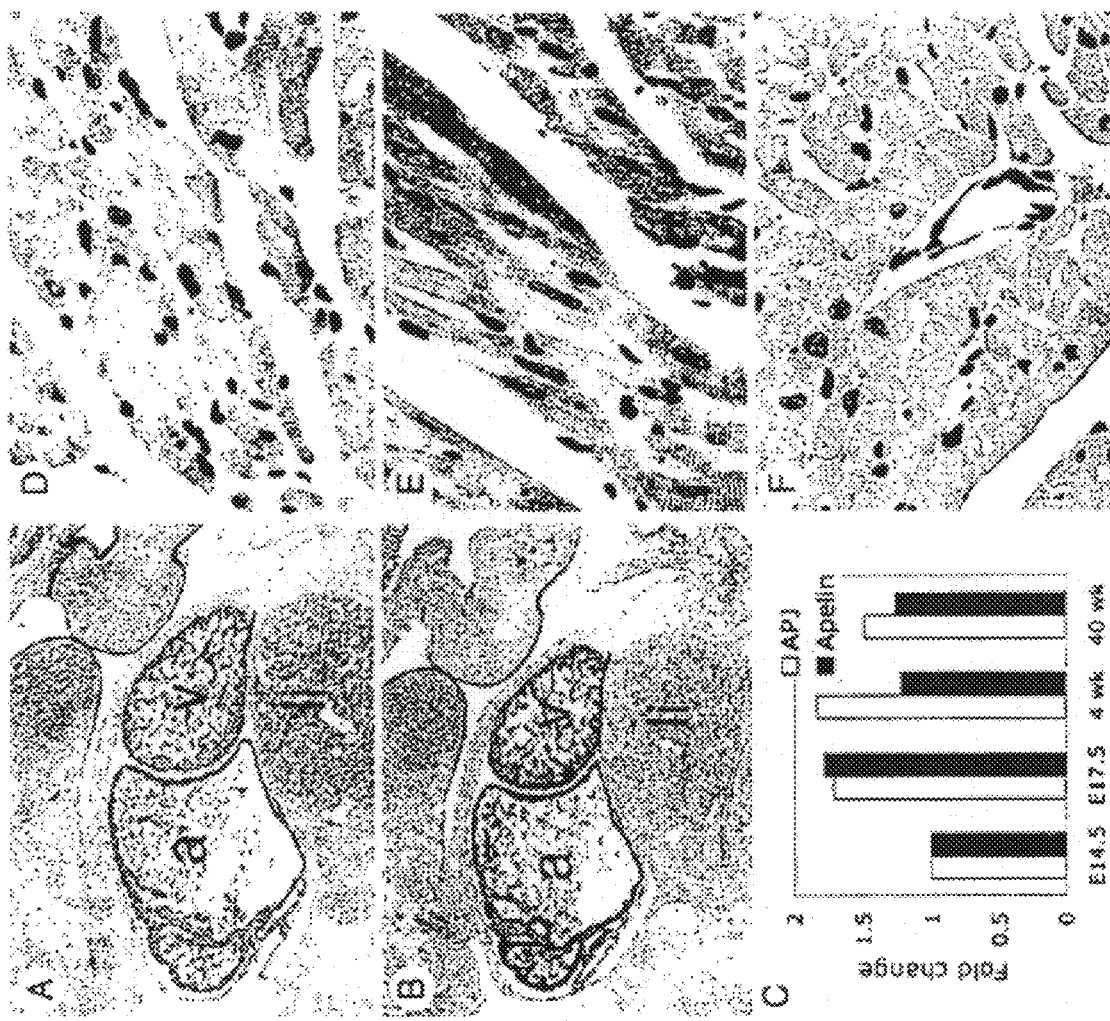
FIGS. 3A-3F shows immunohistochemistry of apelin and APJ in the developing and adult mouse heart. Specific immunolocalization of both proteins in the developing myocardium revealed very similar patterns of expression as early as embryonic day 13.5 (Panels 3A, 3B: A—atrium, V—ventricle, li—liver). Real time quantitative RT-PCR of isolated heart mRNA suggested that the relative contribution to the total myocardial RNA by these transcripts remains relatively constant through late gestation and adulthood (Panel 3C). In the adult mouse heart, immunolocalization of APJ expression was identified in association with both atrial and ventricular myocardial cells (Panels 3D, 3E). A control slide without the addition of the secondary antibody is shown in Panel 3F.

Expression of APJ receptor. Immunohistochemistry with antibodies for apelin and APJ revealed specific immunolocalization of both proteins in the developing myocardium, with very similar patterns of expression as early as embryonic day 13.5 (FIG. 3, Panels A, B). Real time quantitative RT-PCR of isolated heart mRNA validated this finding, and suggested that the relative contribution to the total myocardial RNA by these transcripts remains relatively constant through late gestation and adulthood (FIG. 3, Panel C). In the adult mouse heart, immunolocalization of APJ expression was identified in association with both atrial and ventricular myocardial cells (FIG. 3, Panels D-F).

Example 5

Effects of Acute and Chronic Apelin Administration In Vivo

Materials and Methods

Peptide reagents. Apelin-12 was purchased from Bachem (Bachem Bioscience, King of Prussia, Pa.). Pyroglutamylated apelin-13 (PYR-apelin-13) was purchased from American Peptide Company (Sunnyvale, Calif.). Apelin-12 circulates as pyroglutamylated apelin 13 and the latter is felt to be more stable. Apelin was dissolved in distilled, autoclaved, degassed water, frozen at −20 degrees C. at high concentration, and aliquoted on the morning of use.

Magnetic resonance imaging. Male C57B/l6 mice aged 16 weeks (n=9) were scanned twice on subsequent days. The animals underwent general anesthesia while breathing spontaneously via a nose cone fitted carefully to minimize escape of anesthetic into the environment. 2% isoflurane was administered with an oxygen flow rate of 1-2 l/min. Platinum needle ECG leads were inserted subcutaneously. Respiration was monitored by means of a pneumatic pillow sensor positioned against the abdomen. Mouse body temperature was maintained during scanning at 37° C. by a flow of heated air thermostatically controlled by a rectal temperature probe. Magnetic resonance images were acquired on a 4.7T Oxford magnet controlled by a Varian Inova console (Varian, Palo Alto, Calif.) using a transmit-receive, quadrature, volume coil with an inner diameter of 3.5 cm. Image acquisition was gated to respiration and to the ECG R wave (SA Instruments, Stony Brook, N.Y.). Coronal and sagittal scout images led to the acquisition of multiple contiguous 1 mm thick, short axis slices orthogonal to the interventricular septum. Nine cine frames were taken at each slice level with the following sequence parameters: TE=2.8 ms, NEX=12, FOV=3×3 cm, matrix=128×128, flip angle=60°. Cine frames were spaced 16 ms apart and acquired through slightly more than one cardiac cycle guaranteeing acquisition of systole and diastole. On the second day of scanning, mice received 300 µg/kg body weight of apelin-12 as an intraperitoneal injection one hour prior to scanning. A pilot study had previously identified one hour as an appropriate time within which to identify apelin effects resulting from peritoneal absorption. Planimetry measurements of end diastolic and end systolic dimension were derived offline from short axis views of the left ventricle at the level of the papillary muscles using ImageJ software (National Institutes of Health, Bethesda, Md.). Ejection fraction was calculated as [LVEDA-LVESA]/LVEDA.

Pressure-volume hemodynamics. Pressure-volume hemodynamics were assessed using the Aria System (Millar Instruments, Houston, Tex.). Male C57B1/6 mice aged 8-12 weeks (n=10) were anesthetized with 1-2% isoflurane in oxygen. The internal jugular vein was cannulated with PE tubing and a 10% albumin solution infused at 5 µl/min following a bolus of 150 µl over 5 minutes. After tracheotomy, a 19G cannula was inserted into the trachea and the animal was ventilated at a tidal volume of 200 µl at 100 breaths per minute (Harvard Apparatus, Holliston, Mass.). Mice were warmed throughout the procedure and constantly monitored for depth of anesthesia. Following an incision just dorsal to the xyphoid cartilage, the diaphragm was visualized from below, and after diaphragmatic incision, the left ventricular apex was visualized. The pressure-volume catheter was then inserted along the long axis of the left ventricle, from where it was adjusted to obtain rectangular shaped pressure-volume loops. Appropriate position was verified post mortem (FIG. 1, Panel D). Baseline loops were recorded following volume replacement, at which point, the inferior vena cava was visualized within the chest and occlusion parameters were recorded during and after a 5 second manual occlusion of this vessel. Next, the albumin solution was replaced by one containing 100 nM Apelin-12 which was infused at 5 µl/min for 20 minutes, following which, baseline and occlusion loops were recorded once again. Signals from the catheter were digitized using the Powerlab system (ADInstruments, Colorado Springs, Colo.) and stored for offline analysis using the PVAN software (Pressure-volume ANalysis, Millar Instruments, Houston, Tex.).

Chronic apelin infusion. To test longer term effects of apelin, we infused 2 mg/kg/day PYR-apelin-13 into 8-12 week male C57/B1/6 mice. A short anesthetic (isoflurane 1% in oxygen 1l/min) facilitated implantation of a 2 ml osmotic minipump under the scruff with staple closure (Alzet Osmotic pumps, Cupertino, Calif., model 1002). Minipumps contained either PYR-apelin-13 (n=10) or sterile normal saline (n=5). Cardiovascular parameters were recorded at 7 days and 14 days by tail cuff sphygmomanomtery (Visitech Systems, Apex, N.C.) and echocardiography (probe frequency 15 MHz, Acuson Sequoia, Siemens, Malvern, Pa.). For echocardiography, mice were anesthetized using isoflurane (0.75-1.25% in oxygen 1l/min) then placed supine and warmed using a heat lamp. Using a gel buffer, parastemal long and short axis views were recorded in each animal to allow estimation of indices of contractility such as fractional shortening (LVEDD-LVESD/LVEDD), cardiac output ([Pi*(Aod){circumflex over ( )}2*VTI*HR]/4), velocity of circumferential shortening ([LVEDD−LVESD]/[ET×LVEDD]), and LV mass (1.05*[(IVSD+LVEDD+PWTD).su-p.3-LVEDD.sup.3) where LVEDD is left ventricular end diastolic diameter, LVESD is left ventricular end systolic diameter, IVSD is inter ventricular septum in diastole, PWTD is posterior wall thickness in diastole, Aod is aortic diameter, VTI is the velocity time integral, ET is ejection time. The last two parameters are derived from Doppler sampling of the outflow tract. All measurements were made by one operator blinded to group. At 7 and 14 days of infusion, these measurements were repeated. Mice were then sacrificed and organs removed for measurement of wet weight.

Data Analysis. Data were analyzed using Student's t statistic (paired) or the repeated measures analysis of variance using the post hoc comparison of Fisher (NCSS 2002). Exact p values are reported for all comparisons.

Results

Figure 4:
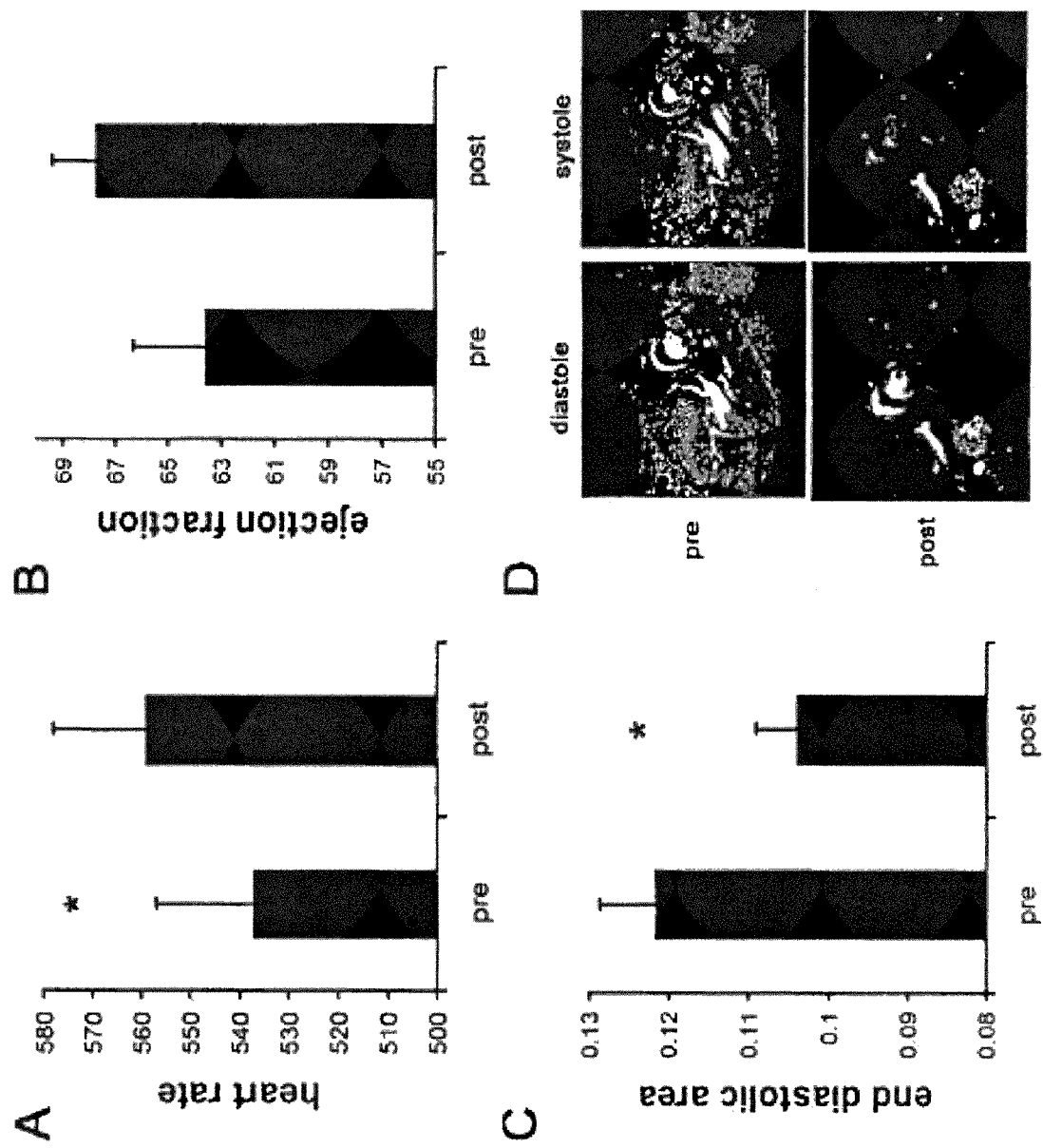
FIGS. 4A-4D shows changes in cardiovascular function following intraperitoneal injection of apelin-12 in C57B16 mice. Mice (n=9) were anesthetized with isofluorance and warmed to 36-37 degrees before magnetic resonance imaging. Electrocardiography revealed a significant increase in HR following apelin injection (Panel 4A). ECG and respiration gated cine magnetic resonance images of the left ventricle taken in short axis reveal a significant reduction in left ventricular end diastolic area (Panel 4C) with an upward trend in ejection fraction (Panel 4B). Panel 4D shows example images of end diastole (left) and end systole (right) from pre (above) and post (below) apelin injection.

Magnetic resonance imaging. Contractility in C57B1/6 mice was first assessed at baseline. Short axis views of the left ventricle at the level of the papillary muscles allowed estimation of end systolic and end diastolic areas by planimetry (FIG. 4, Panel D). Apelin had no effect on the spontaneous rate of respiration (pre:±68±11; post: 66±7 breaths per minute, p=0.7) while heart rate calculated as the inverse of the R-R interval of the electrocardiogram was significantly greater (pre: 537±20; post 559±19 beats per minute, p=0.03, FIG. 4, Panel A). Ejection fraction tended to increase following apelin injection but this did not reach significance (pre: 63.6±2.7; post 67.7±1.6%, p=0.16, FIG. 4, Panel B). However, the end diastolic area was very significantly reduced following apelin injection (pre: 0.122±0.007; post: 0.104±0.005 cm2, p=0.006, FIG. 4, Panel C).

Figure 5:
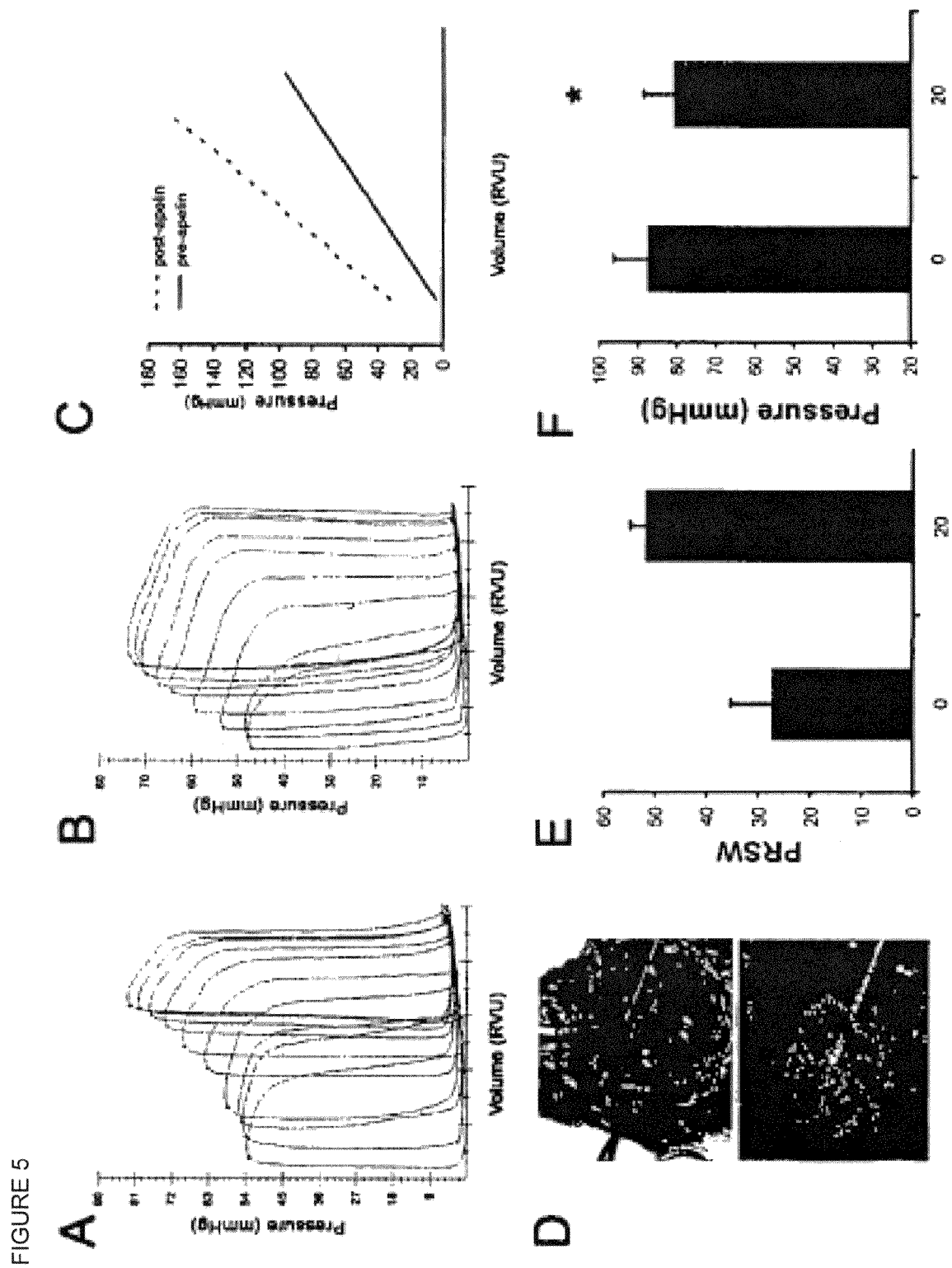
FIGS. 5A-5F shows pressure-volume hemodynamics in response to acute apelin infusion. Ventilated C57B16 mice underwent placement of a catheter along the long axis of the left ventricle (Panel 5D). Pressure-volume loops including preload reduction facilitated by a 5 second manual occlusion of the inferior vena cava were recorded at baseline (Panel 5A) and following 20 minutes of apelin infusion (Panel 5B). Volume is expressed as relative volume units. After apelin infusion, ventricular elastance was increased (Panel 5C, slope of the end systolic pressure-volume relationship, p=0.018) along with preload recruitable stroke work (Panel 5E, p=0.056). Maximum pressure was lower indicating a reduction in afterload (Panel 5F, p=0.02).

Pressure-volume hemodynamics. Separating effects of load and function is not possible with non-invasive imaging and since apelin has effects on both vascular reactivity and intrinsic contractility, we elected to assess ventriculo-vascular coupling via pressure-volume hemodynamics (FIG. 5). Here, intraventricular pressure is measured directly while intraventricular volume is estimated by conductance. Thus, effects of load and intrinsic contractility can be simultaneously and independently assessed through the construction of pressure-volume loops, both at baseline and during preload reduction, achieved by manual compression of the inferior vena cava. Baseline measurements were consistent with those previously reported in the literature for the C57B1/6 mouse. Thoracotomy requires greater depth of anesthesia than non-invasive imaging and this contributes to a lower heart rate in invasive studies. This mild but obligatory cardiovascular depression may also explain the lack of increase in heart rate (pre: 376±21; post: 353±33 bpm, p=0.3) which was seen in the MRI studies.

Systolic function. Consistent with the MR data, LV end diastolic volume was lower, but this difference was not significant (pre: 29.3±6.1; post: 26.2±5.9 RVU, p=0.4). Similarly, load dependent measures of contractility such as ejection fraction and dP/dtmax did not change following apelin infusion. However, inspection of occlusion parameters revealed significant changes in load independent measures of contractility. Both the slope and intercept of the end systolic pressure-volume relationship were increased following apelin infusion (FIG. 5, Panels A-C). Corresponding to this finding, the time varying elastance (the maximum slope of a series of lines drawn through each point in the cardiac cycle) was significantly greater (pre: 6.0±1.5; post: 12.7±3.1, p=0.017). There were also increases in pre-load recruitable stroke work (a regression line fitted to the relationship between end diastolic volume and stroke work; stroke work representing the area of the pressure-volume loop, FIG. 5, Panel E). Although, $dP/dt_{max}$ itself was not different following apelin infusion, the relationship between $dP/dt_{max}$ and end diastolic volume was steeper and its intercept greater (Table 4). Arterial elastance, a steady-state parameter that incorporates peripheral resistance, impedance, compliance and systolic/diastolic time intervals (approximated by the steady state LV end systolic pressure to stroke volume ratio) did not change significantly, however the maximum developed pressure (FIG. 5, Panel F) and end systolic pressure were reduced, most likely reflecting a lower arterial pressure and earlier opening of the aortic valve (confirmed by a lower pressure at $dP/dt_{max}$).

Diastolic function. Time constants of relaxation were not different after apelin infusion. In addition, the slope and intercept derived from a linear model fit of the end diastolic pressure-volume relationship were not different. However, pressure decay is known to be load dependent and model dependency of diastolic parameters is well recognized (Kass D A. Assessment of diastolic dysfunction. Invasive modalities. Cardiol Clin., 18:571-86, 2000). When the end diastolic pressure-volume relationship was fit by a monoexponential of the form [LVEDP=k1*exp(k2*LVEDV)], the constant k1 was greater (pre: 0.064±0.008; post: 0.111±0.002, p=0.09) while the exponential k2 was unchanged (pre: 0.83±0.22; post: 0.69±0.41, p=0.66).

Chronic apelin infusion. We infused PYR-apelin-13 over the course of two weeks at a level previously shown to exert acute hemodynamic effects. No significant changes were seen in saline infused controls from baseline to 14 days. Significant changes in heart rate and blood pressure, known to occur acutely, were not detected over the period of the chronic apelin infusion: neither conscious heart rates (tail cuff method) nor isoflurane heart rates (echo Doppler) were different at any time point and while systolic blood pressure (SBP) trended lower during apelin infusion this change was not significant (Figure, Panel 6B). Left ventricular contractility measurements derived from Doppler ultrasound of the left ventricular aortic outflow tract were significantly increased during apelin infusion. The velocity of circumferential shortening was increased at 14 days (p=0.049, Panel 6C). Similarly, cardiac output was increased at 7 days and this increase was maintained at 14 days (p=0.001, Panel 6D). Despite these increases in contractility, post mortem organ weights were not different between the saline and apelin groups.

TABLE 1

Change in invasive hemodynamic indices following acute apelin infusion.

| | HR | | EDV | | Pmax | | EF | | Ees | | intercept | |
|---|---|---|---|---|---|---|---|---|---|---|---|---|
| | mean | sem | mean | sem | mean | sem | mean | sem | mean | sem | mean | sem |
| Pre apelin | 376 | 21 | 29.3 | 6.1 | 87.5 | 8.9 | 61.2 | 6.8 | 3.7 | 0.9 | −14.2 | 5.9 |
| Post apelin | 353 | 33 | 26.2 | 5.9 | 80.7 | 7.9 | 59.1 | 9 | 6.5 | 1.4 | 0.5 | 5.3 |
| p value | 0.3 | | 0.4 | | 0.02 | | 0.8 | | 0.018 | | 0.013 | |

| | PRSW | | intercept | | dPdt-EDV | | intercept | | Emax | |
|---|---|---|---|---|---|---|---|---|---|---|
| | mean | sem | mean | sem | mean | sem | mean | sem | mean | sem |
| Pre apelin | 27.4 | 8.0 | −41.8 | 21.3 | 127.5 | 27.3 | −22.2 | 5.1 | 6 | 1.5 |
| Post apelin | 51.8 | 3.1 | 11.3 | 3.1 | 179.1 | 34.1 | −2.3 | 4.8 | 12.7 | 3.1 |
| p value | 0.059 | | 0.045 | | 0.16 | | 0.04 | | 0.017 | |

Example 6

Apelin Treatment Improves Exercise Capacity in Mice with Heart Failure

Materials and Methods

Left anterior decending artery ligation. Animals were anesthetized with 2-3% inhalational isoflurane and 50 mg/kg sodium pentobarbital intraperitoneally. They were intubated with a 14 gauge angiocath and positive pressure ventilation with an oxygen/isofluorane mixture was achieved with the Harvard Rodent ventilator. The animals were placed in the left lateral decubitus position and a thoracotomy performed at the 4th intercostal space. Peak inspiratory pressures were monitored and maintained between 10-14 cm of water. The lung was retracted and the pericardium incised. The left coronary artery was ligated with a 7-0 prolene suture until blanching of the distal left ventricle was noted. Heart rate and temperature were monitored during the procedure. After ascertaining complete hemostasis, the chest wall was closed in four layers. The animals were weaned from the ventilator and anesthetic and then extubated and monitored in the recovery area.

Osmotic minipump. Animals were allowed to recover over 4 weeks and developed moderate heart failure over this time. At this point, an osmotic minipump containing apelin was inserted as described above.

Treadmill exercise. Treadmill exercise has long been the gold standard for inducing controlled cardiovascular stress in humans and other large mammals. In mice, a commonly used commercially available setup (Columbus Instruments) employs a moving belt encased in a sealed Plexiglas enclosure, allowing for measurement of oxygen consumption and carbon dioxide production. Stimulus devices consist of a metal shock grid. Metabolic measurements are performed using an open circuit volumetric gas analysis system (Oxymax System; Columbus Instruments). The low dead space of this circuit allows quick gas equilibration with a $t_{1/2}$ of 30 s, which is highly suitable for use during graded exercise protocols. The incremental exercise protocol increases in slope every 3 min until exhaustion. Exhaustion was considered to exist if a mouse spent more than a few seconds on the shock device, at which point the experiment was terminated.

Results

Figure 6:
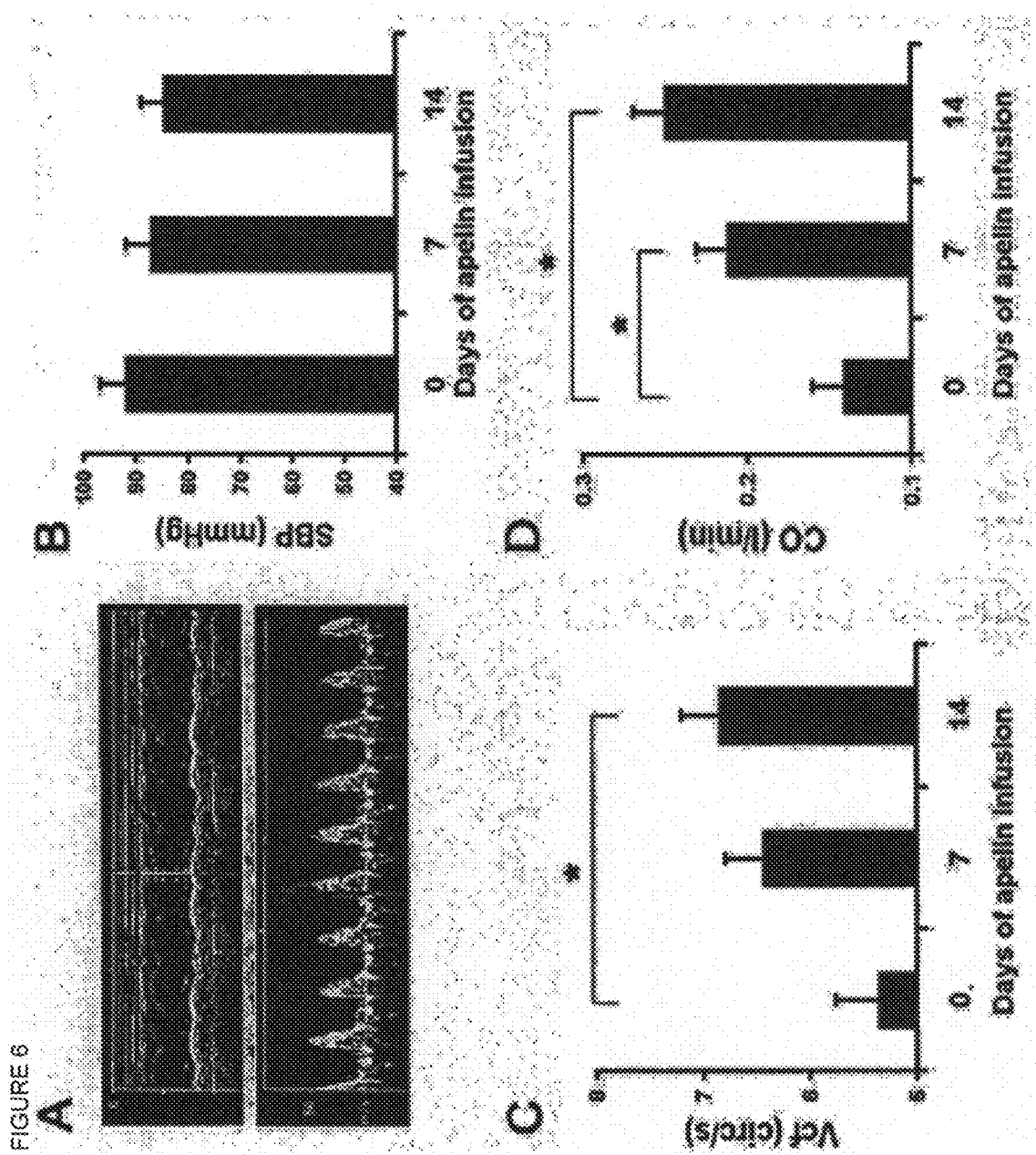
FIGS. 6A-6D shows the effect of chronic apelin infusion in C57B16 mice. Long axis and short axis views of the left ventricle with Doppler sampling of the outflow tract were used to estimate left ventricular contractility in vivo (Panel 6A). The velocity of circumferential shortening (Panel 6C) and cardiac output (Panel 6D) were significantly increased from baseline following two weeks of PY-apelin-13 infusion. Systolic blood pressure as determined by tail cuff was also lower but this did not reach significance (Panel 6B).
Figure 7:
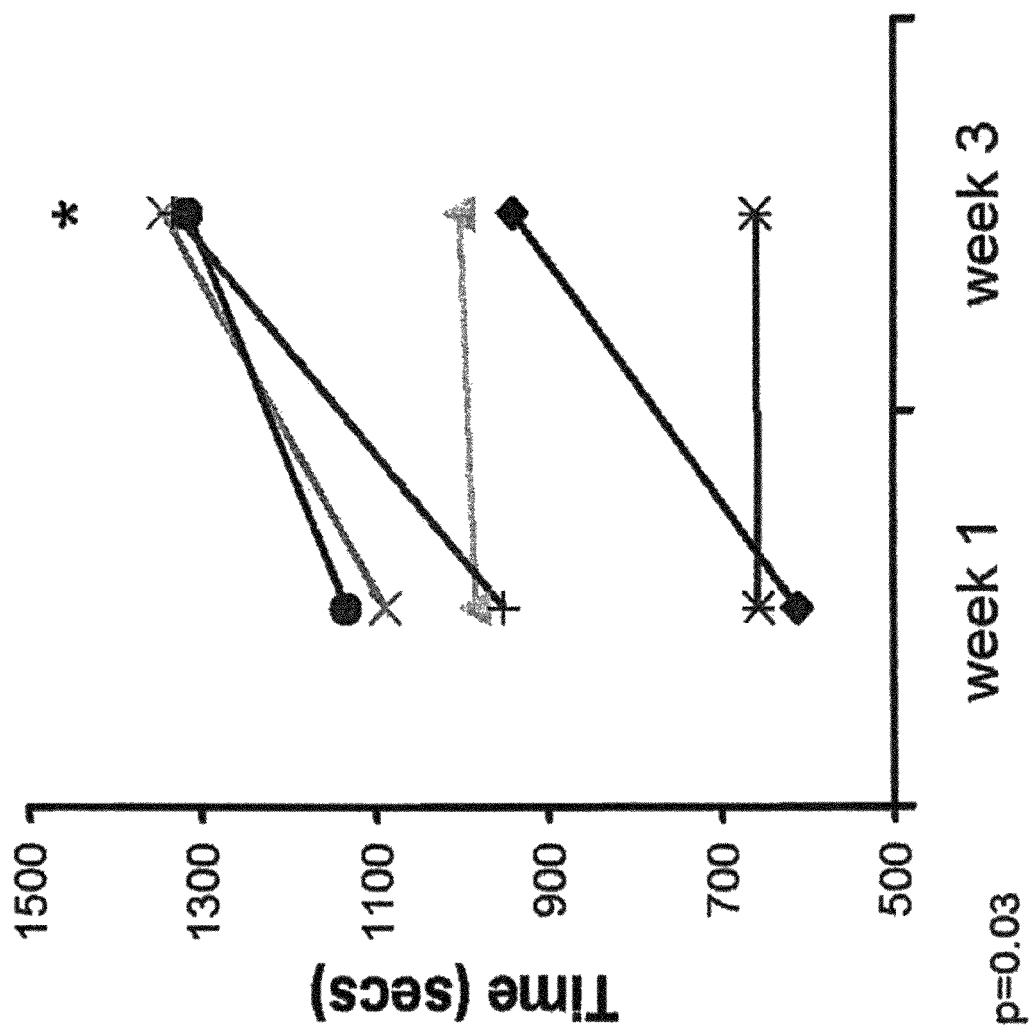
FIG. 7 is a graph showing showing changes in exercise capacity in mice with experimentally induced heart failure from 1-3 weeks during chronic apelin treatment. The graph shows measurements of treadmill time to exhaustion.

Mice (n=6) with experimentally induced heart failure were administered Pyr-apelin-13 (2 mg/kg/day) by means of an implanted osmotic pump. Mice were subjected to treadmill exercise testing at time points during weeks 1 and 3. The time points were 16-17 days apart. The data is presented below and in FIG. 7. $t_1$ represents time to exhaustion at the first time point, and $t_2$ represents time to exhaustion at the second time point. In FIG. 7, the first and second data points for each mouse are indicated using identical symbols. As shown in FIG. 6, the average time to exhaustion increased markedly between weeks 1 and 3. The data was analyzed using a paired t-test. The p-value was <0.05. A control group of mice was administered saline. Average exercise capacity diminished in this group between 1 and 3 weeks.

Additional parameters such as heart rate, blood pressure, cardiac output, plasma apelin levels, etc., can also be assessed.

TABLE 2

Exercise capacity in mice treated with apelin.

| Mouse # | Treatment | $t_1$ | $t_2$ |
|---|---|---|---|
| 1 | Apelin | 612 | 941 |
| 2 | Apelin | 985 | 1003 |
| 3 | Apelin | 1090 | 1345 |
| 4 | Apelin | 656 | 660 |
| 5 | Apelin | 1134 | 1317 |
| 6 | Apelin | 952 | 1332 |

Example 7

Apelin is an Endogenous Regulator of Cardiovascular Function and Rescues Neurohormonal Heart Failure Materials and Methods Generation and genotyping of the apelin null mouse. A mouse apelin cDNA probe (PstI-SacI fragment) was employed for screening a CJ7 cell line (129 SV) CITB Mouse BAC library (Invitrogen) providing three positive clones. Clone 337 K 3 was chosen for the strongest hybridization signal and its exon/intron structure was determined using the Ensembl Genome Browser. The BAC clone was restriction mapped and two homologous regions (9.19-kb HindIII-NaeI 5' fragment and 7.93 kb HpaI/EcoRI 3' fragment) were subcloned into the pBlueScript II KS vector (Stratagene). A 5.7-kb fragment for the 5' arm was further subcloned into the pPD46.21 vector containing a 3.7-kb galactosidase (LacZ) cassette. A 4.7-kb fragment for the 3' arm was subcloned into the pSL1180 vector (Stratagene) to obtain additional restriction sites. The replacement targeting vector was constructed in the pKO Scrambler NTKV-1901 vector (Stratagene) using a PmeI-XhoI fragment for the 5' arm-lacZ (5.7 kb-3.7 kb) and a 4.7-kb EcoRI-EcoRI fragment for the 3' arm with the neomycin phosphotransferase (neo) cassette in between. Also, a cassette for herpes simplex virus-thymidine kinase was provided outside the region of homology to allow negative selection. TL-1 129SVJ embryonic stem cells were used for transfection of the targeting vector. Cell culture, transfection, and positive and negative selection were performed and genomic DNA was isolated from each clone and evaluated by Southern blot with 5' and 3' probes outside the homology domains. Two of the correctly targeted embryonic stem cell clones were injected into C57Bl/6 blastocysts to generate chimeric animals. Two chimeric male mice were obtained and bred to C57Bl/6 females (Jackson Laboratories, Bar Harbor, Me.) to obtain heterozygous pups. Male heterozygous mice were bred to C57Bl/6 females five times before homozygous animals were generated. Thus all experiments were carried out on mixed background C57Bl/6-129SVJ animals and their littermate controls. Genotyping of knockout animals was performed with DNA isolated from tail tissue digested with BglII (5') and HindIII (3') and separated on 0.7% agarose gels. After transfer to nylon membranes, blots were hybridized with radiolabeled probes synthesized utilizing 5' (HindIII-PmeI) or 3' (EcoRI-HindIII) fragments by random priming.

Graded treadmill running. Male mice aged 10-14 weeks (apelin+/+, n=17; apelin−/−, n=12) were placed into an a Simplex II metabolic rodent treadmill (Columbus Instruments, Columbus, Ohio) which allows measurement of oxygen consumption (VO2) and carbon dioxide production (VCO2) using a closed-chamber volumetric method of gas analysis. The respiratory exchange ratio (RER) was calculated as the ratio of VCO2 to VO2. Calibration of the O2 and CO2 gas sensors was performed before each experiment using a standard gas mixture (0.5% CO2—20.5% O2—79% N2) and an offset gas (100% N2). Mice were subjected to a graded exercise protocol. Briefly, mice were placed into the exercise chamber and allowed to equilibrate for 6 minutes. Treadmill activity was initiated at 7.5 m/min at a 4° incline and was increased 2.5 m/min and 2° every 3 minutes until the mice showed signs of exhaustion. This was defined as spending >10 seconds on the shock bar. Mice were then allowed to recover in the chamber for 15 minutes. This exercise protocol was performed only once on each mouse so that conditioning was not a confounder.

Magnetic resonance imaging. Male mice aged 14-18 weeks (apelin+/+, n=8; apelin−/−, n=7) were scanned as previously described. Briefly, the mice were anesthetized with 2% isoflurane with an oxygen flow rate of 1 L/min. ECG leads were inserted subcutaneously and respiration was monitored using a pneumatic pillow placed on the abdomen. The mouse body temperature was monitored by a rectal probe and kept at 37° C. by heated air. Magnetic resonance images were acquired on a 4.7 T Oxford magnet controlled by a Varian Inova console (Varian, Palo Alto, Calif.). Image acquisition was gated to respiration and to the ECG R wave (SA Instruments, Stony Brook, N.Y.). Coronal and sagittal scout images were followed by six contiguous 1-mm-thick, short axis slices orthogonal to the interventricular septum. Nine cine frames were taken at each slice level and were acquired through more than one cardiac cycle guaranteeing acquisition of systole and diastole. Measurements of end systole and end diastole were derived from these short axis views of the left ventricle at the level of the papillary muscles using ImageJ software (National Institutes of Health, Bethesda, Md.). Ejection fraction was calculated as [LVEDA−LVESA]/LVEDA where LVEDA is left ventricular end diastolic area and LVESA is left ventricular end systolic area.

Echocardiography. Two dimensional and M mode echocardiography was carried out using thea GE Vivid ultrasound platform with the small animal probe (13 MHz). Male mice aged 15-16 weeks (apelin+/+, n=10; apelin−/−, n=10) were anesthetized using 1% isoflurane in oxygen (1.5 l/min). After shaving of the anterior chest, mice were warmed using a heat lamp. Short axis views of the left ventricle were captured at the level of the papillary muscles in 2D and M modes. Analysis was carried out offline and fractional shortening calculated as [LVEDD−LVESD]/LVEDD where LVEDD is left ventricular end diastolic diameter (measured at the tip of the mitral valve leaflets) and LVESD is left ventricular end systolic diameter.

Cardiovascular hemodynamics. We carried out simultaneous measurements of pressure and volume measurements using a specialized conductance catheter (Millar Instruments, Houston, Tex.). Male and female mice aged 10-14 weeks (apelin+/+, n=13; apelin−/−, n=12) were anesthetized with 1-2% isoflurane in oxygen (1.5 l/min). The internal jugular vein was cannulated with PE tubing and a 10% albumin solution infused at 5 μl/min. Mice were intubated and ventilated at a tidal volume of 200 μl at 100 breaths per minute (Harvard Apparatus, Holliston, Mass.). The right carotid artery was cannulated and the pressure-volume catheter inserted retrograde across the aortic valve along the long axis of the left ventricle. The temperature of the mice was constantly monitored by a rectal probe and they were maintained at 37° C. by a self regulating heating pad (Fine Science Tools, San Francisco, Calif.). The abdomen was then opened with a small transverse incision and the inferior vena cava was visualized just superior to the liver and inferior to the diaphragm. After baseline loops were recorded, occlusion parameters were recorded during and after three 5 second manual occlusions of the inferior vena cava.

Systolic blood pressure was recorded in conscious mice using a computerized, non-invasive tail cuff system (Visitech Systems, Stratham, N.H.).

Isolation of left ventricular myocytes. Adult ventricular myocytes were isolated from 12-14 week old apelin+/+ and apelin−/− mice based on previously published protocols. Briefly, mice were injected with heparin (100 IU/ml) and anesthetized with pentobarbital sodium (100 mg/kg IP). The heart was removed and retrogradely perfused at 37° C. with a calcium free solution (in mM, 120 NaCl, 14.7 KCl, 0.6 $KH_2PO_4$, 0.6 Na2HPO4, 1.2 $MgSO_4$-$7H_2O$, 4.6 $NaHCO_3$, 10 Na-HEPES, 30 taurine, 10 BDM, 5.5 glucose) for 4 min followed by an enzymatic digestion with collagenase (Worthington Biochemical Corporation, Lakewood, N.J.) 394 U/mg, 1.5 mg/ml). The digestion was initially performed in calcium free solution for 2 min and then CaCl2 was added to 50 μM final concentration for 6 additional min. Ventricles were cut into small pieces and were further digested by gently pipetting with plastic transfer pipettes for 3-5 min. Stop buffer (calcium free solution+$CaCl_2$ 12.5 μM+10% bovine calf serum (Hyclone, Logan, Utah)) was added and cell suspension was collected in a 15 ml tube and centrifuged at 350 rpm for 3 min. Myocytes were resuspended in stop buffer containing 100 μM CaCl2, rested for 2 min and then centrifuged at 350 rpm for 3 min. These steps were repeated using stop buffer with increasing CaCl2 concentrations until 1 mM was achieved. Experiments were performed with freshly isolated myocytes resuspended in a HEPES-buffered solution (in mM 1 CaCl2, 137 NaCl, 5.4 KCl, 15 dextrose, 1.3 MgSO4, 1.2 NaH2PO4, 20 HEPES, pH 7.4).

Myocyte shortening and relengthening. Cell contraction properties of myocytes were evaluated with a video-based sarcomere spacing acquisition system (SarcLen, IonOptix, Milton, Mass.). Rod-shaped myocytes with clear striation patterns and quiescent when unstimulated were chosen. Cells were placed in a culture chamber stimulation system (Cell MicroControls, Norfolk, Va.), mounted on an inverted microscope (Nikon TE2000U, Nikon, Melville, N.Y.) and electrically stimulated with suprathreshold voltage at 0.5 Hz and superfused with a HEPES-buffered solution at 25° C. Changes in sarcomere length were recorded and further analysis was performed using IonWizard software (IonOptix, Milton, Mass.).

Calcium transient measurements. A separate set of myocytes was loaded with 0.5 mM fura 2-acetoxymethyl ester Molecular Probes (Eugene, Oreg.) for 15 min. Cells were then washed and rested for an additional 40 min in order to allow the deesterification of the fura-2 ester. Myocytes were stimulated at 0.5 Hz and superfused with a HEPES-buffered solution at 25° C. Cells were excited at 340 and 380 nm, continuously alternated, at rates as high as 250 pairs/sec using a HyperSwitch system (IonOptix, Milton, Mass.). Background-corrected fura 2 ratios were collected at 510 nm. This ratio is independent of cell geometry and excitation light intensity, and reflected the intracellular calcium concentration.

Immunoblotting. Troponin I expression and Ser 23/24 phosphorylation state was measured by immunoblotting. Whole tissue lysates were obtained by homogenization of snap-frozen LV myocardium in lysis buffer. Samples were heated at 110° C. on a heat block for 15 minutes, cooled at room temperature and centrifuged for 10 minutes at 13,000 rpm. Supernatant was collected and total protein concentration was quantified using the Molecular Probes Quant-IT kit (Invitrogen, Carlsbad, Calif.). Samples were electrophoresed on Nupage 4-12% Bis-Tris gel (Invitrogen) and proteins were transferred to a PVDF membrane (Hybond-P, Amersham Pharmacia Biotech, Buckinghamshire, UK). Blocking was accomplished with 5% nonfat milk in TBST. Immunoblotting was performed using Troponin I and Phospho-Troponin I (Cardiac, Ser23/24) antibodies (Cell Signaling Technology, Danvers, Mass.) at 1:1000 dilutions and then using goat anti-rabbit IgG antibodies at 1:5000 dilution. Protein was visualized using the enhanced chemiluminescence method (ECL, Amersham).

Neurohormonal cardiomyopathy model. Apelin+/+ (n=10) and apelin−/− (n=10) mice received 7 day infusions of Angiotensin II (200 ng/kg/min) and isoproterenol HCl (15 mg/kg/day) (Sigma, St. Louis, Mo.) via Alzet micro-osmotic minipumps (100 μl, Durect Co., Cupertino, Calif.). Sham groups of apelin+/+ (n=3) and apelin−/− (n=3) received an infusion of saline. An additional fifth group of wild type animals (n=10) received two minipump infusions administered simultaneously: one pump with angiotensin II and isoproterenol, and the second pump with pyr-apelin-13 (2 mg/kg/day) (American Peptide, Sunnyvale, Calif.). All mice were age 12-14 weeks. At baseline, prior to pump implantation, animal weights were obtained and left ventricular function was assessed by echocardiography. Minipumps were explanted after 7 days, and following an additional 24 hours, mice were again weighed and ventricular function re-assessed by echocardiography. Mice were then sacrificed, organs harvested and protein lysates isolated for immunoblotting.

Analytical methods. Pairwise comparisons were made using Student's t test. One way analysis of variance was used in the event of multiple groups. Post hoc testing was according to the method of Fisher. Exact p values are stated in most cases. All data is presented in the text as mean, ±standard error of the mean (SEM). In most cases, data are presented with box plots, with the box representing the 25th-75th percentiles with the line in the box representing the median, and the whiskers showing the highest and lowest values.

Results

Figure 8:
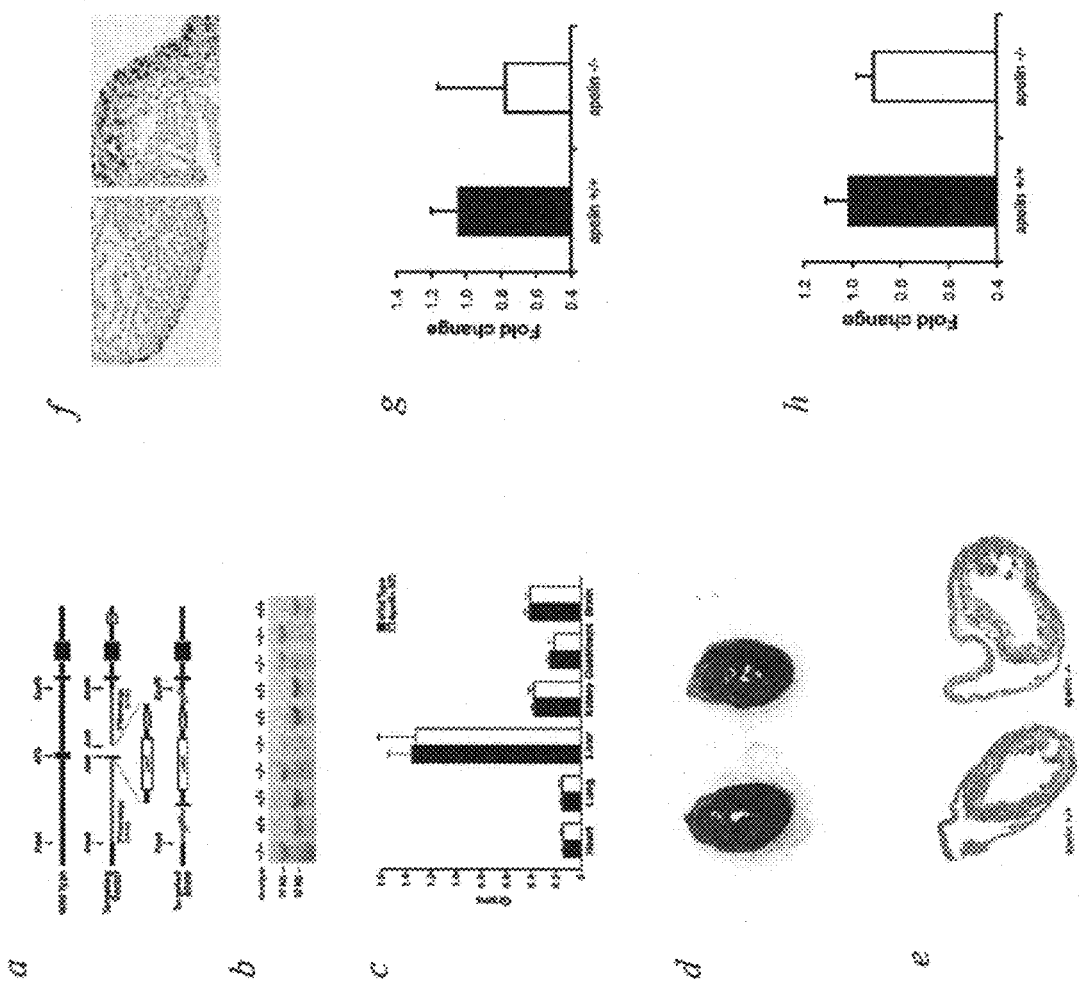
FIGS. 8A-8H. An apelin null mouse was created by gene targeting. (a) A construct encoding a nuclear targeted lacZ expression cassette was integrated by homologous recombination into the apelin locus, resulting in deletion of the first exon including the native ATG and leader peptide. Transfections were performed in 129SV/J embryonic stem cells, and targeted cells microinjected into C57BI/6J blastocysts. (b) Germline transmission of apelin targeted allele in male mice. Male agouti offspring of chimeric founder mice were evaluated by Southern blot with an apelin genomic probe. The wildtype allele migrates at 12 kb (+), and the targeted allele (□)at 17 kb. There is only one allele for apelin in these male mice since apelin is on the X chromosome.(c) Organs were removed from apelin knockout animals and littermate controls, and wet weights compared (d) Gross organ morphology was similar between knockout and wildtype animals. (e, f) Histological study of cardiac morphology revealed no differences between wildtype and apelin knockout animals (g, h) fold change in apelin$^{+/+}$ vs. apelin$^{-/-}$.

Apelin null mice show normal physiological development. Apelin null mice were generated using a construct which replaced the start codon and signal sequence of the apelin gene with a bacterial lacZ reporter gene (FIG. 8A-B). Knockout mice were viable and fertile and demonstrated a Mendelian pattern of inheritance with respect to the mutant allele. Northern blots and RT-PCR demonstrated no evidence of apelin RNA in the mutant mice. Post mortem inspection of major organs of 12 week old adult mice revealed no gross or histological abnormality. Organ weights were similar and histology revealed no gross microscopic differences. Cell counting of cardiac nuclei within pre-defined microscopy fields revealed no evidence of cardiac cellular hypertrophy.

Figure 9:
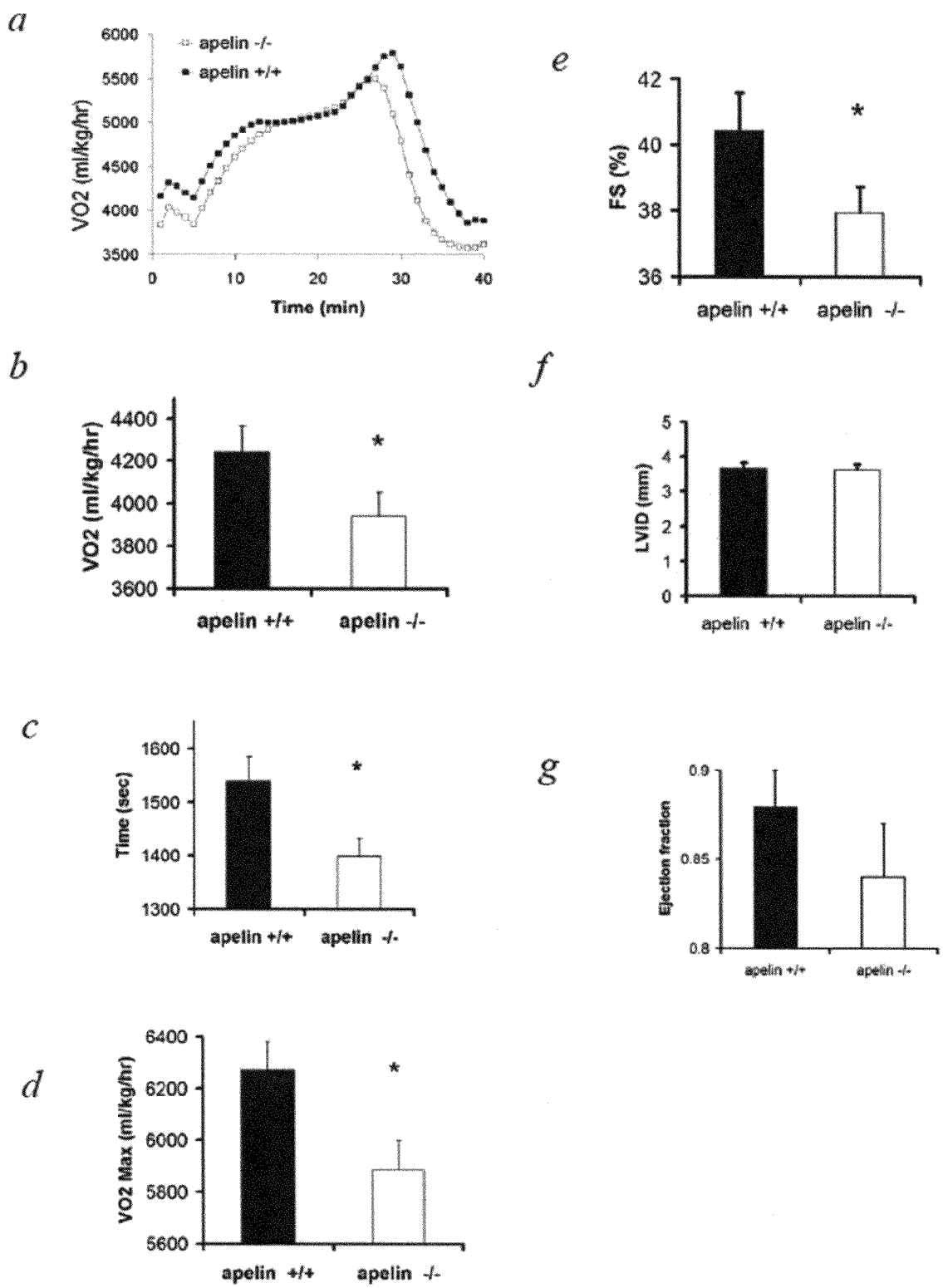
FIGS. 9A-9G. Apelin null mice have reduced exercise capacity, oxygen consumption, and load dependent contractility. (a) Averages of oxygen consumption (VO2) over time in apelin null (n=10) and wild type (n=10) mice during treadmill exercise. (b) Apelin null mice have decreased resting oxygen consumption. (WT: 4239.6±518, KO: 3943.7±365 ml/kg/hr; p=0.001) (c) Graded treadmill running reveals that apelin null mice have impaired exercise capacity. (WT: 1538.8±185, KO: 1398.8±118 seconds; p=0.034). (d) Apelin null mice have lower maximal oxygen consumption. (WT: 6269.2±464, KO: 5885.0±399 ml/kg/hr; p=0.033) (e) Apelin null mice have decreased load dependent contractility as measured by fractional shortening with echocardiography. (WT: 37.9±1.4%, KO: 40.4±1.4%, p=0.04, n=13 per group). (f) There was no change in left ventricular end diastolic dimension between the two groups. (WT: 0.365±0.015 cm KO: 0.361±0.015 cm, p=0.33). (g) Magnetic resonance imaging revealed a trend towards a decrease in ejection fraction in the apelin null mice. (WT: 83.9%, KO: 87.9%; p=0.23).

Apelin null mice have lower peak oxygen consumption and lower exercise capacity. Apelin null mice and their littermate controls underwent graded treadmill exercise. Mean oxygen consumption ($VO_2$) over time differed in the two strains of mice (FIG. 9A). Exercise capacity expressed both as external work (treadmill time in secs, FIG. 9B, p=0.034) and internal work ($VO_2$max, FIG. 9C p=0.033) was lower in mice without apelin. These changes were not explained by differences in body mass (p=0.6) or effort (tests were accepted only with a maximum respiratory exchange ratio greater than 1 and there was no difference in this maximum value between groups, p=0.3).

TABLE 3

|  | apelin+/+ | SEM | apelin−/− | SEM | P |
|---|---|---|---|---|---|
| Rest VO2 | 4240 | 498 | 3944 | 353 | 0.099 |
| Max VO2 | 6269 | 113 | 5885 | 115 | 0.033 |
| Treadmill time | 1539 | 44.87 | 1399 | 34.06 | 0.034 |
| Body weight | 25.7 | 0.8 | 26.3 | 0.9 | 0.6 |
| RER | 1.02 | 0.01 | 1.04 | 0.01 | 0.3 |
| FS (echo) | 44.5 | 1.2 | 42.8 | 0.8 | 0.7 |

Data from treadmill exercise testing; VO2 in ml/kg/hr, treadmill time in seconds, body mass in grams, RER in ratiometric units (respiratory exchange ratio, VCO2/VO2)

Imaging studies suggest a minimal decrease in load-dependent contractility. Changes in fractional shortening and ejection fraction are readily available and widely accepted measures of contractility in mammalian cardiovascular physiology. Echocardiography using a 13 Mhz probe revealed no significant difference in fractional shortening between the apelin null and wildtype mice (Table 3, FIG. 9D, p=0.04). Left ventricular end-diastolic diameter and ejection fraction were not different in the two groups (Table 3, p=0.33). Similar findings emerged from magnetic resonance imaging, where there was a decrease in mean ejection fraction but this difference was not significant.

Figure 10:
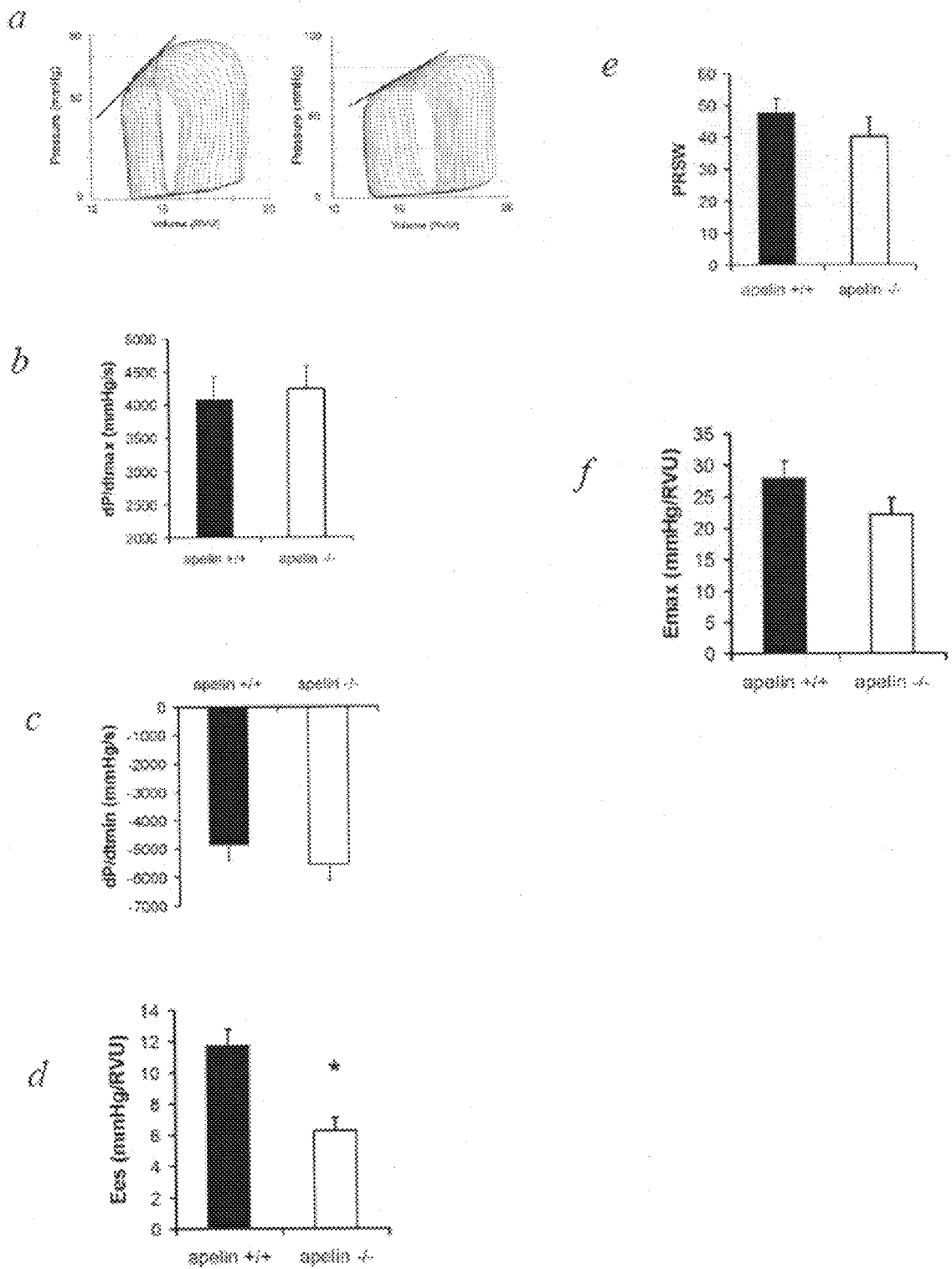
FIGS. 10A-10D. Apelin null mice have decreased intrinsic contractility as measured by load independent parameters. (a) Representative pressure volume loops of wild type (n=13) and apelin null (n=12) mice. The rate of rise (dP/dt max) (b) and fall (dP/dt min) (c) in pressure over time were not significantly different in the two groups. (d) However, there was significantly lower elastance (Ees) in the apelin null mice with a lower intercept as well as slope of the end systolic pressure volume relationship. (WT: 11.1±2.6, KO: 6.9±1.9 mmHg/RVU; p=0.00018). There were also trends towards decreased contractility in the apelin null mice in other load independent parameters such as (e) preload recruitable stroke work (WT: 44.1±11.6, KO: 36.5±12.8 mmHg×RVU) and (f) maximal elastance (WT: 25.3±7.1, KO: 20.9±5.9 mmHg/RVU; p=0.11).

Apelin null mice have decreased load-independent contractility. Since apelin may affect vascular resistance as well as cardiac contractility, we assessed load independent contractility using a conductance catheter which allows simultaneous assessment of pressure and volume. Compression of the inferior vena cava then allows pressure-volume relations to be assessed during systole and diastole across a wide range of loading conditions. For example, left ventricular elastance is the slope of a linear regression line fit to the end systolic pressure points across a range of loading conditions (FIG. 10A). Apelin null mice had similar heart rate and blood pressure under conditions of anesthesia and ventilation (Table 4). Similarly the rate of rise (FIG. 10B, p=0.75) and fall (FIG. 10C, p=0.3) of LV pressure was not different between groups. LV end-systolic elastance, however, was significantly lower in apelin null mice (FIG. 10D, p=0.0002). Other load independent derivative indices of contractility were lower in apelin null mice but these did not reach significance (pre-load recruitable stroke work, p=0.13; maximal elastance, p=0.11).

TABLE 4

|  | apelin +/+ | SEM | apelin −/− | SEM | p-value |
|---|---|---|---|---|---|
| Heart rate (bpm) | 424.2 | 11.1 | 424.5 | 14.1 | 0.99 |
| Systolic blood pressure | 66.6 | 3.3 | 67.5 | 2.0 | 0.84 |
| Diastolic blood pressure | 7.0 | 1.2 | 5.2 | 0.9 | 0.25 |
| End-systolic Volume (RVU) | 18.4 | 0.5 | 17.1 | 0.6 | 0.14 |
| End-diastolic Volume (RVU) | 20.4 | 0.6 | 19.3 | 0.9 | 0.28 |
| Stroke Volume (RVU) | 4.0 | 0.3 | 4.3 | 0.5 | 0.63 |
| Stroke Work (mmHg*RVU) | 199.8 | 19.8 | 229.2 | 37.3 | 0.46 |
| dPdt max (mmHg/sec) | 4082 | 349.0 | 4246 | 349.1 | 0.75 |
| dPdt min (mmHg/sec) | −4864 | 403.4 | −5562 | 535.9 | 0.30 |
| Tau (Glantz method) (msec) | 10.8 | 2.6 | 8.2 | 0.6 | 0.41 |
| Maximal Power (mWatts) | 1.2 | 0.1 | 1.3 | 0.2 | 0.45 |
| PAMP (mWatts/RVU^2) | 29.3 | 3.7 | 34.6 | 3.8 | 0.34 |
| ESPVR (mmHg/RVU) | 11.1 | 0.7 | 6.9 | 0.6 | 0.0002 |
| ESPVR intercept | 10.7 | 0.9 | 6.6 | 1.3 | 0.01 |
| PRSW | 44.1 | 3.2 | 36.5 | 3.7 | 0.13 |
| PRSW intercept | 14.2 | 0.7 | 12.8 | 0.7 | 0.14 |
| dPdt - EDV (mmHg · s/RVU) | 411.2 | 59.3 | 329.1 | 58.8 | 0.34 |
| dPdt - EDV intercept | 7.1 | 1.4 | 7.8 | 3.4 | 0.83 |
| slope-EDPVR (mmHg/RVU) | 2.3 | 0.4 | 1.9 | 0.4 | 0.56 |
| int-EDPVR | −35.7 | 5.7 | −33.4 | 7.8 | 0.81 |
| Emax | 25.3 | 2.0 | 20.9 | 1.7 | 0.11 |

Data from pressure-volume catheter measurements, units as indicated.

Figure 11:
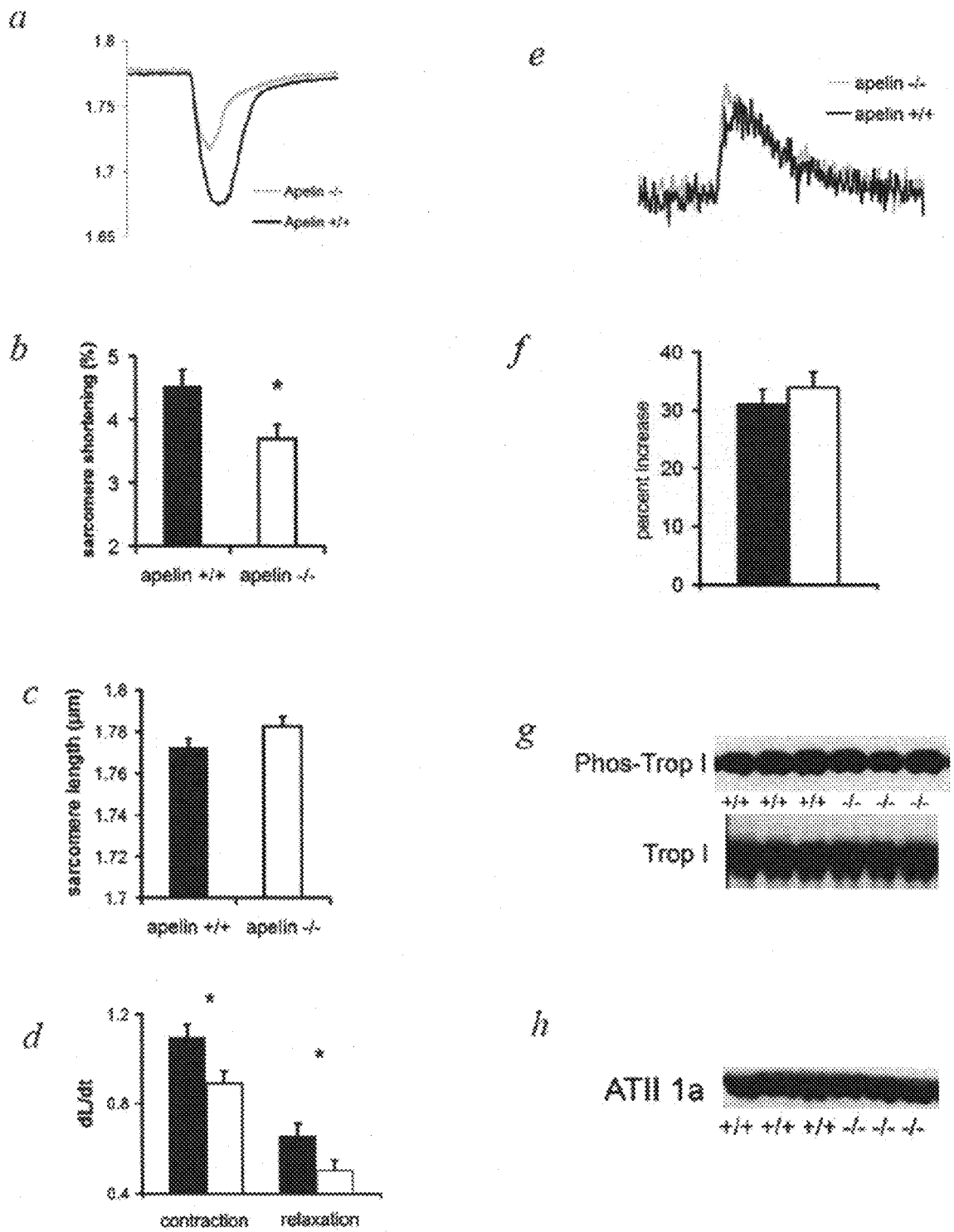
FIGS. 11A-11H. Apelin null cardiomyocytes show decreased contractile function, but similar intracellular calcium kinetics. (a) Representative raw loop of sarcomere function demonstrating decreased contractile function of myocytes from the apelin null mice. (n=40 cells per group) (b) Sarcomere shortening was significantly decreased in the apelin null mice. (c) There was no difference in sarcomere starting length between groups. (d) The speed of contraction and relaxation (dL/dt) was also significantly reduced in the apelin null myocytes. (e) Calcium transients were assessed comparing myocytes from the apelin transgenic and wild type mice. (n=16 cells per group) (f) No significant difference was found between groups in the intracellular increase in calcium level with contraction. (g) Phosphorylation levels of Troponin I at serine residues 23-24 were similar in the apelin null mice and the wildtype mice at basal conditions. (h) Angiotensin II Type la (ATI) receptor levels were also similar between the two groups. *, P<0.05.

Apelin knockout suggests autocrine myocardial signaling involving calcium sensitization. To identify any effect of loss of autocrine apelin signaling, we isolated LV myocytes from apelin null mice (n=40 cells) and their littermate controls (n=40 cells) and quantified the dynamics of sarcomere shortening and calcium fluorescence under field stimulation. Myocytes isolated from apelin null mice demonstrated clear deficits in their sarcomeric function (FIG. 11A-C). Sarcomere shortening was less (FIG. 11A-B, WT: 4.520±0.264%, KO: 3.685±0.232%, p=0.02) with no difference in starting sarcomere length (WT: 1.77±0.004 μm, KO: 1.78±0.005 μm, p=0.1). There were also differences in the rate of lengthening and relaxation, with myocytes from apelin null mice exhibiting a lower maximum velocity of shortening and lengthening (FIG. 11C: dL/dt-contraction: WT: 1.097±0.059, KO: 0.892±0.051 p=0.01; dL/dt-relaxation: WT: 0.655±0.056, KO: 0.506±0.044 p=0.04).

To determine a mechanism for these changes, we assessed calcium fluorescence in a separate group of apelin null (n=16) and littermate control (n=16) cells. There was no difference in the change in calcium level during contraction in apelin null myocytes compared with controls (FIG. 11D, E, WT: 31.00±2.59%, KO: 33.99±2.54%, p=0.4). Troponin I phosphorylation at serine 23-24 was assessed by immunoblotting of left ventricular lysates from the apelin null mice and control mice and found to be similar between groups (FIG. 11F). The similar calcium transients in the apelin null animals compared with controls suggest an autocrine control of myofilament calcium sensitivity, while the similar troponin I phosphorylation suggests a troponin independent mechanism for apelin, likely via intracellular alkalinization.

Apelin infusion rescues neurohormonal heart failure. We investigated the effect of apelin deletion in a neurohormonal model of heart failure, using hormonal infusions with angiotensin II and isoproterenol in the apelin null and wild type mice. Both the wild type and apelin null mice exhibited severe heart failure with significant decline in fractional shortening after week long infusions by osmotic minipump (FIG. 12A, WT (pre): 40.4±1.2%, WT (post): 28±1.1%, p<0.001; KO (pre): 37.9±0.8%, KO (post): 26.9±1.1%, p<0.001).

A sham group of wild type mice and apelin null mice that were given saline had normal cardiac function after infusions. In accordance with downregulation of apelin and APJ in severe heart failure previously reported by our group and others, no significant difference in heart failure severity was seen between the wild type and knockout animals, as measured by echocardiographic parameters of fractional shortening and LV dimensions. However, when apelin was concomitantly infused in a group of wild type mice along with catecholamine infusion, the severe heart failure phenotype was completely abrogated, with maintenance of normal contractility (FIG. 12B, WT-Apelin (pre): 41.8±1.3%, WT-Apelin (post): 42.6±1.3%, p<0.001 compared with fractional shortening of WT and KO groups post catecholamine infusion).

To gain insights into the mechanism of apelin action in this model, troponin I phosphorylation at serine 23-24 was assessed by immunoblotting and found to be significantly decreased in both the wild type and apelin null mice after induction of heart failure compared with the control mice (p<0.01, FIG. 12D). In the combined apelin and catecholamine treated group with rescue of heart failure, troponin I serine 23/24 phosphorylation was increased significantly compared with the apelin null mice with neurohormonal heart failure (p<0.01, FIG. 12C).

An apelin null mouse model was created and studied to better understand the role of the apelin-APJ pathway in physiological and pathophysiological conditions. These studies suggest that the apelin-APJ pathway has a modest tonic effect on basal cardiovascular control, and respond to perturbations in perfusion. Apelin null mice have lower exercise capacity as evidenced by decreased treadmill time. They also exhibited lower maximal oxygen consumption with no differences in effort or body mass. These data imply that the apelin null mice have a decreased ability to augment cardiac output in response to an exercise (preload) challenge. This decrement in functional capacity was associated with no significant decrease in noninvasive measures of cardiac performance such as ejection fraction, suggesting that apelin exhibits a differential effect on contraction at different levels of preload. Since the end systolic pressure volume relationship is linear, this implies a change in LV elastance. To test this idea, we used pressure volume measurements to assess in vivo function at varying preload. We found that apelin null mice had a clearly significant reduction in left ventricular elastance with a lower intercept, and exhibited trends toward decreased preload recruitable stroke work and maximal elastance. Taken together, these data suggest a downshift in 'load independent' contractility in the apelin null mice. The reduction in the intercept helps explain the lack of significant echo and MRI findings with respect to fractional shortening at normal preload.

Myocardial cells have been shown to express both apelin and its high affinity APJ receptor, and APJ has been localized to the nucleus in other cell types, prompting experiments to address a possible autocrine pathway and its potential mechanism of action. Employing isolated single left ventricular myocytes from apelin null mice, we demonstrated impaired sarcomeric function with no change in baseline sarcomeric length. There were also changes in the rate of sarcomere contraction and relaxation suggesting overall that apelin increases myocyte contractility in an autocrine fashion.

To determine whether apelin-APJ increased contractility via an enhanced calcium transient, we measured intracellular calcium concentration via autofluoresence in contracting left ventricular myocytes from apelin null mice and their littermate controls. Despite a clear difference in contractility, there was no significant difference in intracellular calcium baseline level or contraction excursion suggesting that loss of apelin affects myofilament sensitivity or cross-bridge cycling. These observations indicate that exogenous apelin does not increase calcium transients, but activates the sarcolemmal $Na^+/H^+$ exchanger and increases intracellular pH, suggesting increased myofilament sensitivity to calcium as a mechanism for inotropy. Thus both autocrine and paracrine apelin-APJ pathways may regulate cardiac function.

To further investigate therapeutic use of apelin in heart failure, we used a neurohormonal model of heart failure in apelin null mice and their littermate controls. The model was robust in our hands as demonstrated by dramatic decreases in fractional shortening. Strikingly, when exogenous apelin was administered concurrent with angiotensin and isoproterenol, the heart failure phenotype was abrogated completely. While serine 23/24 troponin I phosphorylation was reduced with heart failure and further reduced in the apelin null mouse, exogenous apelin partially restored the phosphorylation state on a heart failure background in the wild type mice. Reduced troponin I phosphorylation in heart failure has been shown previously and is thought to relate to downregulation of beta receptors and cellular PKA. It is believed that this leads to decrements in cross-bridge cycling while increasing myofilament calcium sensitivity. Phosphorylation at that residue via apelin mediated rises in PKC may restore cross-bridge cycling.

These data establish an endogenous role for apelin-APJ in normal cardiac function. Rescue of the neurohumoral heart failure model in these studies demonstrates that therapeutic activation of this pathway has a salutary effect in heart failure. The use of this pathway for medical benefit provides the benefits of balanced arterial and venous vasodilatation, load independent inotropy via calcium sensitization, and angiotensin II and vasopressin antagonism.

Example 8

Apelin Signaling Antagonizes Angiotensin Mediated Exacerbation of Atherosclerosis It was investigated whether apelin can antagonize or counteract the vascular disease-promoting actions of AngII. In the apoE atherosclerosis model apelin was shown to decrease angiotensin-mediated increase in atherosclerosis burden, and to block aortic aneurysm formation and rupture. In a vein graft model, apelin inhibited the AngII-mediated increase in neointimal formation. In both of these in vivo models, apelin was shown to significantly inhibit superoxide formation in the vessel media, through blocking of smooth muscle cell NADPH oxidase activity. In vitro studies provide evidence that apelin can directly block AngII signaling, and suggest this inhibition is mediated at least partly at the receptor level.
Results Apelin inhibits the AngII mediated exacerbation of atherosclerosis in murine models. To test the effect of Apelin on vascular remodeling we used well described mouse models of atherosclerosis, abdominal aortic aneurysm formation, and vein graft neointimal hyperplasia. Total cholesterol, triglyceride levels, and body weights were similar among the four groups. We first quantified atherosclerosis in the descending aortas of experimental animals. ApoE-KO mice treated with apelin developed significantly less atherosclerosis than saline treated controls (66% reduction, P=0.01, FIG. 13a). Infusion of AngII increased descending aorta atherosclerosis compared to saline treated control mice (82%, P=0.05, FIG. 13a). However, co-infusion of Apelin with AngII markedly reduced total lesion burden to levels similar to Apelin treated mice (75% reduction, P=0.01, FIG. 13a), indicating that at least some of the beneficial effects of apelin were mediated through antagonism of AngII mediated pathways. We next quantified aortic root atherosclerosis. There was a trend towards a reduction in atherosclerotic burden in apelin treated mice compared to saline treated controls (25%, P=0.07, FIG. 13b).

To investigate the effect of apelin on vascular remodeling we investigated AAA formation in experimental animals using a well described AngII induced AAA formation model. We did not observe AAA formation in saline or apelin treated mice, whereas in those animals infused with AngII 92% (11/12) developed an AAA within 4 weeks. The addition of apelin to AngII infused mice dramatically attenuated this effect, reducing the incidence of AAA formation to 8% (1/12, P<0.001, FIG. 13c).

To test the effect of apelin on vascular injury induced remodeling, we quantified vein graft wall and neointimal area 4 weeks following vein graft surgery, a model characterized by acute endothelial loss, intimal hyperplasia and endothelial regeneration. Mean vessel wall (42%, P=0.02) and neointimal area (77%, P<0.001) were significantly reduced in apelin treated mice compared with saline treated controls (FIG. 13d). Infusion of AngII increased both vein graft wall (33%, P=0.01) and neointimal area (25%, P=0.04) compared to saline treated control mice (FIG. 13d). However, addition of apelin to AngII treated experimental animals rescued this phenotype, reducing mean vessel wall area (34%, P=0.03) to levels of saline treated controls and neointimal area (71%, P<0.001) similar to apelin treated mice (FIG. 13d). Interestingly, the beneficial effects of apelin on vascular remodeling were most appreciable on neointimal formation. These findings highlight an important role for apelin-APJ in regulating vascular remodeling in conditions of moderate (ApoE-KO) and high (AngII infusion) oxidative stress.

Figure 14A:
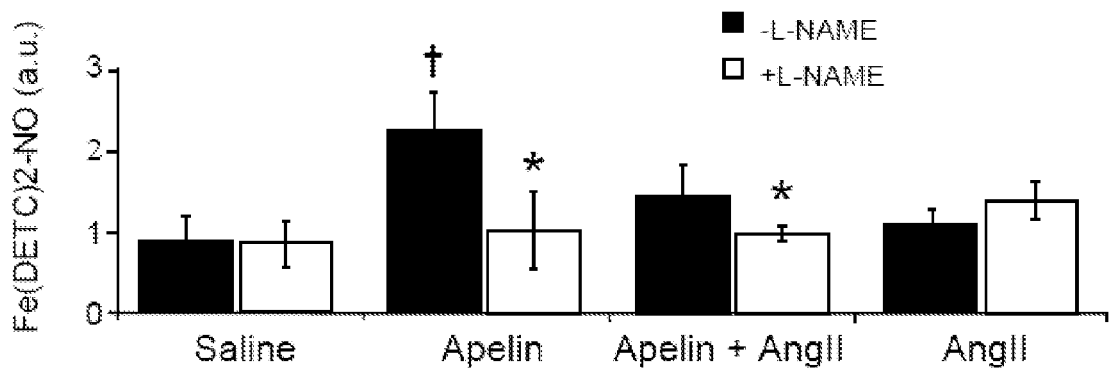
FIGS. 14A-14C. Apelin increases vascular wall NO bioavailability and suppresses disease-related superoxide production. a) Electron paramagnetic resonance (EPR) spectroscopy was employed to measure NO in lung homogenates of apoE knockout mice. There was increased NO production in the apelin group, and improved eNOS coupling in the AngII treated animals. Shown are means and SEM. b) Superoxide production was measured in aortic tissue of apoE knockout mice by lucigenin-enhanced chemiluminescence. There is a significant (p<0.05) decrease in apelin treated apoE knockout mice compared to control and apelin infusion. AngII produced a significant 10-fold increase in superoxide that was abolished by apelin. Graphs represent means and SEM. c) Cellular superoxide production was evaluated with dihydroethidium oxidative fluorescence microtopography. Infusion of apelin reduced aortic SO production in saline and AngII treated groups. Most of the SO is generated in the media, and is produced by NADPH oxidase since it is blocked with apocynain. Representative aortic sections are shown. Graphs represent means and SEM.
Figure 14B:
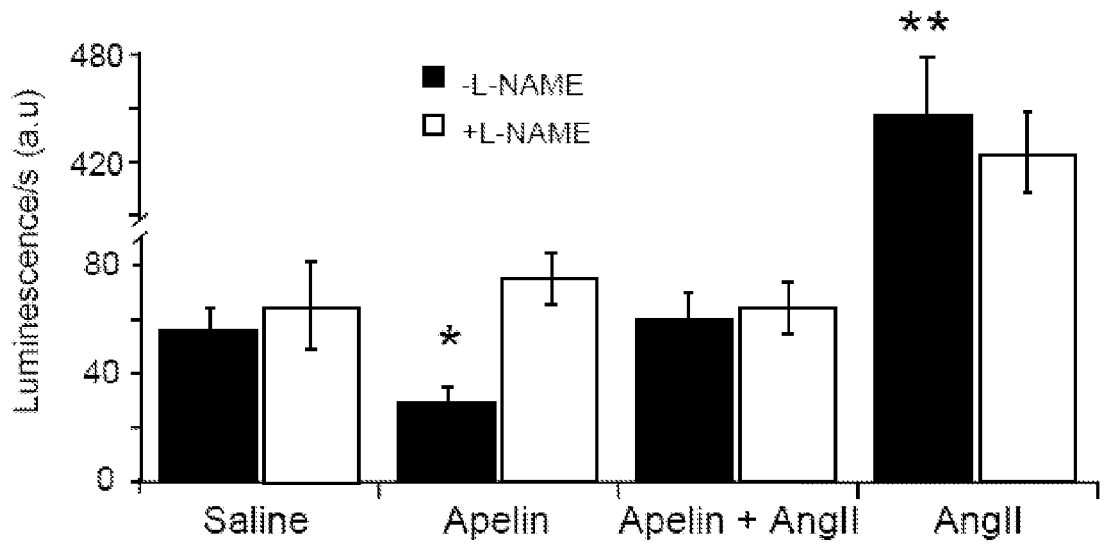
Figure 14:
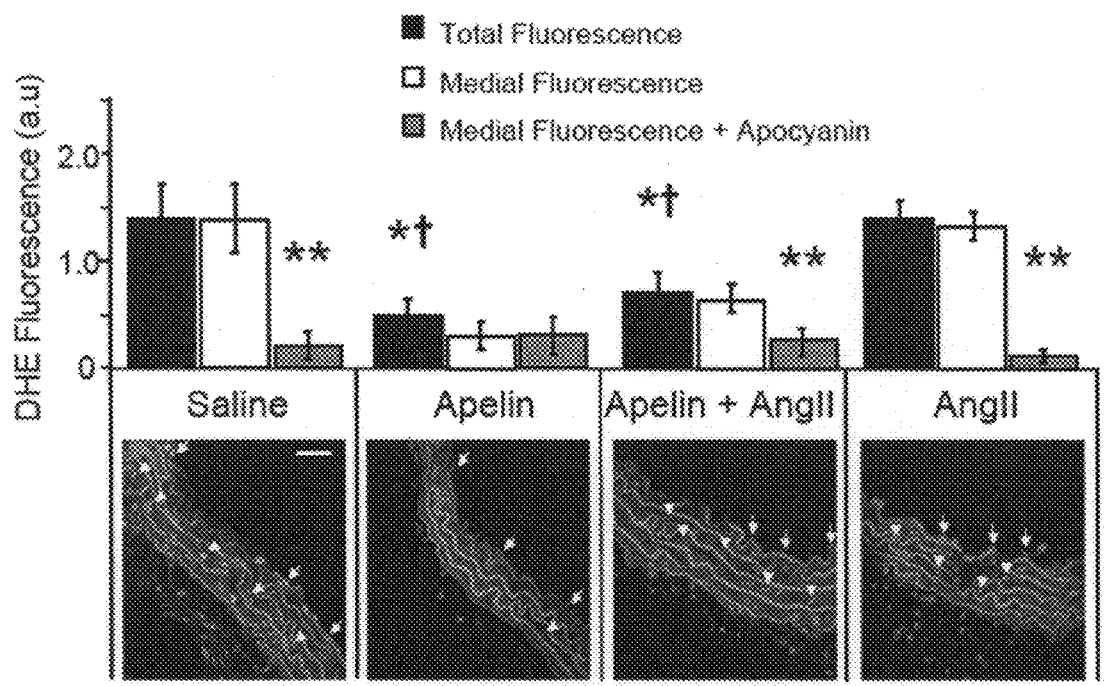

Apelin regulates production of reactive oxygen species in the vessel wall media. In keeping with previous reports indicating that the apelin-APJ pathway may counter-regulate NO-AngII pathways, and our findings of reduced atherosclerosis, AAA formation and vascular remodeling, we next investigated NO production in experimental animals. Net NO bioavailability, measured using Fe-DETC EPR, was significantly increased by approximately two-fold in apelin treated mice (FIG. 13a). Addition of the eNOS inhibitor L-NAME significantly reduced net NO bioavailability to levels similar to saline and AngII treated mice, indicating the source of the NO as the endothelium (FIG. 14a). Importantly, although there was no detectable difference in net NO bioavailability, addition of L-NAME in the AngII+apelin group also reduced NO bioavailability to basal levels (FIG. 14a), suggesting that apelin induced endothelial NO synthesis despite high levels of oxidative stress induced by AngII. We next investigated whether the differences in NO production were the result of changes in eNOS protein expression in apelin treated animals. We found no difference in eNOS protein levels in aortas from our experimental animals, indicating that any differences in NO production was not simply the result of changes in eNOS protein expression (FIG. 14b). Although eNOS protein levels may be reduced in endothelial cells overlying advanced atherosclerotic plaques, eNOS protein may remain normal, despite marked endothelial dysfunction, in pre-atherosclerotic states such as diabetes, experimental heart failure or hypertension.

In keeping with our finding of increased NO bioavailability in apelin treated mice, we next investigated superoxide formation in experimental animals. We observed striking differences in NOS dependent superoxide generation in the four groups. Total vascular superoxide production, by lucigenin-enhanced chemiluminescence was almost 50% lower in apelin treated mice aortas compared with saline treated controls (FIG. 14c). AngII infusion stimulated a 10-fold increase in total chemiluminescence, which was abolished by the addition of apelin (FIG. 14c). When aorta from saline, AngII or AngII+apelin treated animals were incubated with the eNOS inhibitor L-NAME, total superoxide levels were not significantly different, suggesting that the endothelial contribution to superoxide was small. However, incubation of aorta from apelin treated mice with L-NAME led to a 2-fold increase in total superoxide production, indicating that under basal conditions the endothelium in apelin treated mice was producing NO capable of scavenging superoxide.

Figure 15:
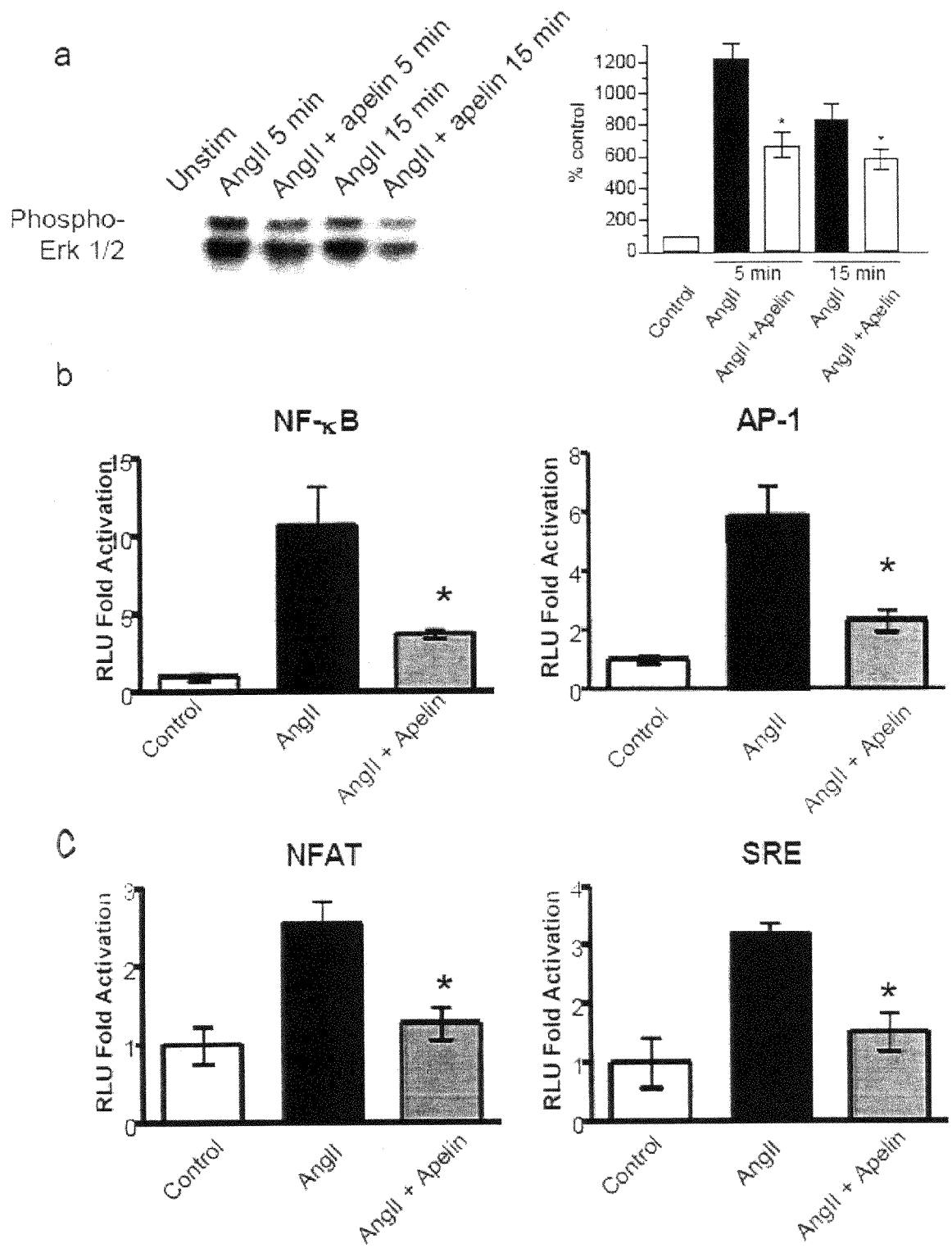
FIGS. 15A-15C. Apelin blocks AngII cellular signaling: a) Apelin treatment of AngII stimulated RASM decreased Erk1/2 phosphorylation. Graphs represent means and SEM. b) Reporter constructs representing AngII signaling pathways showed decreased activation when cells were treated with apelin. Graphs represent means and SEM. RLU, relative light units. c) NFκB activation stimulated by TNF-α and $H_2O_2$ was not affected by apelin treatment. Graph represents means and SEM.

To confirm the chemiluminescence findings and investigate the cellular source of superoxide in the aortas of experimental animals we measured superoxide production using dihydroethidium oxidative fluorescence microtopography. Total aortic fluorescence was 3-fold lower in apelin treated mice compared with saline treated controls (FIG. 14d). In contrast to the large increase in chemilluminscence in the AngII treatment group, aortic fluorescence in AngII infused animals was similar to saline treated controls, suggesting that superoxide generation was being produced by most cells, however at a greater rate in AngII treated animals. Addition of apelin to AngII treated mice significantly reduced aortic superoxide production compared to mice treated with AngII alone (FIG. 14d). When we quantified the source of superoxide generation we found the vast majority was being produced in the media of the aortic wall, with only a small proportion from the endothelial monolayer. These findings were consistent with the chemiluminescence findings, where incubation of the aorta with L-NAME produced a minimal effect on total chemiluminescence. As it is well established that AngII stimulates superoxide production in vascular smooth muscle cells through NADPH oxidase, we hypothesized that the apelin mediated reduction in superoxide was derived from NADPH oxidase. Incubation of aortic sections from saline, AngII and apelin+AngII treated mice with the NADPH oxidase inhibitor apocynain dramatically reduced total medial fluorescence (FIG. 15d). Interestingly we did not find this effect following incubation of aortic sections from apelin treated mice. Together, these findings suggest that the beneficial effect of apelin on atherosclerosis, AAA formation and vascular remodeling are mediated, at least in part, by blocking vascular smooth muscle cell NADPH oxidase derived superoxide formation.

Apelin regulates AngII mediated nuclear signaling in cultured cells. To further investigate the mechanism by which apelin inhibits the atherosclerosis-promoting actions of AngII, we evaluated the effect of apelin on AngII nuclear signaling. We first evaluated the phosphorylation of Erk 1/2 kinases with AngII stimulation. When RASM were co-transfected with both AT1R and APJ receptors, the degree of Erk phosphorylation due to AngII was significantly decreased compared to AT1R transfected cells alone (FIG. 15a). This difference was seen at both 5 minutes and 15 minutes after stimulation. We next assessed known transcriptional targets of AngII stimulation using luciferase reporter constructs with the NFκB, NFAT, AP-1 and SRE concensus response sequences. HEK-293 cells were co-transfected with an AT1 expression construct and reporter plasmids, and stimulated with AngII, apelin, or both peptides (FIG. 15b). With each reporter AngII produced a significant increase in transcription, and this increase was abrogated when cells were also treated with apelin. To investigate whether the observed apelin inhibitory effect on nuclear signaling showed specificity for AngII stimulation, we investigated the effect of apelin on TNF-α and $H_2O_2$ signaling (FIG. 15c). In neither case did apelin diminish transcription of the NFκB reporter construct. Finally, we performed competitive ligand binding experiments in HEK-293 cells with fluorsceine-labeled AngII, to verify that results in these experiments were not simply due to apelin competing for AngII binding. While unlabeled AngII was able to compete for FAM-tagged AngII, unlabeled apelin did not compete for binding, verifying that the ability of apelin to block AngII signaling is mediated through another receptor, presumably APJ, which is expressed at low levels on these cells.

Figure 16:
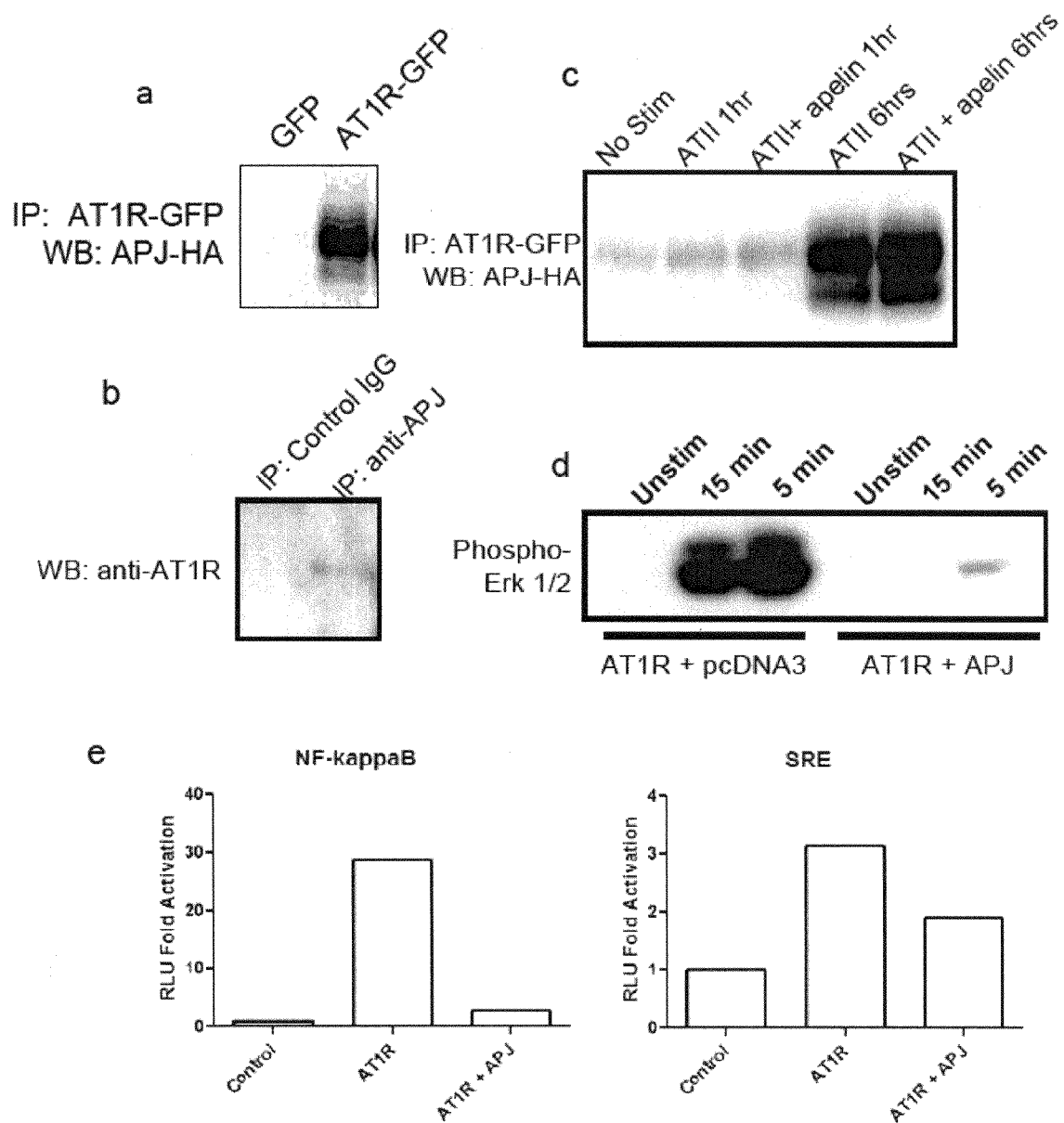
FIGS. 16A-16E. Direct interaction of AngII and apelin receptors regulates AngII signaling. a) Immunoprecipitation of AT1R with GFP tag, followed by western blot to detect APJ with HA tag suggests recombinant proteins are associated on the cell surface. b) Immunoprecipitation of APJ from lysates of pulmonary smooth muscle cells and western blot of AT1R suggests direct in vivo interaction of native receptors. c) Immunoprecipitation of AT1R and blotting of APJ was employed to show increased association in presence of AngII (ATII). d) Western blotting of cells transfected with AT1R alone or with APJ revealed decreased phosphorulation of Erk1/2, in cells expressing APJ. e) NFκB and SRE reporter constructs transfected with AT1R or AT1R plus APJ showed decreased signaling when APJ was expressed with AT1R. Graphs represent means and SEM. RLU, relative light units.
Figure 17:
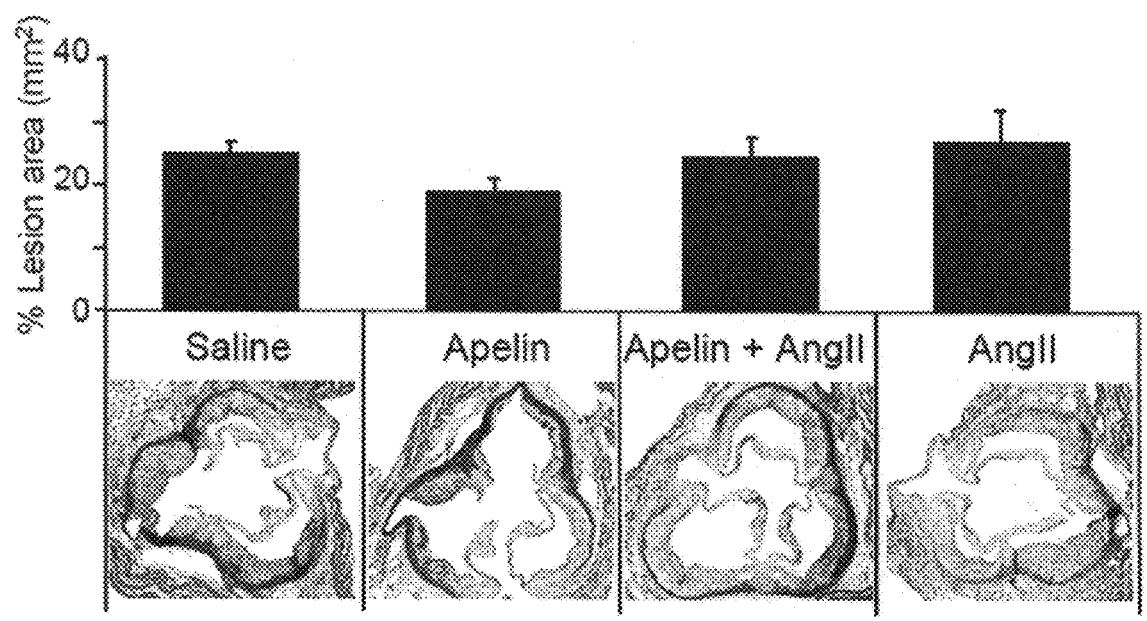
FIG. 17. Apelin and AngII do not alter the progression of atherosclerosis in aortic root of apoE knockout murine model of vascular disease. Apelin and AngII were administered by osmotic minipump during high fat diet exposure.
Figure 18:
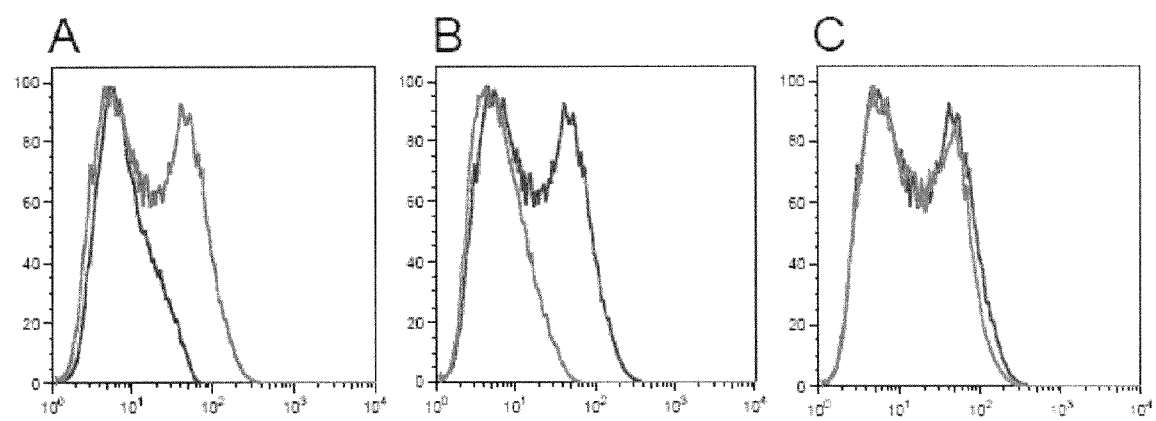
FIGS. 18A-18C. Apelin does not compete with AngII for binding to the primary AngII receptor AT1R. a) FAM-labeled AngII (10 nM) binds to cells transfected with AT1R (blue curve) but not to cells with control vector transfection (blue curve). b) Unlabeled AngII (100 nM) competes for binding of FAM-AngII (blue curve), compared to FAM-AngII (10 nM) in absence of unlabeled AngII (red curve). c) Unlabeled apelin (100 nM) does not compete for binding to AT1R (blue curve) and is similar to FAM-AngII (10 nM) binding in absence of apelin (red curve).

Apelin and AngII receptors interact in vitro and in vivo. Using expression constructs for AT1R tagged with green fluorescent protein (GFP) and APJ receptor tagged with hemagluttinin (HA) peptide, we transfected HEK-293 cells to assess for receptor heterodimerization. We performed immunoprecipitation using anti-GFP antibody, followed by immunoblotting using anti-HA antibody. We found co-immunoprecipitation of the APJ receptor in the presence of AT1R-GFP but not in cells that were transfected with GFP control vector (FIG. 16a). In addition, we identified a high molecular weight species representing APJ receptor homodimerization.

We next determined whether AT1R and APJ heterodimerization occurs between endogenously expressed proteins. Pulmonary artery smooth muscle cells were found to express high levels of both receptors by real-time RT-PCR analysis. Using whole cell lysates from these cells, we performed immunoprecipitation assays using anti-AT1R antibody and control non-specific immunoglobulin. Subsequent immunoblotting was performed using anti-APJ antibody. We identified a protein band corresponding to APJ only when immunoprecipitation was performed with anti-AT1R antibody (FIG. 16b). We also assessed the effect of ligand stimulation on receptor heterodimerization. We co-transfected AT1R and APJ receptors and treated with either AngII alone or AngII with apelin. We found that stimulation of the transfected cells with AngII significantly enhanced receptor-heterodimerization after 1 and 6 hours of treatment (FIG. 16c). Addition of apelin did not affect the AngII induced receptor heterodimerization.

In a final set of experiments we investigated the effect of the APJ receptor on AngII signaling. One study evaluated the phosphorylation of Erk1/2 in HEK293 cells expressing the AT1R alone, or AT1R plus APJ. Phosphorylation was dramatically reduced at both 5 and 15 minute timepoints when apelin was introduced (FIG. 16d). Additional studies investigated nuclear reporter gene expression in cells expressing AT1R alone, or AT1R plus APJ. A construct encoding AT1R was transfected with a vector control construct, or in conjunction with an APJ receptor construct, into HEK-293 cells. Robust reporter stimulation was noted with the NFκB and SRE reporter constructs with AngII stimulation in cells that were expressing AT1R alone, but was markedly diminished when APJ was also expressed (FIG. 16e).

It is now generally accepted that AngII stimulates the production of growth factors, cytokines, chemokines, and adhesion molecules, which promote processes such as cell growth, apoptosis, fibrosis, and inflammation in the diseased vessel wall. These activities of AngII are thought to directly support the pathogenesis of atherosclerosis, and blocking this pathway with ACE inhibitors has been shown to reduce cardiovascular events in patients with multiple risk factors for atherosclerosis. In addition to the complex regulation afforded by the processing of the angiotensin peptides and existence of multiple receptors, RAS actions are further modulated by other peptide stimulated signaling pathways, including the bradykinin and nitric oxide pathways. Experiments reported here provide evidence for antagonism of the atherosclerosis-promoting actions of the RAS by another peptide signaling pathway, the apelin-APJ pathway.

These data show that apelin blocks a spectrum of AngII-mediated exacerbations of atherosclerosis in the apoE knockout model, including increasing the burden of atherosclerosis in the descending aorta, promoting the development and rupture of aortic aneurysms, as well as increasing vein graft neointima formation and remodeling. These endpoints represent a number of pathophysiological processes that have been attributed to AngII in the setting of vascular wall disease. A common theme in each case is the AngII mediated increase in reactive oxygen species. The related decrease in NO availability, and the inflammatory consequences of increased ROS signaling in vascular wall cells are thought to be intimately involved in the disease process.

Previously, the actions of apelin in the vessel wall had been focused on the endothelium and the eNOS-dependent production of NO, but these studies also suggest an important novel role for apelin in blocking AngII mediated ROS production in vascular SMC. The mechanism for apelin mediated decreases in atherosclerotic disease might be a function of increased NO production, and indeed, experiments reported here show that apelin can increase eNOS production of NO in the apoE model, significantly extending previous work. Although there was no significant increase in net NO bioavailability when apelin was added to the model along with exogenous AngII, there did appear to be a reduction in uncoupling of eNOS, as there was a decrease in NO levels when L-NAME was added to the apelin+AngII samples, compared to an increase when L-NAME was added to the AngII alone samples. A new finding in these experiments is the dramatic reduction in AngII-mediated ROS production by smooth muscle cells in the media. AngII is well known to stimulate the synthesis of ROS through activation of NADPHoxidases, and the signaling mechanisms mediating this effect in SMC have been investigated. The proinflammatory actions of the ROS in the vessel wall have been linked to fundamental processes that are felt to be critical to development of atherosclerosis, including the expression of leukocyte adhesion molecules. This unexpected action of apelin to counteract the ROS stimulating actions of AngII appear to be a direct effect of apelin on the SMC. While APJ has been identified on some vascular SMC, and there is some information regarding signaling, downstream of APJ in cultured SMC, little is known regarding the physiological role of this pathway in vascular SMC.

In vitro experiments were aimed at providing insight into the mechanism by which apelin stimulation of SMC might block AngII mediated ROS production. We performed ligand binding studies with the AngII AT1A receptor, and found that apelin could not compete with AngII for binding to this receptor, and could not be simply serving as a receptor blocker. Experiments investigating known AngII activated pathways showed decreased AngII signaling to the nucleus, as assessed by protein phosphorylation assays and reporter gene expression assays. Given that a number of AngII downstream signaling pathways were blocked by apelin, and that apelin did not block activation of these pathways by other stimuli such as TNF-α and $H_2O_2$, it appeared likely that cross-talk between the AngII and apelin pathways was at a proximal point in the signaling cascades.

In summary, data presented here establish that apelin can block a number of AngII-related pathological processes associated with atherosclerosis in disease models, suggesting a role for the apelin-AP pathway in human vascular disease. Data in the apoE model further establishes the role of apelin in regulation of NO bioavailability and eNOS coupling. An important new finding is the regulation of AngII mediated superoxide production by SMC in the vascular media. These data suggest a more central role for apelin-APJ in SMC biology. We have established that the apelin-APJ pathway can directly regulate AngII signaling, and provided evidence that receptor heterodimerization can be one mechanism for crosstalk between these pathways. Through the combined mechanisms of promoting NO bioavailability and blocking AngII disease related functions such as superoxide production, the apelin-APJ pathway is positioned to be a primary determinant of atherosclerotic vascular disease.

Methods

Animals. Mice were maintained in temperature-controlled (20° C. to 22° C.) environment with a 12-hour light-dark cycle. Sterile water and standard chow diet were available ad libitum. All mice were C57BL/6J ApoE-KO male mice (Jackson Laboratories, Bar Harbor, Mich.) between the ages of 8-12 weeks. Four groups of ApoE-KO mice receiving 4 week infusions with 2-mL osmotic minipumps (Alzet Osmotic pumps, Cupertino, Calif., model 2002), implanted subcutaneously according to the manufacturers instructions, were compared; Saline infusion, Apelin-13 infusion (2 mg/kg/day), Apelin (2 mg/kg/day)+, AngII (1.4 mg/kg/day) infusion, or AngII infusion (1.4 mg/kg/day). Animal procedures were carried out in accordance with the Institutional Review Board Guidelines at Stanford University.

Abdominal aortic aneurysm formation, sudden death and vein graft procedure. In the AngII infusion model of AAA formation, infusion of AngII in ApoE-KO male mice results in AAA formation in 90% to 100% of animals. Abdominal aortic aneurysm was defined as ≧50% enlargement of the maximal abdominal aorta diameter. Mice that were found dead without any preceding signs of suffering were defined as sudden death.

Venous bypass grafting was used as model of vascular injury for the development of neointimal hyperplasia and accelerated atherosclerosis. Osmotic minipumps were implanted 24 hours prior to vein graft surgery to allow adequate circulating levels of apelin/angiotensin at the time of vascular injury. Vein graft surgery was performed as described previously. Briefly, 10 to 12 week-old male mice were anesthetized using inhaled isoflurane. The right common carotid artery was isolated and mobilized from the thoracic inlet to the bifurcation, divided at its midpoint, and cuffs placed over the ends. The artery was inverted over the cuffs and ligated with 8-0 silk sutures. The supradiaphragmatic vena cava from an isogenic female littermate donor mouse was harvested and grafted as an interposition graft by sleeving the vein over the 2 ends of the carotid artery, and ligating with 8-0 silk sutures. Vigorous pulsation in the conduit vessel confirmed successful engraftment. The total operating time for the procedure was 30-40 minutes.

Tissue preparation, histology and lesion quantification. Mice were euthanized 28 days following implantation of osmotic mini-pumps. The thoracic cage was removed and the animal perfused with phosphate buffered saline solution (PBS) for 2 minutes. The entire aorta and vein graft were exposed and the periadventitial tissue and scar tissue dissected and removed. Subsequently mice were perfusion fixed in situ with 4% phosphate-buffered paraformaldehyde. In some animals aorta and lung were removed fresh for biochemical assays.

Aorta and vein grafts were excised, fixed in paraformaldehyde overnight, dehydrated in graded ethanol solution, and paraffin embedded or removed fresh and snap frozen in OCT. Prior to embedding, each graft was divided at its midpoint to provide sections from the body of the graft, avoiding the cuff anastomoses. Grafts were sectioned for 150 μM from the midpoint, collecting 5 μM sections. Three representative sections, separated by 50 μM, were stained with Masson/Goldner stain for analysis. Lesion quantification was similar to that described previously. Vessel wall area was determined by subtracting the luminal area from total vessel area. Neointimal area was defined as the area inside the internal elastic lamina. Image analysis was performed using Image Pro Plus software (Media Cybernetics, Silver Springs, Md.).

Lipid and lipoprotein analysis. Total plasma cholesterol and triglyceride concentrations were measured using enzymatic assay on an automated analyzer (Roche, Switzerland).

Electron paramagnetic resonance (EPR) spectroscopy. EPR spectroscopy was used to quantify vascular NO production according to previously described and validated methods. In brief, freshly harvested lung homogenate (n=4 to 8 per group) were stimulated with calcium ionophore (A23187; 1 μmol/L) in 250 μl Krebs-HEPES buffer then incubated with colloid $Fe(DETC)_2$ (285 μM) at 37° C. for 90 minutes. After incubation, lung homogenates were snap frozen in a column of Krebs-HEPES buffer in liquid nitrogen and EPR spectra were obtained using an EPR spectrometer (Resonance Instruments, Model 8400, Skokie, Ill.). Signals were quantified by measuring the total amplitude, after correction of baseline, and after subtracting background signals from incubation with colloid $Fe(DETC)_2$ alone. Human umbilical vein endothelial cells served as the positive control.

Lucigenin-enhanced chemiluminescence. Total aortic superoxide was measured by lucigenin-enhanced chemiluminescence as described previously. Aortas were harvested flushed with Krebs-HEPES buffer, opened longitudinally and divided into halves. Vessels were gassed with 95% oxygen/5% carbon dioxide in warmed Krebs-HEPES buffer for 30 minutes before measurements of chemiluminescence in a luminometer (manufacturer, location) using 20 μmol/L lucigenin. One half of each vessel was incubated in L-NAME (1 mmol/L). After measuring baseline readings for 4 minutes, samples were equilibrated and dark adapted for 5 mins, and chemiluminescence was recorded for 10 minutes. Recordings were performed blinded to the samples identity. Results were expressed as counts per second per milligram of tissue dry weight.

Oxidative fluorescent microtopography. Superoxide was detected in the layers of the vessel wall using fluorescent probe dihydroethidium as described previously. Fresh segments of upper descending thoracic aorta were frozen in OCT compound. Cryosections (30 μm) were incubated with Krebs-HEPES buffer for 30 minutes at 37° C. with or without 1 mmol/l L-NAME (Sigma), 50 μmol/l apocyanin (Sigma), 50 U/ml superoxide dismutase (Sigma) followed by 5 minutes dark incubation with 2 μmol/l dihydroethidium (DHE; Molecular Probes). Images were obtained on a confocal microscope (Bio-Rad MRC-1024 laser; filter settings: excitation filter 488 nm; emission filter 550 nm). 2-hydroxyethidium fluorescence was measured from high power (60× mag) images. Endothelium by quantifying fluorescence (intensity×area) on the luminal side of the internal elastic lamina, media between the internal and external elastic lamina, and adventitia outside the external elastic lamina. Quantification was performed using Image Pro Plus software (Media Cybernetics, Silver Springs, Md.). Medial Analysis was performed blind to the samples identity. Mean fluorescence was calculated from 4 separate high power fields from each quadrant to produce n=1.

cDNA Constructs APJ expression construct was purchased from cDNA.org. AT1R construct was obtained from Dr. Marc Caron. AT1R transcript was inserted into a pEGFP-N1 vector (Clonetech). The NF-kB and SRE luciferase reporter constructs were obtained from BD Biosciences.

Cell Culture, Transfections, and Stimulation Assays HEK293 cells were cultured in Dulbecco's modified Eagle's medium with 10% fetal bovine serum, 10 units/ml penicillin, and 100 μg/ml streptomycin. Transient transfection of the HEK293 cells was carried out using FuGene reagent per manufacturer's protocols in 6 well plates (Roche). Pulmonary artery smooth muscle cells were grown in growth medium per manufacturer's protocols. For ERK phosphorylation, transfected HEK293 cells were serum starved for 3 hours and incubated with the agonist for designated times at 37 C. Cells were immediately lysed. For luciferase assays, transfected cells were serum starved for 3 hours, then stimulated with the designated ligand for 24 hours.

Immunoblotting. Lung homogenate (n≧3 per group) were homogenized on ice for 20 seconds in lysis buffer (50 mmol/L Tris, pH 7.5, 150 mmol/L NaCl, 0.1% SDS, 0.5% deoxycholate, 1% Nonidet P-40) containing protease inhibitors (Complete; Boehringer Mannheim) and 1 mmol/L phenylmethylsulfonyl fluoride. Protein lysates (8 μg) were resolved using SDS-PAGE and transferred to polyvinylidene difluoride membranes. Membranes were incubated with a 1:2000 dilution of mouse anti-eNOS monoclonal antibody (Cell Signaling, Location), followed by a 1:2500 dilution of rabbit anti-mouse horseradish peroxidase-conjugated secondary antibody (Promega). Protein bands were visualized by chemiluminescence.

Immunoprecipitation and Western Blotting Immunoprecipitation was performed as previously described (REF). In brief, cells were lysed using 10× Cell Lysis Buffer (Cell Signaling Technologies CITY). Lysates were precleared with protein G and immunoprecipitation was performed with the respective antibodies at concentration of 1 mg/mL for 24 hrs at 4C. Protein G agarose was added and incubated for additional 2 hours. Western blotting on SDS-PAGE gels were performed as previously described, and the bands were visualized using the enhanced chemiluminescence system (Amersham Biosciences).

Materials Anti-GFP and anti-HA antibodies were purchased from Roche Applied Biosciences. Anti-APJ antibody was purchased from R&D Systems. Anti-AT1R antibody was purchased from Abcam. Protein G-agarose was purchased from Sigma-Aldrich. Apelin-13 was purchased from American Peptide and angiotensin 11 was purchased from Sigma-Aldrich. Infusion pumps were purchased from Alzet.

Chronic Infusion and Hemodynamic Assessment All animal experiments were performed in accordance with Stanford University Animal Care Guidelines; protocols were approved by the Stanford University Institutional Review Board. Infusion pumps were implanted into 9 week old ApoE deficient mice fed high fat diet. Echocardiograms were performed using (MACHINE) at baseline prior to implantation and at 4 weeks immediately prior to sacrifice. Tail cuff blood pressure measurements were made in 5 day intervals using (MACHINE). At the end of the four week infusion period tissues were fixed with intracardiac infusion of paraformaldehyde.

Atherosclerotic Lesion Analysis Atherosclerosis lesion area was determined as described previously. Briefly, the arterial tree was perfused with PBS (pH 7.3) and then perfusion fixed with phosphate-buffered paraformaldehyde (3%, pH 7.3). The heart and full length of the aorta-to-iliac bifurcation was exposed and dissected carefully from any surrounding tissues. Aortas were then opened along the ventral midline and dissected free of the animal and pinned out flat, intimal side up, onto black wax. Aortic images were captured with a digital camera (DMC1) mounted on a Leica MZ6 stereomicroscope and analyzed using Fovea Pro (Reindeer Graphics, Asheville, N.C.). Percent lesion area was calculated as total lesion area divided by total surface area.

Statistical analysis. Data are presented as mean ±SEM. Data were subjected to the Kolmogorov-Smirnov test to determine distribution. Groups were compared using the Mann-Whitney U test for non-parametric data or the Students t-test for parametric data. When comparing multiple groups data were analyzed by analysis of variance with Bonferroni's post test. For multiple testing for parametric data. A value of p<0.05 was considered statistically significant for multiple testing for parametric data. A value of P<0.05 was considered statistically significant Equivalents Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

What is claimed is:

1. A method of improving a hemodynamic parameter of a human subject suffering from heart failure comprising:
  administering an effective dose of a composition comprising an apelin peptide selected from the group consisting of SEQ ID NO:1, SEQ ID NO:2 and SEQ ID NO:4, wherein the apelin peptide is administered in an amount effective to improve at least one hemodynamic parameter wherein the hemodynamic parameter is ventricular preload, ventricular afterload, contractile reserve, or cardiac output.

2. The method of claim 1, wherein the apelin peptide is administered continuously or intermittently for at least 3 days.

3. The method of claim 1, wherein the apelin peptide is administered continuously or intermittently for at least one week.

4. The method of claim 1, wherein the apelin peptide effective dose is from 0.001 to 30 mg/kg body weight.

5. The method of claim 1, wherein the apelin peptide effective dose is from 0.01 to 25 mg/kg body weight.

6. The method of claim 1, wherein the apelin peptide effective dose is from 0.1 to 20 mg/kg body weight.

7. A method of improving at least one hemodynamic parameter of a human subject suffering from atherosclerosis comprising
  administering an effective dose of a composition comprising an apelin peptide selected from the group consisting of SEQ ID NO:1, SEQ ID NO:2 and SEQ ID NO:4 to the subject,
  and wherein the at least one hemodynamic parameter is ventricular preload, ventricular afterload, contractile reserve, or cardiac output is improved.

8. The method of claim 7, wherein the apelin peptide is administered continuously or intermittently for at least 3 days.

9. A method of improving exercise capacity of a human subject having heart failure comprising:
  administering to the subject an effective dose of a composition comprising an apelin peptide selected from the group consisting of SEQ ID NO:1, SEQ ID NO:2 and SEQ ID NO:4, wherein the apelin peptide is administered chronically in an amount effective to improve exercise capacity in said subject.

10. The method of claim 9, wherein the apelin peptide is administered continuously or intermittently for at least 3 days.

11. The method of claim 7, wherein the apelin peptide is administered continuously or intermittently for at least one week.

12. The method of claim 7, wherein the apelin peptide effective dose is from 0.1 to 20 mg/kg body weight.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Homo sapiens

<400> SEQUENCE: 1

Arg Pro Arg Leu Ser His Lys Gly Pro Met Pro Phe
 1               5                  10

<210> SEQ ID NO 2
<211> LENGTH: 13
```

-continued

```
<212> TYPE: PRT
<213> ORGANISM: Homo sapiens

<400> SEQUENCE: 2

Gln Arg Pro Arg Leu Ser His Lys Gly Pro Met Pro Phe
1               5                   10

<210> SEQ ID NO 3
<211> LENGTH: 36
<212> TYPE: PRT
<213> ORGANISM: Homo sapiens

<400> SEQUENCE: 3

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35

<210> SEQ ID NO 4
<211> LENGTH: 13
<212> TYPE: PRT
<213> ORGANISM: Homo sapiens
<220> FEATURE:
<221> NAME/KEY: VARIANT
<222> LOCATION: 1
<223> OTHER INFORMATION: Xaa = pyroglutamylated residue

<400> SEQUENCE: 4

Xaa Arg Pro Arg Leu Ser His Lys Gly Pro Met Pro Phe
1               5                   10
```